(12) United States Patent
Hirano et al.

(10) Patent No.: US 9,506,094 B2
(45) Date of Patent: Nov. 29, 2016

(54) METHOD FOR PRODUCING L-AMINO ACID USING MICROORGANISM HAVING INCREASED PHOSPHATE TRANSPORTER ACTIVITY

(71) Applicant: AJINOMOTO CO., INC., Tokyo (JP)

(72) Inventors: Seiko Hirano, Kanagawa (JP); Kazuyuki Hayashi, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/796,326

(22) Filed: Jul. 10, 2015

(65) Prior Publication Data

US 2015/0307907 A1    Oct. 29, 2015

Related U.S. Application Data

(63) Continuation of application No. PCT/JP2014/062752, filed on May 13, 2014.

(30) Foreign Application Priority Data

May 13, 2013 (JP) .................... 2013-101589
Oct. 22, 2013 (JP) .................... 2013-219274

(51) Int. Cl.
*C12P 13/14* (2006.01)
*C12P 13/04* (2006.01)
*C07K 14/34* (2006.01)

(52) U.S. Cl.
CPC ............. *C12P 13/14* (2013.01); *C07K 14/34* (2013.01); *C12P 13/04* (2013.01)

(58) Field of Classification Search
CPC ............ C07K 14/34; C12P 13/04; C12P 13/14
See application file for complete search history.

(56) References Cited

U.S. PATENT DOCUMENTS

| | | |
|---|---|---|
| 5,168,056 A | 12/1992 | Frost |
| 5,776,736 A | 7/1998 | Frost et al. |
| 5,906,925 A | 5/1999 | Liao |
| 7,867,735 B2 | 1/2011 | Hirano et al. |
| 7,927,844 B2 | 4/2011 | Nakamura et al. |
| 8,017,363 B2 | 9/2011 | Gunji et al. |
| 8,110,381 B2 | 2/2012 | Hirano et al. |
| 8,278,074 B2 | 10/2012 | Nakamura et al. |
| 8,512,987 B2 | 8/2013 | Nagai et al. |
| 2002/0106751 A1 | 8/2002 | Farwick et al. |
| 2002/0197605 A1 | 12/2002 | Nakagawa |
| 2012/0040415 A1 | 2/2012 | Nakahara et al. |
| 2013/0288313 A1 | 10/2013 | Nagai et al. |

FOREIGN PATENT DOCUMENTS

| | | |
|---|---|---|
| KR | 10-2001-0082585 | 8/2001 |
| WO | WO02/22671 | 3/2002 |
| WO | WO2015/050276 A1 | 4/2015 |

OTHER PUBLICATIONS

Sousa et al., Microbiology 148(Pt5):1291-1303, 2002.*
Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Sadowski et al., Current Opinion in Structural Biology 19:357-362, 2009.*
Harris, R. M., et al., "Characterization of PitA and PitB from *Escherichia coli*," J. Bacteriol. 2001;183(17):5008-5014.
Ishige, T., et al., "The Phosphate Starvation Stimulon of Corynebacterium glutamicum Determined by DNA Microarray Analyses," J. Bacteriol. 2003;185(15):4519-4529.
Lv, Y., et al., "Genome Sequence of Corynebacterium glutamicum ATCC 14067, Which Provides Insight Into Amino Acid Biosynthesis in Coryneform Bacteria," J. Bacteriol. 2012;194(3):742-743.
Phosphate/sulphate permease [Corynebacterium glutamicum K051]. (online) Mar. 25, 2013 (retrieved on Aug. 11, 2014) retrieved from <http://www.ncbi.nlm.nih.gov/protein/470173484?sat=17&satkey=2422518>.
International Search Report for PCT Patent App. No. PCT/JP2014/062752 (Aug. 19, 2014).
Written Opinion for PCT Patent App. No. PCT/JP2014/062752 (Aug. 19, 2014).
Supplementary European Search Report for European Patent App. No. 14797459.6 (Aug. 3, 2015).
Communication Pursuant to Article 94(3) EPC for European Patent App. No. 14797459.6 (Aug. 14, 2015).
Hayashi, K., et al., "Development of PCR-based allele-specific and InDel marker sets for nine rice blast resistance genes," Theor. Appl. Genet. 2006;113:251-260.
Office Action from European Patent App. No. 14797459.6 (Feb. 17, 2016).
Office Action issued from the Korean Intellectual Property Office in Korean Patent Application 10-2015-7019590 on Oct. 20, 2016.

* cited by examiner

*Primary Examiner* — Delia Ramirez
(74) *Attorney, Agent, or Firm* — Shelly Guest Cermak; Cermak Nakajima & McGowan LLP

(57) ABSTRACT

A method for producing an L-amino acid is provided. An L-amino acid is produced by culturing a coryneform bacterium having an L-amino acid-producing ability, which is modified so that the activity of a phosphate transporter is increased, in a medium, and collecting the L-amino acid from the medium.

11 Claims, No Drawings

SEQUENCE LISTING

<160> NUMBER OF SEQ ID NOS: 28

<210> SEQ ID NO 1
<211> LENGTH: 1500
<212> TYPE: DNA
<213> ORGANISM: Escherichia coli MG1655
<220> FEATURE:
<221> NAME/KEY: CDS
<222> LOCATION: (1)..(1500)

<400> SEQUENCE: 1

```
atg cta cat ttg ttt gct ggc ctg gat ttg cat acc ggg ctg tta tta      48
Met Leu His Leu Phe Ala Gly Leu Asp Leu His Thr Gly Leu Leu Leu
1               5                   10                  15 ttg ctt gca ctg gct ttt gtg ctg ttc tac gaa gcc atc aat ggt ttc      96
Leu Leu Ala Leu Ala Phe Val Leu Phe Tyr Glu Ala Ile Asn Gly Phe
            20                  25                  30 cat gac aca gcc aac gcc gtg gca acc gtt atc tat acc cgc gcg atg    144
His Asp Thr Ala Asn Ala Val Ala Thr Val Ile Tyr Thr Arg Ala Met
        35                  40                  45 cgt tct cag ctc gcc gtg gtt atg gcg gcg gta ttc aac ttt ttg ggt    192
Arg Ser Gln Leu Ala Val Val Met Ala Ala Val Phe Asn Phe Leu Gly
    50                  55                  60 gtt ttg ctg ggt ggt ctg agt gtt gcc tat gcc att gtg cat atg ctg    240
Val Leu Leu Gly Gly Leu Ser Val Ala Tyr Ala Ile Val His Met Leu
65                  70                  75                  80 ccg acg gat ctg ctg ctt aat atg gga tcg tct cat ggc ctt gcc atg    288
Pro Thr Asp Leu Leu Leu Asn Met Gly Ser Ser His Gly Leu Ala Met
                85                  90                  95 gtg ttc tct atg ttg ctg gcg gcg att atc tgg aac ctg ggt acc tgg    336
Val Phe Ser Met Leu Leu Ala Ala Ile Ile Trp Asn Leu Gly Thr Trp
            100                 105                 110 tac ttt ggt tta cct gca tcc agc tct cat acg ctg att ggc gcg atc    384
Tyr Phe Gly Leu Pro Ala Ser Ser Ser His Thr Leu Ile Gly Ala Ile
        115                 120                 125 atc ggg att ggt tta acc aat gcg ttg atg acc ggg acg tca gtg gtg    432
Ile Gly Ile Gly Leu Thr Asn Ala Leu Met Thr Gly Thr Ser Val Val
    130                 135                 140 gat gca ctc aat atc ccg aaa gta tta agt att ttc ggt tct ctg atc    480
Asp Ala Leu Asn Ile Pro Lys Val Leu Ser Ile Phe Gly Ser Leu Ile
145                 150                 155                 160 gtt tcc cct att gtc ggc ctg gtg ttt gct ggc ggt ctg att ttc ttg    528
Val Ser Pro Ile Val Gly Leu Val Phe Ala Gly Gly Leu Ile Phe Leu
                165                 170                 175 ctg cgt cgc tac tgg agc ggc acc aag aaa cgc gcc cgt atc cac ctg    576
Leu Arg Arg Tyr Trp Ser Gly Thr Lys Lys Arg Ala Arg Ile His Leu
            180                 185                 190 acc cca gcg gag cgt gaa aag aaa gac ggc aag aaa aag ccg ccg ttc    624
Thr Pro Ala Glu Arg Glu Lys Lys Asp Gly Lys Lys Lys Pro Pro Phe
        195                 200                 205 tgg acg cgt att gcg ctg atc ctt tcc gct atc ggc gtg gcg ttt tcg    672
Trp Thr Arg Ile Ala Leu Ile Leu Ser Ala Ile Gly Val Ala Phe Ser
    210                 215                 220 cac ggc gcg aac gat ggt cag aaa ggc att ggt ctg gtt atg ttg gta    720
His Gly Ala Asn Asp Gly Gln Lys Gly Ile Gly Leu Val Met Leu Val
225                 230                 235                 240 ttg att ggc gtc gcg cca gca ggc ttc gtg gtg aac atg aat gcc act    768
Leu Ile Gly Val Ala Pro Ala Gly Phe Val Val Asn Met Asn Ala Thr
                245                 250                 255 ggc tac gaa atc acc cgt acc cgt gat gcc atc aac aac gtc gaa gct    816
Gly Tyr Glu Ile Thr Arg Thr Arg Asp Ala Ile Asn Asn Val Glu Ala
```

```
                260                 265                 270
tac ttt gag cag cat cct gcg ctg ctc aaa cag gct acc ggt gct gat      864
Tyr Phe Glu Gln His Pro Ala Leu Leu Lys Gln Ala Thr Gly Ala Asp
        275                 280                 285 cag tta gta ccg gct ccg gaa gct ggc gca acg caa cct gcg gag ttc      912
Gln Leu Val Pro Ala Pro Glu Ala Gly Ala Thr Gln Pro Ala Glu Phe
    290                 295                 300 cac tgc cat ccg tcg aat acc att aac gcg ctc aac cgc ctg aaa ggt      960
His Cys His Pro Ser Asn Thr Ile Asn Ala Leu Asn Arg Leu Lys Gly
305                 310                 315                 320 atg ttg acc acc gat gtg gaa agc tac gac aag ctg tcg ctt gat caa     1008
Met Leu Thr Thr Asp Val Glu Ser Tyr Asp Lys Leu Ser Leu Asp Gln
                325                 330                 335 cgt agc cag atg cgc cgc att atg ctg tgc gtt tct gac act atc gac     1056
Arg Ser Gln Met Arg Arg Ile Met Leu Cys Val Ser Asp Thr Ile Asp
            340                 345                 350 aaa gtg gtg aag atg cct ggc gtg agt gct gac gat cag cgc ctg ttg     1104
Lys Val Val Lys Met Pro Gly Val Ser Ala Asp Asp Gln Arg Leu Leu
        355                 360                 365 aag aaa ctg aag tcc gac atg ctt agc acc atc gag tat gca ccg gtg     1152
Lys Lys Leu Lys Ser Asp Met Leu Ser Thr Ile Glu Tyr Ala Pro Val
    370                 375                 380 tgg atc atc atg gcg gtc gcg ctg gcg tta ggt atc ggt acg atg att     1200
Trp Ile Ile Met Ala Val Ala Leu Ala Leu Gly Ile Gly Thr Met Ile
385                 390                 395                 400 ggc tgg cgc cgt gtg gca acg act atc ggt gag aaa atc ggt aag aaa     1248
Gly Trp Arg Arg Val Ala Thr Thr Ile Gly Glu Lys Ile Gly Lys Lys
                405                 410                 415 ggc atg acc tac gct cag ggg atg tct gcc cag atg acg gcg gca gtg     1296
Gly Met Thr Tyr Ala Gln Gly Met Ser Ala Gln Met Thr Ala Ala Val
            420                 425                 430 tct atc ggc ctg gcg agt tat acc ggg atg ccg gtt tcc act act cac     1344
Ser Ile Gly Leu Ala Ser Tyr Thr Gly Met Pro Val Ser Thr Thr His
        435                 440                 445 gta ctc tcc tct tct gtc gcg ggg acg atg gtg gta gat ggt ggc ggc     1392
Val Leu Ser Ser Ser Val Ala Gly Thr Met Val Val Asp Gly Gly Gly
    450                 455                 460 tta cag cgt aaa acc gtg acc agc att ctg atg gcc tgg gtg ttt acc     1440
Leu Gln Arg Lys Thr Val Thr Ser Ile Leu Met Ala Trp Val Phe Thr
465                 470                 475                 480 ctt ccg gct gcg gta ctg ctt tcc ggc ggg ctg tac tgg ctc tcc ttg     1488
Leu Pro Ala Ala Val Leu Leu Ser Gly Gly Leu Tyr Trp Leu Ser Leu
                485                 490                 495 cag ttc ctg taa                                                      1500
Gln Phe Leu <210> SEQ ID NO 2
<211> LENGTH: 499
<212> TYPE: PRT
<213> ORGANISM: Escherichia coli MG1655

<400> SEQUENCE: 2

Met Leu His Leu Phe Ala Gly Leu Asp Leu His Thr Gly Leu Leu Leu
1               5                   10                  15

Leu Leu Ala Leu Ala Phe Val Leu Phe Tyr Glu Ala Ile Asn Gly Phe
                20                  25                  30

His Asp Thr Ala Asn Ala Val Ala Thr Val Ile Tyr Thr Arg Ala Met
            35                  40                  45

Arg Ser Gln Leu Ala Val Val Met Ala Ala Val Phe Asn Phe Leu Gly
```

```
            50                  55                  60
Val Leu Leu Gly Gly Leu Ser Val Ala Tyr Ala Ile Val His Met Leu
 65                  70                  75                  80

Pro Thr Asp Leu Leu Leu Asn Met Gly Ser Ser His Gly Leu Ala Met
                 85                  90                  95

Val Phe Ser Met Leu Leu Ala Ala Ile Ile Trp Asn Leu Gly Thr Trp
                100                 105                 110

Tyr Phe Gly Leu Pro Ala Ser Ser His Thr Leu Ile Gly Ala Ile
                115                 120                 125

Ile Gly Ile Gly Leu Thr Asn Ala Leu Met Thr Gly Thr Ser Val Val
            130                 135                 140

Asp Ala Leu Asn Ile Pro Lys Val Leu Ser Ile Phe Gly Ser Leu Ile
145                 150                 155                 160

Val Ser Pro Ile Val Gly Leu Val Phe Ala Gly Gly Leu Ile Phe Leu
                165                 170                 175

Leu Arg Arg Tyr Trp Ser Gly Thr Lys Lys Arg Ala Arg Ile His Leu
            180                 185                 190

Thr Pro Ala Glu Arg Glu Lys Lys Asp Gly Lys Lys Pro Pro Phe
            195                 200                 205

Trp Thr Arg Ile Ala Leu Ile Leu Ser Ala Ile Gly Val Ala Phe Ser
210                 215                 220

His Gly Ala Asn Asp Gly Gln Lys Gly Ile Gly Leu Val Met Leu Val
225                 230                 235                 240

Leu Ile Gly Val Ala Pro Ala Gly Phe Val Val Asn Met Asn Ala Thr
                245                 250                 255

Gly Tyr Glu Ile Thr Arg Thr Arg Asp Ala Ile Asn Asn Val Glu Ala
                260                 265                 270

Tyr Phe Glu Gln His Pro Ala Leu Leu Lys Gln Ala Thr Gly Ala Asp
            275                 280                 285

Gln Leu Val Pro Ala Pro Glu Ala Gly Ala Thr Gln Pro Ala Glu Phe
        290                 295                 300

His Cys His Pro Ser Asn Thr Ile Asn Ala Leu Asn Arg Leu Lys Gly
305                 310                 315                 320

Met Leu Thr Thr Asp Val Glu Ser Tyr Asp Lys Leu Ser Leu Asp Gln
                325                 330                 335

Arg Ser Gln Met Arg Arg Ile Met Leu Cys Val Ser Asp Thr Ile Asp
            340                 345                 350

Lys Val Val Lys Met Pro Gly Val Ser Ala Asp Gln Arg Leu Leu
            355                 360                 365

Lys Lys Leu Lys Ser Asp Met Leu Ser Thr Ile Glu Tyr Ala Pro Val
370                 375                 380

Trp Ile Ile Met Ala Val Ala Leu Ala Leu Gly Ile Gly Thr Met Ile
385                 390                 395                 400

Gly Trp Arg Arg Val Ala Thr Thr Ile Gly Glu Lys Ile Gly Lys Lys
                405                 410                 415

Gly Met Thr Tyr Ala Gln Gly Met Ser Ala Gln Met Thr Ala Ala Val
            420                 425                 430

Ser Ile Gly Leu Ala Ser Tyr Thr Gly Met Pro Val Ser Thr Thr His
            435                 440                 445

Val Leu Ser Ser Ser Val Ala Gly Thr Met Val Val Asp Gly Gly
        450                 455                 460

Leu Gln Arg Lys Thr Val Thr Ser Ile Leu Met Ala Trp Val Phe Thr
465                 470                 475                 480
```

```
Leu Pro Ala Ala Val Leu Leu Ser Gly Gly Leu Tyr Trp Leu Ser Leu
                485                 490                 495

Gln Phe Leu

<210> SEQ ID NO 3
<211> LENGTH: 1503
<212> TYPE: DNA
<213> ORGANISM: Pantoea ananatis LMG20103
<220> FEATURE:
<221> NAME/KEY: CDS
<222> LOCATION: (1)..(1503)

<400> SEQUENCE: 3 atg cta cat ctg ttt gct ggt cta gat ctt agc acc ggc ctg tta ctg        48
Met Leu His Leu Phe Ala Gly Leu Asp Leu Ser Thr Gly Leu Leu Leu
 1               5                  10                  15 ata ctt gct ctg ctg ttt gta ttg ttt tac gaa gca att aac ggc ttt        96
Ile Leu Ala Leu Leu Phe Val Leu Phe Tyr Glu Ala Ile Asn Gly Phe
                20                  25                  30 cat gat acg gcc aac gcg gtt gcg acg gtc atc tat acc cgt gcc atg       144
His Asp Thr Ala Asn Ala Val Ala Thr Val Ile Tyr Thr Arg Ala Met
            35                  40                  45 cgg gcg cag ctt gcc gtt tta atg gca ggc gtc ttc aac ttc ttt ggt       192
Arg Ala Gln Leu Ala Val Leu Met Ala Gly Val Phe Asn Phe Phe Gly
        50                  55                  60 gta ttg ctc ggc gga tta agc gtg gct tac gct atc gtg cat atg ctg       240
Val Leu Leu Gly Gly Leu Ser Val Ala Tyr Ala Ile Val His Met Leu
 65                  70                  75                  80 cct acc gat ctg ctg ctg aat gtc gga tcg gcc cac ggt ctc gcc atg       288
Pro Thr Asp Leu Leu Leu Asn Val Gly Ser Ala His Gly Leu Ala Met
                85                  90                  95 gtc ttt tcc atg ctg ctg gcg gcg att atc tgg aac ctg ggt acc tgg       336
Val Phe Ser Met Leu Leu Ala Ala Ile Ile Trp Asn Leu Gly Thr Trp
               100                 105                 110 tat ttg ggc ctg ccc gcg tcc agt tcc cat acc tta atc ggc gcg att       384
Tyr Leu Gly Leu Pro Ala Ser Ser Ser His Thr Leu Ile Gly Ala Ile
           115                 120                 125 atc ggc att ggc ctg acg aac gcg ttg atg agc ggc aca tcg gtc gtt       432
Ile Gly Ile Gly Leu Thr Asn Ala Leu Met Ser Gly Thr Ser Val Val
       130                 135                 140 gat gcg ctt aac atc ccg aaa gtg ctg aat att ttc ctg tct ctg att       480
Asp Ala Leu Asn Ile Pro Lys Val Leu Asn Ile Phe Leu Ser Leu Ile
145                 150                 155                 160 ctt tcc cct att gtc gga ctg gtg att gcg ggc agc cta att ttt ctt       528
Leu Ser Pro Ile Val Gly Leu Val Ile Ala Gly Ser Leu Ile Phe Leu
                165                 170                 175 ctc cgc cgt tac tgg agt aac acc aaa aag cgt gcg cgt att cat atg       576
Leu Arg Arg Tyr Trp Ser Asn Thr Lys Lys Arg Ala Arg Ile His Met
            180                 185                 190 acg ccc gcc gat cgc gag aag att gat ggc aag aaa aaa ccg cct ttc       624
Thr Pro Ala Asp Arg Glu Lys Ile Asp Gly Lys Lys Lys Pro Pro Phe
        195                 200                 205 tgg acg cgc acg gca ctg att atc tcc gcc att ggt gtc agt tat tca       672
Trp Thr Arg Thr Ala Leu Ile Ile Ser Ala Ile Gly Val Ser Tyr Ser
    210                 215                 220 cac ggt gcg aac gac ggg cag aaa ggc att ggc ctg atc atg ctg gtt       720
His Gly Ala Asn Asp Gly Gln Lys Gly Ile Gly Leu Ile Met Leu Val
225                 230                 235                 240 ctg ata ggc gtt gcg cca gcc ggc ttc gtg gtg aat atg aac gca tcg       768
Leu Ile Gly Val Ala Pro Ala Gly Phe Val Val Asn Met Asn Ala Ser
```

```
                     245                 250                 255
ggt tac gac att acg cgt aca cgg gat gcg gtc aat cat ctt gag cag     816
Gly Tyr Asp Ile Thr Arg Thr Arg Asp Ala Val Asn His Leu Glu Gln
                260                 265                 270 tat tat caa cag cac cag gcc tca ctg aac cac atc atc gag atg gcg     864
Tyr Tyr Gln Gln His Gln Ala Ser Leu Asn His Ile Ile Glu Met Ala
            275                 280                 285 ccg cct aag ctg ccc acc ccg gaa gaa gtg gcg ccg gta tca tcg aca     912
Pro Pro Lys Leu Pro Thr Pro Glu Glu Val Ala Pro Val Ser Ser Thr
        290                 295                 300 gag ttt cat tgc gac agt gct cgt gcg ctg cag gcc gtg caa cgt gct     960
Glu Phe His Cys Asp Ser Ala Arg Ala Leu Gln Ala Val Gln Arg Ala
305                 310                 315                 320 cag ttg ctg ctg aac aac ctg caa agc tac agc gat ctg tcc gtc gag    1008
Gln Leu Leu Leu Asn Asn Leu Gln Ser Tyr Ser Asp Leu Ser Val Glu
                325                 330                 335 cag cgt agt cag atg cgt cgc ctg ctg ctg tgt att tcc gac acc gcc    1056
Gln Arg Ser Gln Met Arg Arg Leu Leu Leu Cys Ile Ser Asp Thr Ala
            340                 345                 350 gat aaa gcg gcg aag ctg ccg gaa acc tct cca gac gat aaa cgt ttc    1104
Asp Lys Ala Ala Lys Leu Pro Glu Thr Ser Pro Asp Asp Lys Arg Phe
        355                 360                 365 ctg ggc aag ctc aaa ggc gat ctg ttg aac acc att gag tac gcg ccg    1152
Leu Gly Lys Leu Lys Gly Asp Leu Leu Asn Thr Ile Glu Tyr Ala Pro
    370                 375                 380 gta tgg atc atc atg gcg gtt gcg ctg gca tta ggc gtc ggc acc atg    1200
Val Trp Ile Ile Met Ala Val Ala Leu Ala Leu Gly Val Gly Thr Met
385                 390                 395                 400 atc ggc tgg cgt cgc gtg gcc acc acc atc ggt gag aaa att ggt aag    1248
Ile Gly Trp Arg Arg Val Ala Thr Thr Ile Gly Glu Lys Ile Gly Lys
                405                 410                 415 aag ggc atg acc tat gcg cag ggc atg tct gcg cag gtg acg gcg gcc    1296
Lys Gly Met Thr Tyr Ala Gln Gly Met Ser Ala Gln Val Thr Ala Ala
            420                 425                 430 gtg tcg ata ggc atc gcc agc tac acc ggc atg ccg gtc tcc acc acg    1344
Val Ser Ile Gly Ile Ala Ser Tyr Thr Gly Met Pro Val Ser Thr Thr
        435                 440                 445 cat atc ctc tct tct tcc gtt gcc ggc acc atg ctg gtt gac ggc ggc    1392
His Ile Leu Ser Ser Ser Val Ala Gly Thr Met Leu Val Asp Gly Gly
    450                 455                 460 ggc ttg cag ggc aaa acc atc aaa aac atc gcc atg gcg tgg gta ttt    1440
Gly Leu Gln Gly Lys Thr Ile Lys Asn Ile Ala Met Ala Trp Val Phe
465                 470                 475                 480 acc ctg ccg gtc tgt att ttg tta tcg ggt tcg ctc tac tgg ata gcg    1488
Thr Leu Pro Val Cys Ile Leu Leu Ser Gly Ser Leu Tyr Trp Ile Ala
                485                 490                 495 ctg aaa ctc atc tga                                                1503
Leu Lys Leu Ile
            500

<210> SEQ ID NO 4
<211> LENGTH: 500
<212> TYPE: PRT
<213> ORGANISM: Pantoea ananatis LMG20103

<400> SEQUENCE: 4

Met Leu His Leu Phe Ala Gly Leu Asp Leu Ser Thr Gly Leu Leu Leu
1               5                   10                  15

Ile Leu Ala Leu Leu Phe Val Leu Phe Tyr Glu Ala Ile Asn Gly Phe
            20                  25                  30
```

-continued

His Asp Thr Ala Asn Ala Val Ala Thr Val Ile Tyr Thr Arg Ala Met
            35                  40                  45

Arg Ala Gln Leu Ala Val Leu Met Ala Gly Val Phe Asn Phe Phe Gly
        50                  55                  60

Val Leu Leu Gly Gly Leu Ser Val Ala Tyr Ala Ile Val His Met Leu
65                  70                  75                  80

Pro Thr Asp Leu Leu Leu Asn Val Gly Ser Ala His Gly Leu Ala Met
                85                  90                  95

Val Phe Ser Met Leu Leu Ala Ala Ile Ile Trp Asn Leu Gly Thr Trp
                100                 105                 110

Tyr Leu Gly Leu Pro Ala Ser Ser His Thr Leu Ile Gly Ala Ile
            115                 120                 125

Ile Gly Ile Gly Leu Thr Asn Ala Leu Met Ser Gly Thr Ser Val Val
            130                 135                 140

Asp Ala Leu Asn Ile Pro Lys Val Leu Asn Ile Phe Leu Ser Leu Ile
145                 150                 155                 160

Leu Ser Pro Ile Val Gly Leu Val Ile Ala Gly Ser Leu Ile Phe Leu
                165                 170                 175

Leu Arg Arg Tyr Trp Ser Asn Thr Lys Lys Arg Ala Arg Ile His Met
            180                 185                 190

Thr Pro Ala Asp Arg Glu Lys Ile Asp Gly Lys Lys Pro Pro Phe
            195                 200                 205

Trp Thr Arg Thr Ala Leu Ile Ile Ser Ala Ile Gly Val Ser Tyr Ser
            210                 215                 220

His Gly Ala Asn Asp Gly Gln Lys Gly Ile Gly Leu Ile Met Leu Val
225                 230                 235                 240

Leu Ile Gly Val Ala Pro Ala Gly Phe Val Val Asn Met Asn Ala Ser
                245                 250                 255

Gly Tyr Asp Ile Thr Arg Thr Arg Asp Ala Val Asn His Leu Glu Gln
            260                 265                 270

Tyr Tyr Gln Gln His Gln Ala Ser Leu Asn His Ile Ile Glu Met Ala
        275                 280                 285

Pro Pro Lys Leu Pro Thr Pro Glu Glu Val Ala Pro Val Ser Ser Thr
            290                 295                 300

Glu Phe His Cys Asp Ser Ala Arg Ala Leu Gln Ala Val Gln Arg Ala
305                 310                 315                 320

Gln Leu Leu Leu Asn Asn Leu Gln Ser Tyr Ser Asp Leu Ser Val Glu
                325                 330                 335

Gln Arg Ser Gln Met Arg Arg Leu Leu Leu Cys Ile Ser Asp Thr Ala
            340                 345                 350

Asp Lys Ala Ala Lys Leu Pro Glu Thr Ser Pro Asp Asp Lys Arg Phe
355                 360                 365

Leu Gly Lys Leu Lys Gly Asp Leu Leu Asn Thr Ile Glu Tyr Ala Pro
    370                 375                 380

Val Trp Ile Ile Met Ala Val Ala Leu Ala Leu Gly Val Gly Thr Met
385                 390                 395                 400

Ile Gly Trp Arg Arg Val Ala Thr Thr Ile Gly Glu Lys Ile Gly Lys
                405                 410                 415

Lys Gly Met Thr Tyr Ala Gln Gly Met Ser Ala Gln Val Thr Ala Ala
            420                 425                 430

Val Ser Ile Gly Ile Ala Ser Tyr Thr Gly Met Pro Val Ser Thr Thr
                435                 440                 445

-continued

```
            His Ile Leu Ser Ser Val Ala Gly Thr Met Leu Val Asp Gly Gly
                    450                 455                 460

Gly Leu Gln Gly Lys Thr Ile Lys Asn Ile Ala Met Ala Trp Val Phe
            465                 470                 475                 480

Thr Leu Pro Val Cys Ile Leu Leu Ser Gly Ser Leu Tyr Trp Ile Ala
                            485                 490                 495

Leu Lys Leu Ile
                        500

<210> SEQ ID NO 5
<211> LENGTH: 1386
<212> TYPE: DNA
<213> ORGANISM: Corynebacterium glutamicum 2256 (ATCC 13869)
<220> FEATURE:
<221> NAME/KEY: CDS
<222> LOCATION: (1)..(1386)

<400> SEQUENCE: 5 atg gtc acc cca atc atg ggg aat tcg aac tct atc ctg ggc att tac        48
Met Val Thr Pro Ile Met Gly Asn Ser Asn Ser Ile Leu Gly Ile Tyr
  1               5                  10                  15 cgt cag aaa atc caa aat cga cgt ttg gtt tct acg ctt ttt agg gca        96
Arg Gln Lys Ile Gln Asn Arg Arg Leu Val Ser Thr Leu Phe Arg Ala
             20                  25                  30 tac ttc cca atc gtg acc gag ctg att att tta ttg att gtt atc gtg       144
Tyr Phe Pro Ile Val Thr Glu Leu Ile Ile Leu Leu Ile Val Ile Val
         35                  40                  45 acg gcg ctc gcc ttc gat ttc aca aac gga ttc cac gac acc ggc aat       192
Thr Ala Leu Ala Phe Asp Phe Thr Asn Gly Phe His Asp Thr Gly Asn
     50                  55                  60 gcg atg gcc aca tcc att gcc aca ggc gct cta aaa cct aaa gtc gcc       240
Ala Met Ala Thr Ser Ile Ala Thr Gly Ala Leu Lys Pro Lys Val Ala
 65                  70                  75                  80 gtg gca cta tcc gcc tca ctg aac ctt gtt ggc gca ttc ctc tct gta       288
Val Ala Leu Ser Ala Ser Leu Asn Leu Val Gly Ala Phe Leu Ser Val
                 85                  90                  95 gaa gtt gcg aca act gtt gcc aaa ggc gtt gtt gac ctc gac caa ttc       336
Glu Val Ala Thr Thr Val Ala Lys Gly Val Val Asp Leu Asp Gln Phe
            100                 105                 110 gac cta agc aat gcc tgg gat tcc cac cag ctc ctg ctt gtc gtc ttc       384
Asp Leu Ser Asn Ala Trp Asp Ser His Gln Leu Leu Leu Val Val Phe
        115                 120                 125 gcc ggc ctc att ggc gcc atc gtc tgg aac ctt ctg acc tgg ctg cta       432
Ala Gly Leu Ile Gly Ala Ile Val Trp Asn Leu Leu Thr Trp Leu Leu
    130                 135                 140 ggc att cct tcc agc tcc tct cac gca ctt ttc ggt ggc ctc att ggc       480
Gly Ile Pro Ser Ser Ser Ser His Ala Leu Phe Gly Gly Leu Ile Gly
145                 150                 155                 160 gcc gca att gct tca ctc ggt ttc ggc gga gtg gtg tgg gaa ggt gtc       528
Ala Ala Ile Ala Ser Leu Gly Phe Gly Gly Val Val Trp Glu Gly Val
                165                 170                 175 ttg tcc aag atg atc atc cca gca ttg gct gca cca gtt gtt gca ggt       576
Leu Ser Lys Met Ile Ile Pro Ala Leu Ala Ala Pro Val Val Ala Gly
            180                 185                 190 ctc gtg gcc gcc atc ggc act ttc gcc gtg tac agc atc aca aag gca       624
Leu Val Ala Ala Ile Gly Thr Phe Ala Val Tyr Ser Ile Thr Lys Ala
        195                 200                 205 gtt gga gac aac gag aag aac cgt tac ttc cgc tgg ggt cag atc ggc       672
Val Gly Asp Asn Glu Lys Asn Arg Tyr Phe Arg Trp Gly Gln Ile Gly
    210                 215                 220
```

```
tcc gct tcc ctg gtt tcc ctg gca cac ggc acc aac gat gcc cag aag      720
Ser Ala Ser Leu Val Ser Leu Ala His Gly Thr Asn Asp Ala Gln Lys
225                 230                 235                 240 acc atg ggc gtt atc ttc ctt tcc ctg gtt gcc acc ggt cac ctg gga      768
Thr Met Gly Val Ile Phe Leu Ser Leu Val Ala Thr Gly His Leu Gly
                245                 250                 255 act gac gct gac atc cca ttc tgg gtc aag gct tca tgt gca ttg gca      816
Thr Asp Ala Asp Ile Pro Phe Trp Val Lys Ala Ser Cys Ala Leu Ala
            260                 265                 270 atc gca atc ggt acc tac ttg ggt ggt tgg cgc gtt atc cgc aca ctg      864
Ile Ala Ile Gly Thr Tyr Leu Gly Gly Trp Arg Val Ile Arg Thr Leu
        275                 280                 285 ggc aaa ggc ttg gtt gag att gat tcc cct cag ggc atg gca gca gaa      912
Gly Lys Gly Leu Val Glu Ile Asp Ser Pro Gln Gly Met Ala Ala Glu
    290                 295                 300 act tct tct gca gca atc att ttg act tct tcc cac ttc ggt atg gca      960
Thr Ser Ser Ala Ala Ile Ile Leu Thr Ser Ser His Phe Gly Met Ala
305                 310                 315                 320 ctg tcc acc act cac gtt gct act ggc tcc atc atg ggt acc ggc att     1008
Leu Ser Thr Thr His Val Ala Thr Gly Ser Ile Met Gly Thr Gly Ile
                325                 330                 335 gga cgt aaa ggt gcg aag gtt cgt tgg tcc gtc gca gga cgc atg gca     1056
Gly Arg Lys Gly Ala Lys Val Arg Trp Ser Val Ala Gly Arg Met Ala
            340                 345                 350 atg gcc tgg gtt atc acc ctc cct gcc tcc gcg atc gtt ggc gtt ttc     1104
Met Ala Trp Val Ile Thr Leu Pro Ala Ser Ala Ile Val Gly Val Phe
        355                 360                 365 tgc tgg tgg gta gct cac gga att ggt ctt atc agc tca gac ctc ctc     1152
Cys Trp Trp Val Ala His Gly Ile Gly Leu Ile Ser Ser Asp Leu Leu
    370                 375                 380 gga gtc ctc gtt gca ttc gcc att ctg gtc att ctg tct ggc tac att     1200
Gly Val Leu Val Ala Phe Ala Ile Leu Val Ile Leu Ser Gly Tyr Ile
385                 390                 395                 400 tac gcc cgt tcc cgt cgc gtg cct gtt gat cca agc aac gtc aac gct     1248
Tyr Ala Arg Ser Arg Arg Val Pro Val Asp Pro Ser Asn Val Asn Ala
                405                 410                 415 gac tgg aat gaa gaa tca aac agc gtg gaa cct gca aca cct tcc gcc     1296
Asp Trp Asn Glu Glu Ser Asn Ser Val Glu Pro Ala Thr Pro Ser Ala
            420                 425                 430 ccg gct gct tct gag att gca gaa gct cct gcc gct cca gcc gct cat     1344
Pro Ala Ala Ser Glu Ile Ala Glu Ala Pro Ala Ala Pro Ala Ala His
        435                 440                 445 gcc gtt caa gat ctc aac aac gag aat gag gta acc aag taa             1386
Ala Val Gln Asp Leu Asn Asn Glu Asn Glu Val Thr Lys
    450                 455                 460

<210> SEQ ID NO 6
<211> LENGTH: 461
<212> TYPE: PRT
<213> ORGANISM: Corynebacterium glutamicum 2256 (ATCC 13869)

<400> SEQUENCE: 6

Met Val Thr Pro Ile Met Gly Asn Ser Asn Ser Ile Leu Gly Ile Tyr
1               5                   10                  15

Arg Gln Lys Ile Gln Asn Arg Arg Leu Val Ser Thr Leu Phe Arg Ala
            20                  25                  30

Tyr Phe Pro Ile Val Thr Glu Leu Ile Ile Leu Leu Ile Val Ile Val
        35                  40                  45

Thr Ala Leu Ala Phe Asp Phe Thr Asn Gly Phe His Asp Thr Gly Asn
    50                  55                  60
```

Ala Met Ala Thr Ser Ile Ala Thr Gly Ala Leu Lys Pro Lys Val Ala
 65                  70                  75                  80

Val Ala Leu Ser Ala Ser Leu Asn Leu Val Gly Ala Phe Leu Ser Val
                 85                  90                  95

Glu Val Ala Thr Thr Val Ala Lys Gly Val Val Asp Leu Asp Gln Phe
            100                 105                 110

Asp Leu Ser Asn Ala Trp Asp Ser His Gln Leu Leu Val Val Phe
        115                 120                 125

Ala Gly Leu Ile Gly Ala Ile Val Trp Asn Leu Leu Thr Trp Leu Leu
130                 135                 140

Gly Ile Pro Ser Ser Ser His Ala Leu Phe Gly Gly Leu Ile Gly
145                 150                 155                 160

Ala Ala Ile Ala Ser Leu Gly Phe Gly Gly Val Val Trp Glu Gly Val
                165                 170                 175

Leu Ser Lys Met Ile Ile Pro Ala Leu Ala Ala Pro Val Val Ala Gly
            180                 185                 190

Leu Val Ala Ala Ile Gly Thr Phe Ala Val Tyr Ser Ile Thr Lys Ala
        195                 200                 205

Val Gly Asp Asn Glu Lys Asn Arg Tyr Phe Arg Trp Gly Gln Ile Gly
210                 215                 220

Ser Ala Ser Leu Val Ser Leu Ala His Gly Thr Asn Asp Ala Gln Lys
225                 230                 235                 240

Thr Met Gly Val Ile Phe Leu Ser Leu Val Ala Thr Gly His Leu Gly
                245                 250                 255

Thr Asp Ala Asp Ile Pro Phe Trp Val Lys Ala Ser Cys Ala Leu Ala
            260                 265                 270

Ile Ala Ile Gly Thr Tyr Leu Gly Gly Trp Arg Val Ile Arg Thr Leu
        275                 280                 285

Gly Lys Gly Leu Val Glu Ile Asp Ser Pro Gln Gly Met Ala Ala Glu
290                 295                 300

Thr Ser Ser Ala Ala Ile Ile Leu Thr Ser Ser His Phe Gly Met Ala
305                 310                 315                 320

Leu Ser Thr Thr His Val Ala Thr Gly Ser Ile Met Gly Thr Gly Ile
                325                 330                 335

Gly Arg Lys Gly Ala Lys Val Arg Trp Ser Val Ala Gly Arg Met Ala
            340                 345                 350

Met Ala Trp Val Ile Thr Leu Pro Ala Ser Ala Ile Val Gly Val Phe
        355                 360                 365

Cys Trp Trp Val Ala His Gly Ile Gly Leu Ile Ser Ser Asp Leu Leu
        370                 375                 380

Gly Val Leu Val Ala Phe Ala Ile Leu Val Ile Leu Ser Gly Tyr Ile
385                 390                 395                 400

Tyr Ala Arg Ser Arg Arg Val Pro Val Asp Pro Ser Asn Val Asn Ala
                405                 410                 415

Asp Trp Asn Glu Glu Ser Asn Ser Val Glu Pro Ala Thr Pro Ser Ala
            420                 425                 430

Pro Ala Ala Ser Glu Ile Ala Glu Ala Pro Ala Pro Ala Ala His
        435                 440                 445

Ala Val Gln Asp Leu Asn Asn Glu Asn Glu Val Thr Lys
450                 455                 460

<210> SEQ ID NO 7
<211> LENGTH: 20

```
<212> TYPE: DNA
<213> ORGANISM: Artificial Sequence
<220> FEATURE:
<223> OTHER INFORMATION: primer

<400> SEQUENCE: 7
cactgcacgg ccctgcgaac                                                    20

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
cgccaactag gcgccaaaaa ttcctgattt ccctaaccgg ac                            42

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgtgggcctt cggcgaggac                                                    20

<210> SEQ ID NO 10
<211> LENGTH: 42
<212> TYPE: DNA
<213> ORGANISM: Artificial Sequence
<220> FEATURE:
<223> OTHER INFORMATION: primer

<400> SEQUENCE: 10
gtccggttag ggaaatcagg aattttggc gcctagttgg cg                            42

<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
gagtcgaccg caccccattt ttcata                                             26

<210> SEQ ID NO 12
<211> LENGTH: 28
<212> TYPE: DNA
<213> ORGANISM: Artificial Sequence
<220> FEATURE:
<223> OTHER INFORMATION: primer

<400> SEQUENCE: 12
tggtcgacgt gaatgctcgg cgggatcc                                           28

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
```

```
ccaggcactc gtcctcggtt                                               20

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14
aggctagtgc aggactataa agaccagttc tcctaaaaat aacgtgtc               48

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tccatcgtgg ccaccgatcc                                               20

<210> SEQ ID NO 16
<211> LENGTH: 48
<212> TYPE: DNA
<213> ORGANISM: Artificial Sequence
<220> FEATURE:
<223> OTHER INFORMATION: primer

<400> SEQUENCE: 16
gacacgttat ttttaggaga actggtcttt atagtcctgc actagcct               48

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
cgggatcccc accggcgtac tcgtg                                         25

<210> SEQ ID NO 18
<211> LENGTH: 28
<212> TYPE: DNA
<213> ORGANISM: Artificial Sequence
<220> FEATURE:
<223> OTHER INFORMATION: primer

<400> SEQUENCE: 18
ccacggatcc ttccaatgct attggttg                                      28

<210> SEQ ID NO 19
<211> LENGTH: 45
<212> TYPE: DNA
<213> ORGANISM: Artificial Sequence
<220> FEATURE:
<223> OTHER INFORMATION: primer

<400> SEQUENCE: 19
agcttgcatg cctgcagagg aggattataa tggtcacccc aatca                  45

<210> SEQ ID NO 20
<211> LENGTH: 36
<212> TYPE: DNA
<213> ORGANISM: Artificial Sequence
```

```
<220> FEATURE:
<223> OTHER INFORMATION: primer

<400> SEQUENCE: 20
cggtacccgg ggatcctgcc cacgagggtg acctca                              36

<210> SEQ ID NO 21
<211> LENGTH: 3481
<212> TYPE: DNA
<213> ORGANISM: Corynebacterium glutamicum 2256 (ATCC 13869)
<220> FEATURE:
<221> NAME/KEY: CDS
<222> LOCATION: (1437)..(3035)

<400> SEQUENCE: 21
gatcttgccg atttcggcag gatcaatgtc ggcgtgaatg atcttggcat caggtgcgaa     60
agtgtcaacg tcaccggtga cgcggtcatc aaagcgggag ccgatagcaa tcagcaggtc    120
gctgcgctgc agtgcaccaa cagcggacac agtgccatgc atgcctggca tacccatgtg    180
cagctcgtgg gactctggga aggttcccag cgccatcaat gtggtgacaa ctggaatgcc    240
ggtgtgctca gcgaacgcac gaagctcttc gtgggcatca gccttgataa cgccgccgcc    300
aacgtaaagg acaggcttct tagactcacc gatcagtttg acagcctgct caatctgtcg    360
agcatgcggt gttgaaactg gcggtagcc  tggcaggtcg atctttggtg gccagacgaa    420
atccaattca gcgttctgaa catccttggg gatatccact agaacaggac cagggcgacc    480
agtaatcgcg aggtggaatg cctcagccaa tgcctgtgga atgtcgttgg ggttggtgac    540
catgaagttg tgcttggtca ctggcatggt gatgccgcgg atatcggctt cctggaaagc    600
atcggtaccc agcaggctac ttccgacctg gccggtgatg gcaaccatgg gaacggagtc    660
caagtttgca tcagcgattg gggtaaccaa gttggttgcg cctgggccag aggttgcaat    720
gcagacgcca acgcgtccag taacctgcgc gtagccggtt gctgcgtggc ctgcgccctg    780
ctcgtggcgc actaggacgt ggcgcacctt tgtggaggaa tagagcgggt catacaccgg    840
tagcaccgca ccaccaggaa taccgaacac gatgtcggcg ttaagctcct cgagcgatcg    900
aacaattgcc tgtgcacctg tcatccgctc aggggcggcg gatcgaccac ggcttgcaac    960
cgtggcggga gtgggctgtt gagaagctgc cacattcacg actttctggc tcctttacta   1020
aataaggatt tcacaggac  ccgtccaagc caagccgatt tcaactcagc ctaaagacaa   1080
agccctcatt taaaattgtt ccgacgcgga tgcgtgtgca cgcagtgcga cagatgtctg   1140
ttgcaaagtt ggctacttgg gtcataacca acaagaaagc cctcgttcca acactgtggt   1200
gagtgttgtc gagggcgctt gacgagacga cttggaaggc cgttacggca ggcgccgcgc   1260
ggttactact acaagtcgaa taatggtcat ggtgtgtcat gctacacaca tcgagtttcc   1320
aattccacaa cgcacgaaaa ttcccacccc caaaactccc ccacttcggt taaggaatca   1380
ggattctcac aaagttcagg caggctcccg ctactttca  gcgctaatct tggctc atg   1439
                                                                Met
                                                                  1 att tta ggc gta ccc att caa tat ttg ctc tat tca ttg tgg aat tgg     1487
Ile Leu Gly Val Pro Ile Gln Tyr Leu Leu Tyr Ser Leu Trp Asn Trp
              5                  10                  15 att gtc gat acc ggt ttt gat gta gca att atc ctg gtc ttg gcg ttt     1535
Ile Val Asp Thr Gly Phe Asp Val Ala Ile Ile Leu Val Leu Ala Phe
         20                  25                  30 ttg att cca cgt atc ggc cga ctg gcc atg cgt att atc aag cag cga     1583
Leu Ile Pro Arg Ile Gly Arg Leu Ala Met Arg Ile Ile Lys Gln Arg
     35                  40                  45
```

| | | | | | | | | | | | | | | | | |
|---|---|---|---|---|---|---|---|---|---|---|---|---|---|---|---|---|
| gtg | gag | tct | gca | gcc | gat | gcg | gac | acc | act | aag | aac | cag | ctc | gcg | ttc | 1631 |
| Val | Glu | Ser | Ala | Ala | Asp | Ala | Asp | Thr | Thr | Lys | Asn | Gln | Leu | Ala | Phe | |
| 50 | | | | | 55 | | | | | 60 | | | | | 65 | |
| gct | ggc | gtt | ggc | gtt | tat | atc | gcg | caa | att | gtg | gcg | ttt | ttc | atg | ctt | 1679 |
| Ala | Gly | Val | Gly | Val | Tyr | Ile | Ala | Gln | Ile | Val | Ala | Phe | Phe | Met | Leu | |
| | | | | 70 | | | | | 75 | | | | | 80 | | |
| gcc | gtc | tcc | gcg | atg | cag | gct | ttt | ggt | ttc | tct | ctc | gcg | ggc | gct | gcg | 1727 |
| Ala | Val | Ser | Ala | Met | Gln | Ala | Phe | Gly | Phe | Ser | Leu | Ala | Gly | Ala | Ala | |
| | | | | 85 | | | | | 90 | | | | | 95 | | |
| att | ccg | gca | acc | att | gcg | tca | gct | gcc | att | ggt | ctt | ggt | gcg | cag | tcg | 1775 |
| Ile | Pro | Ala | Thr | Ile | Ala | Ser | Ala | Ala | Ile | Gly | Leu | Gly | Ala | Gln | Ser | |
| | | 100 | | | | | 105 | | | | | 110 | | | | |
| att | gtt | gcg | gac | ttc | ttg | gcc | gga | ttt | ttc | atc | ctg | acg | gaa | aag | caa | 1823 |
| Ile | Val | Ala | Asp | Phe | Leu | Ala | Gly | Phe | Phe | Ile | Leu | Thr | Glu | Lys | Gln | |
| | | | 115 | | | | | 120 | | | | | 125 | | | |
| ttc | ggc | gtg | ggt | gac | tgg | gtg | cgc | ttt | gag | ggc | aac | ggc | atc | gtt | gtt | 1871 |
| Phe | Gly | Val | Gly | Asp | Trp | Val | Arg | Phe | Glu | Gly | Asn | Gly | Ile | Val | Val | |
| 130 | | | | | 135 | | | | | 140 | | | | | 145 | |
| gaa | ggc | acc | gtc | att | gag | atc | acc | atg | cgc | gcg | acc | aaa | att | cgc | acg | 1919 |
| Glu | Gly | Thr | Val | Ile | Glu | Ile | Thr | Met | Arg | Ala | Thr | Lys | Ile | Arg | Thr | |
| | | | | 150 | | | | | 155 | | | | | 160 | | |
| att | gca | caa | gag | acc | gtg | atc | atc | ccg | aac | tcc | acg | gcg | aaa | gtg | tgc | 1967 |
| Ile | Ala | Gln | Glu | Thr | Val | Ile | Ile | Pro | Asn | Ser | Thr | Ala | Lys | Val | Cys | |
| | | | 165 | | | | | 170 | | | | | 175 | | | |
| atc | aac | aat | tct | aat | aac | tgg | tcg | cgt | gcg | gtt | gtc | gtt | att | ccg | atc | 2015 |
| Ile | Asn | Asn | Ser | Asn | Asn | Trp | Ser | Arg | Ala | Val | Val | Val | Ile | Pro | Ile | |
| | | | 180 | | | | | 185 | | | | | 190 | | | |
| ccc | atg | ttg | ggt | tct | gaa | aac | atc | aca | gat | gtc | atc | gcg | cgc | tct | gaa | 2063 |
| Pro | Met | Leu | Gly | Ser | Glu | Asn | Ile | Thr | Asp | Val | Ile | Ala | Arg | Ser | Glu | |
| | | | 195 | | | | | 200 | | | | | 205 | | | |
| gct | gcg | act | cgt | cgc | gca | ctt | ggc | cag | gag | aaa | atc | gca | ccg | gaa | atc | 2111 |
| Ala | Ala | Thr | Arg | Arg | Ala | Leu | Gly | Gln | Glu | Lys | Ile | Ala | Pro | Glu | Ile | |
| 210 | | | | | 215 | | | | | 220 | | | | | 225 | |
| ctc | ggt | gaa | ctc | gat | gtg | cac | cca | gcc | acg | gaa | gtc | aca | ccg | cca | acg | 2159 |
| Leu | Gly | Glu | Leu | Asp | Val | His | Pro | Ala | Thr | Glu | Val | Thr | Pro | Pro | Thr | |
| | | | | 230 | | | | | 235 | | | | | 240 | | |
| gtg | gtc | ggc | atg | ccg | tgg | atg | gtc | acc | atg | cgt | ttc | ctc | gtg | caa | gtc | 2207 |
| Val | Val | Gly | Met | Pro | Trp | Met | Val | Thr | Met | Arg | Phe | Leu | Val | Gln | Val | |
| | | | | 245 | | | | | 250 | | | | | 255 | | |
| acc | gcc | ggc | aat | caa | tgg | ctg | gtc | gaa | cgc | gcc | atc | cgc | aca | gaa | atc | 2255 |
| Thr | Ala | Gly | Asn | Gln | Trp | Leu | Val | Glu | Arg | Ala | Ile | Arg | Thr | Glu | Ile | |
| | | | | 260 | | | | | 265 | | | | | 270 | | |
| atc | aac | gaa | ttc | tgg | gaa | gaa | tac | ggc | agc | gca | acc | act | aca | tcg | gga | 2303 |
| Ile | Asn | Glu | Phe | Trp | Glu | Glu | Tyr | Gly | Ser | Ala | Thr | Thr | Thr | Ser | Gly | |
| | | | | 275 | | | | | 280 | | | | | 285 | | |
| acc | ctc | att | gat | tcc | tta | cac | gtt | gag | cat | gaa | gag | cca | aag | acc | tcg | 2351 |
| Thr | Leu | Ile | Asp | Ser | Leu | His | Val | Glu | His | Glu | Glu | Pro | Lys | Thr | Ser | |
| 290 | | | | | 295 | | | | | 300 | | | | | 305 | |
| ctt | atc | gac | gcc | tcc | ccc | cag | gct | ctt | aag | gaa | ccg | aag | ccg | gag | gct | 2399 |
| Leu | Ile | Asp | Ala | Ser | Pro | Gln | Ala | Leu | Lys | Glu | Pro | Lys | Pro | Glu | Ala | |
| | | | | 310 | | | | | 315 | | | | | 320 | | |
| gcg | gcg | acg | gtt | gca | tcg | cta | gct | gca | tcg | tct | aac | gac | gat | gca | gac | 2447 |
| Ala | Ala | Thr | Val | Ala | Ser | Leu | Ala | Ala | Ser | Ser | Asn | Asp | Asp | Ala | Asp | |
| | | | | 325 | | | | | 330 | | | | | 335 | | |
| aat | gca | gac | gcc | tcg | gcg | atc | aat | gca | ggc | aat | cca | gag | aag | gaa | ctt | 2495 |
| Asn | Ala | Asp | Ala | Ser | Ala | Ile | Asn | Ala | Gly | Asn | Pro | Glu | Lys | Glu | Leu | |
| | | | | 340 | | | | | 345 | | | | | 350 | | |
| gat | tcc | gat | gtg | ctg | gaa | caa | gaa | ctc | tcc | agc | gaa | gaa | ccg | gaa | gaa | 2543 |
| Asp | Ser | Asp | Val | Leu | Glu | Gln | Glu | Leu | Ser | Ser | Glu | Glu | Pro | Glu | Glu | |

-continued

```
               355                 360                 365
aca gca aaa cca gat cac tct ctc cga ggc ttc ttc cgc act gat tac      2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc      2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt      2687
Met Ser Thr Ser Leu Leu Leu Gly Ala Leu Leu Leu Leu Ser Leu Phe
            405                 410                 415 aag gtc atg act gtg gaa cca agt gag aat tgg caa aac tcc agt gga      2735
Lys Val Met Thr Val Glu Pro Ser Glu Asn Trp Gln Asn Ser Ser Gly
        420                 425                 430 tgg ctg tca cca agc act gcc acc tca act gcg gtg acc acc tcc gaa      2783
Trp Leu Ser Pro Ser Thr Ala Thr Ser Thr Ala Val Thr Thr Ser Glu
    435                 440                 445 act tcc gcg cca gca agc acg cct tcg atg aca gtg ccc act acg gtg      2831
Thr Ser Ala Pro Ala Ser Thr Pro Ser Met Thr Val Pro Thr Thr Val
450                 455                 460                 465 gag gag acc cca acg atg gaa tct agc gtc gaa acg cag cag gaa acc      2879
Glu Glu Thr Pro Thr Met Glu Ser Ser Val Glu Thr Gln Gln Glu Thr
                470                 475                 480 tca acc cct gca acc gca acg ccc cag cga gcc gac acc atc gaa ccg      2927
Ser Thr Pro Ala Thr Ala Thr Pro Gln Arg Ala Asp Thr Ile Glu Pro
            485                 490                 495 acc gag gaa gcc acg tcg cag gag gaa acg act gca tcg cag acg cag      2975
Thr Glu Glu Ala Thr Ser Gln Glu Glu Thr Thr Ala Ser Gln Thr Gln
        500                 505                 510 tct cca gca gtg gaa gca cca acc gcg gtc caa gaa aca gtt gcg ccg      3023
Ser Pro Ala Val Glu Ala Pro Thr Ala Val Gln Glu Thr Val Ala Pro
    515                 520                 525 acg tcc acc cct taggacgctg attacagacg tgtcccattt ctttactact           3075
Thr Ser Thr Pro
530 attggaaatt atgagttcag acgcagaaaa ggcatccgtg agctttccg aaaaatttca      3135 cccagaacgc acccatattt tgggcgccgt tgttttggc ctgatctcat tattagtcat      3195 cggcgcagcc cctcagtacc tgttttggct gctcgcgctc cctgtcatct tcggttactg     3255 ggttctaaaa tcatccacga tcgttgatga acagggcatc accgcaaact acgccttcaa    3315 gggcaaaaag gttgtggcct gggaagacct cgcaggaatc ggattcaagg gtgcccgcac    3375 tttcgctcgc accacctccg atgcagaagt caccctcccc ggcgtcacct tcaactccct    3435 tccccgcctt gaagctgctt cccacggccg catccccgat gcgatc                    3481
```

<210> SEQ ID NO 22
<211> LENGTH: 533
<212> TYPE: PRT
<213> ORGANISM: Corynebacterium glutamicum 2256 (ATCC 13869)

<400> SEQUENCE: 22

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60
```

```
Phe Ala Gly Val Gly Val Tyr Ile Ala Gln Ile Val Ala Phe Phe Met
 65                  70                  75                  80

Leu Ala Val Ser Ala Met Gln Ala Phe Gly Phe Ser Leu Ala Gly Ala
                 85                  90                  95

Ala Ile Pro Ala Thr Ile Ala Ser Ala Ile Gly Leu Gly Ala Gln
            100                 105                 110

Ser Ile Val Ala Asp Phe Leu Ala Gly Phe Phe Ile Leu Thr Glu Lys
            115                 120                 125

Gln Phe Gly Val Gly Asp Trp Val Arg Phe Glu Gly Asn Gly Ile Val
            130                 135                 140

Val Glu Gly Thr Val Ile Glu Ile Thr Met Arg Ala Thr Lys Ile Arg
145                 150                 155                 160

Thr Ile Ala Gln Glu Thr Val Ile Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
            195                 200                 205

Glu Ala Ala Thr Arg Arg Ala Leu Gly Gln Glu Lys Ile Ala Pro Glu
210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
            275                 280                 285

Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
            355                 360                 365

Glu Thr Ala Lys Pro Asp His Ser Leu Arg Gly Phe Phe Arg Thr Asp
            370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Leu Ser Leu
                405                 410                 415

Phe Lys Val Met Thr Val Glu Pro Glu Asn Trp Gln Asn Ser Ser
            420                 425                 430

Gly Trp Leu Ser Pro Ser Thr Ala Thr Ser Thr Ala Val Thr Thr Ser
            435                 440                 445

Glu Thr Ser Ala Pro Ala Ser Thr Pro Ser Met Thr Val Pro Thr Thr
            450                 455                 460

Val Glu Glu Thr Pro Thr Met Glu Ser Ser Val Glu Thr Gln Gln Glu
465                 470                 475                 480
```

Thr Ser Thr Pro Ala Thr Ala Thr Pro Gln Arg Ala Asp Thr Ile Glu
            485                 490                 495

Pro Thr Glu Glu Ala Thr Ser Gln Glu Glu Thr Thr Ala Ser Gln Thr
        500                 505                 510

Gln Ser Pro Ala Val Glu Ala Pro Thr Ala Val Gln Glu Thr Val Ala
    515                 520                 525

Pro Thr Ser Thr Pro
    530

<210> SEQ ID NO 23
<211> LENGTH: 4942
<212> TYPE: DNA
<213> ORGANISM: Corynebacterium glutamicum 2256 (ATCC 13869)
<220> FEATURE:
<221> NAME/KEY: CDS
<222> LOCATION: (1437)..(2705)

<400> SEQUENCE: 23

| | |
|---|---:|
| gatcttgccg atttcggcag gatcaatgtc ggcgtgaatg atcttggcat caggtgcgaa | 60 |
| agtgtcaacg tcaccggtga cgcggtcatc aaagcgggag ccgatagcaa tcagcaggtc | 120 |
| gctgcgctgc agtgcaccaa cagcggacac agtgccatgc atgcctggca tacccatgtg | 180 |
| cagctcgtgg gactctggga aggttcccag cgccatcaat gtggtgacaa ctggaatgcc | 240 |
| ggtgtgctca gcgaacgcac gaagctcttc gtgggcatca gccttgataa cgccgccgcc | 300 |
| aacgtaaagg acaggcttct tagactcacc gatcagtttg acagcctgct caatctgtcg | 360 |
| agcatgcggt gttgaaactg gcggtagcc tggcaggtcg atctttggtg gccagacgaa | 420 |
| atccaattca gcgttctgaa catccttggg gatatccact agaacaggac cagggcgacc | 480 |
| agtaatcgcg aggtggaatg cctcagccaa tgcctgtgga atgtcgttgg ggttggtgac | 540 |
| catgaagttg tgcttggtca ctggcatggt gatgccgcgg atatcggctt cctggaaagc | 600 |
| atcggtaccc agcaggctac ttccgacctg gccggtgatg gcaaccatgg gaacggagtc | 660 |
| caagtttgca tcagcgattg gggtaaccaa gttggttgcg cctgggccag aggttgcaat | 720 |
| gcagacgcca acgcgtccag taacctgcgt gtagccggtt gctgcgtggc ctgcgccctg | 780 |
| ctcgtggcgc actaggacgt ggcgcacctt tgtggaggaa tagagcgggt catacaccgg | 840 |
| tagcaccgca ccaccaggaa taccgaacac gatgtcggcg ttaagctcct cgagcgatcg | 900 |
| aacaattgcc tgtgcacctg tcatccgctc aggggcggcg atcgaccac ggcttgcaac | 960 |
| cgtggcggga gtgggctgtt gagaagctgc cacattcacg actttctggc tcctttacta | 1020 |
| aataaggatt tcacaggac ccgtccaagc caagccgatt tcaactcagc ctaaagacaa | 1080 |
| agccctcatt taaaattgtt ccgacgcgga tgcgtgtgca cgcagtgcga cagatgtctg | 1140 |
| ttgcaaagtt ggctacttgg gtcataacca acaagaaagc cctcgttcca acactgtggt | 1200 |
| gagtgttgtc gagggcgctt gacgagacga cttggaaggc cgttacggca ggcgccgcgc | 1260 |
| ggttactact acaagtcgaa taatggtcat ggtgtgtcat gctacacaca tcgagtttcc | 1320 |
| aattccacaa cgcacgaaaa ttcccacccc caaaactccc ccacttcggt taaggaatca | 1380 |
| ggattctcac aaagttcagg caggctcccg ctactttca gcgctaatct tggctc atg | 1439 |
| | Met |
| | 1 |
| att tta ggc gta ccc att caa tat ttg ctc tat tca ttg tgg aat tgg | 1487 |
| Ile Leu Gly Val Pro Ile Gln Tyr Leu Leu Tyr Ser Leu Trp Asn Trp | |
|         5               10              15 | |
| att gtc gat acc ggt ttt gat gta gca att atc ctg gtc ttg gcg ttt | 1535 |
| Ile Val Asp Thr Gly Phe Asp Val Ala Ile Ile Leu Val Leu Ala Phe | |

```
                  20                  25                  30
ttg att cca cgt atc ggc cga ctg gcc atg cgt att atc aag cag cga      1583
Leu Ile Pro Arg Ile Gly Arg Leu Ala Met Arg Ile Ile Lys Gln Arg
    35                  40                  45 gtg gag tct gca gcc gat gcg gac acc act aag aac cag ctc gcg ttc      1631
Val Glu Ser Ala Ala Asp Ala Asp Thr Thr Lys Asn Gln Leu Ala Phe
50                  55                  60                  65 gct ggc gtt ggc gtt tat atc gcg caa att gtg gcg ttt ttc atg ctt      1679
Ala Gly Val Gly Val Tyr Ile Ala Gln Ile Val Ala Phe Phe Met Leu
                70                  75                  80 gcc gtc tcc gcg atg cag gct ttt ggt ttc tct ctc gcg ggc gct gcg      1727
Ala Val Ser Ala Met Gln Ala Phe Gly Phe Ser Leu Ala Gly Ala Ala
            85                  90                  95 att ccg gca acc att gcg tca gct gcc att ggt ctt ggt gcg cag tcg      1775
Ile Pro Ala Thr Ile Ala Ser Ala Ala Ile Gly Leu Gly Ala Gln Ser
        100                 105                 110 att gtt gcg gac ttc ttg gcc gga ttt ttc atc ctg acg gaa aag caa      1823
Ile Val Ala Asp Phe Leu Ala Gly Phe Phe Ile Leu Thr Glu Lys Gln
    115                 120                 125 ttc ggc gtg ggt gac tgg gtg cgc ttt gag ggc aac ggc atc gtt gtt      1871
Phe Gly Val Gly Asp Trp Val Arg Phe Glu Gly Asn Gly Ile Val Val
130                 135                 140                 145 gaa ggc acc gtc att gag atc acc atg cgc gcg acc aaa att cgc acg      1919
Glu Gly Thr Val Ile Glu Ile Thr Met Arg Ala Thr Lys Ile Arg Thr
                150                 155                 160 att gca caa gag acc gtg atc atc ccg aac tcc acg gcg aaa gtg tgc      1967
Ile Ala Gln Glu Thr Val Ile Ile Pro Asn Ser Thr Ala Lys Val Cys
            165                 170                 175 atc aac aat tct aat aac tgg tcg cgt gcg gtt gtc gtt att ccg atc      2015
Ile Asn Asn Ser Asn Asn Trp Ser Arg Ala Val Val Val Ile Pro Ile
        180                 185                 190 ccc atg ttg ggt tct gaa aac atc aca gat gtc atc gcg cgc tct gaa      2063
Pro Met Leu Gly Ser Glu Asn Ile Thr Asp Val Ile Ala Arg Ser Glu
    195                 200                 205 gct gcg act cgt cgc gca ctt ggc cag gag aaa atc gca ccg gaa atc      2111
Ala Ala Thr Arg Arg Ala Leu Gly Gln Glu Lys Ile Ala Pro Glu Ile
210                 215                 220                 225 ctc ggt gaa ctc gat gtg cac cca gcc acg gaa gtc aca ccg cca acg      2159
Leu Gly Glu Leu Asp Val His Pro Ala Thr Glu Val Thr Pro Pro Thr
                230                 235                 240 gtg gtc ggc atg ccg tgg atg gtc acc atg cgt ttc ctc gtg caa gtc      2207
Val Val Gly Met Pro Trp Met Val Thr Met Arg Phe Leu Val Gln Val
            245                 250                 255 acc gcc ggc aat caa tgg ctg gtc gaa cgc gcc atc cgc aca gaa atc      2255
Thr Ala Gly Asn Gln Trp Leu Val Glu Arg Ala Ile Arg Thr Glu Ile
        260                 265                 270 atc aac gaa ttc tgg gaa gaa tac ggc agc gca acc act aca tcg gga      2303
Ile Asn Glu Phe Trp Glu Glu Tyr Gly Ser Ala Thr Thr Thr Ser Gly
    275                 280                 285 acc ctc att gat tcc tta cac gtt gag cat gaa gag cca aag acc tcg      2351
Thr Leu Ile Asp Ser Leu His Val Glu His Glu Glu Pro Lys Thr Ser
290                 295                 300                 305 ctt atc gac gcc tcc ccc cag gct ctt aag gaa ccg aag ccg gag gct      2399
Leu Ile Asp Ala Ser Pro Gln Ala Leu Lys Glu Pro Lys Pro Glu Ala
                310                 315                 320 gcg gcg acg gtt gca tcg cta gct gca tcg tct aac gac gat gca gac      2447
Ala Ala Thr Val Ala Ser Leu Ala Ala Ser Ser Asn Asp Asp Ala Asp
            325                 330                 335 aat gca gac gcc tcg gcg atc aat gca ggc aat cca gag aag gaa ctt      2495
```

-continued

```
              Asn Ala Asp Ala Ser Ala Ile Asn Ala Gly Asn Pro Glu Lys Glu Leu
                  340                 345                 350 gat tcc gat gtg ctg gaa caa gaa ctc tcc agc gaa gaa ccg gaa gaa         2543
Asp Ser Asp Val Leu Glu Gln Glu Leu Ser Ser Glu Glu Pro Glu Glu
            355                 360                 365 aca gca aaa cca gat cac tct ctc cga ggc ttc ttc cgc act gat tac         2591
Thr Ala Lys Pro Asp His Ser Leu Arg Gly Phe Phe Arg Thr Asp Tyr
370                 375                 380                 385 tac cca aat cgg tgg cag aag atc ctg tcg ttt ggc gga cgt gtc cgc         2639
Tyr Pro Asn Arg Trp Gln Lys Ile Leu Ser Phe Gly Gly Arg Val Arg
                390                 395                 400 atg agc act tcc ctg ttg ttg ggt gcg ctg ctc ttg ctg tca cta ttt         2687
Met Ser Thr Ser Leu Leu Leu Gly Ala Leu Leu Leu Leu Ser Leu Phe
            405                 410                 415 aag ggg ctc ttc ctg ttt tagagtgcat tgatcttatg gaccaactgc                2735
Lys Gly Leu Phe Leu Phe
            420 cctgaatgga taaggcaccg cagaatgtag tggttcaaat tacggaaacc tagagcaatc       2795 ccacgcaaat gctccaaccg tccgttgatc gcttcgaccg gaccgttgga gacaccaaca       2855 tcgaaatacg ccaacacatc accaagtcgt ttaaacaaac tacgacccaa ctgcgcgagt       2915 tccttattcg gccccttcaa cacccgaagc tgatcaataa tggtccgcat tttcttcttc       2975 gcttcacgct tattacccat ctgataacaa tcaataatcg cctgatacgc aagccacgca       3035 agctttaaca ccccgtagtc tttgtcatac gcccacaact gctccaagct tcttgctga        3095 cgaggactca accacttgtg cgtggtcaac aaggtcttcc ggttttttata caacggatcc      3155 tggcttaaac cacgacgctg gtatttctcc cgctggaggc gttgccggca ggcggtgagc       3215 ttgtcaccag caagccgcac aacatggaat ggatccatca cgcgacgagc agaaggaatg      3275 agttctttac ttgctgtggc gtagccttgg aacccatcca tggacacgat ccgtatctga      3335 ttgcggaact gttcaccgcg ggaaccaagc caggaccgta aagcatcagc actacgacct      3395 gggacgacat ctaataaccg ggcaggacac cgtgagtcat accgatgccc ggtcatatcg      3455 acaatcacgg tgacaaaccc atcaccatgc ttagccctat tatgtgacca cttatgctca      3515 tccaccccaa tgacatacac tccatcaaga tggtgaggat cgttatagac cagctcacgg      3575 cacatatcga gggctagttg gcaggttaaa tcccaccct gcccaagtgc tttcgcggtt       3635 gcgtgaacac tcatccggtc aatagcaagg cgttgcaaaa tccagcgggt gacccggtgg      3695 gtgaccttt taccgtggtc agcgcagctt agttctgctt ggaaatactt ttgcttacat      3755 gtcgggttgg tgcagcggta gcgaggtaga cggataaaca gtttggtggg aaacccgacg     3815 atgggtaaat caatgagcat ccggtgggtg tgatgacgaa acaccccagg ttgggagcat      3875 tctgggcagg tggaggtata gtcgagtgcg tctgcttcga tcagggtgta atcacctgca      3935 tcggaagcgc cggtgatggt gagtcctagt tccgcagtgc ggcagatggt gtcagcgatg     3995 atgttgccgg tagacttcat gggtagagcc ttttgttggt gtttggttag cttagatacc      4055 taaaccttaa ccctgacaaa aggctcgttt attttcgggt ctacaccgct agcccaggtt      4115 ctgtgatgta cccaaaaacc ggaagggcca tttaaggtca tgactgtgga accaagtgag      4175 aattggcaaa actccagtgg atggctgtca ccaagcactg ccacctcaac tgcggtgacc      4235 acctccgaaa cttccgcgcc agcaagcacg ccttcgatga cagtgcccac tacggtggag      4295 gagaccccaa cgatggaatc tagcgtcgaa acgcagcagg aaacctcaac ccctgcaacc     4355 gcaacgcccc agcgagccga caccatcgaa ccgaccgagg aagccacgtc gcaggaggaa     4415
```

-continued

```
acgactgcat cgcagacgca gtctccagca gtggaagcac caaccgcggt ccaagaaaca      4475
gttgcgccga cgtccacccc ttaggacgct gattacagac gtgtcccatt tctttactac      4535
tattggaaat tatgagttca gacgcagaaa aggcatccgt ggagctttcc gaaaaatttc      4595
acccagaacg cacccatatt ttgggcgccg ttgttttgg cctgatctca ttattagtca       4655
tcggcgcagc ccctcagtac ctgttttggc tgctcgcgct ccctgtcatc ttcggttact      4715
gggttctaaa atcatccacg atcgttgatg aacagggcat caccgcaaac tacgccttca      4775
agggcaaaaa ggttgtggcc tgggaagacc tcgcaggaat cggattcaag ggtgcccgca      4835
ctttcgctcg caccacctcc gatgcagaag tcaccctccc cggcgtcacc ttcaactccc      4895
ttccccgcct tgaagctgct tcccacggcc gcatccccga tgcgatc                   4942
```

<210> SEQ ID NO 24
<211> LENGTH: 423
<212> TYPE: PRT
<213> ORGANISM: Corynebacterium glutamicum 2256 (ATCC 13869)

<400> SEQUENCE: 24

```
Met Ile Leu Gly Val Pro Ile Gln Tyr Leu Leu Tyr Ser Leu Trp Asn
1               5                   10                  15

Trp Ile Val Asp Thr Gly Phe Asp Val Ala Ile Ile Leu Val Leu Ala
            20                  25                  30

Phe Leu Ile Pro Arg Ile Gly Arg Leu Ala Met Arg Ile Ile Lys Gln
        35                  40                  45

Arg Val Glu Ser Ala Ala Asp Ala Asp Thr Thr Lys Asn Gln Leu Ala
    50                  55                  60

Phe Ala Gly Val Gly Val Tyr Ile Ala Gln Ile Val Ala Phe Phe Met
65                  70                  75                  80

Leu Ala Val Ser Ala Met Gln Ala Phe Gly Phe Ser Leu Ala Gly Ala
                85                  90                  95

Ala Ile Pro Ala Thr Ile Ala Ser Ala Ala Ile Gly Leu Gly Ala Gln
            100                 105                 110

Ser Ile Val Ala Asp Phe Leu Ala Gly Phe Phe Ile Leu Thr Glu Lys
        115                 120                 125

Gln Phe Gly Val Gly Asp Trp Val Arg Phe Glu Gly Asn Gly Ile Val
    130                 135                 140

Val Glu Gly Thr Val Ile Glu Ile Thr Met Arg Ala Thr Lys Ile Arg
145                 150                 155                 160

Thr Ile Ala Gln Glu Thr Val Ile Pro Asn Ser Thr Ala Lys Val
                165                 170                 175

Cys Ile Asn Asn Ser Asn Asn Trp Ser Arg Ala Val Val Ile Pro
            180                 185                 190

Ile Pro Met Leu Gly Ser Glu Asn Ile Thr Asp Val Ile Ala Arg Ser
        195                 200                 205

Glu Ala Ala Thr Arg Arg Ala Leu Gly Gln Glu Lys Ile Ala Pro Glu
    210                 215                 220

Ile Leu Gly Glu Leu Asp Val His Pro Ala Thr Glu Val Thr Pro Pro
225                 230                 235                 240

Thr Val Val Gly Met Pro Trp Met Val Thr Met Arg Phe Leu Val Gln
                245                 250                 255

Val Thr Ala Gly Asn Gln Trp Leu Val Glu Arg Ala Ile Arg Thr Glu
            260                 265                 270

Ile Ile Asn Glu Phe Trp Glu Glu Tyr Gly Ser Ala Thr Thr Thr Ser
        275                 280                 285
```

```
Gly Thr Leu Ile Asp Ser Leu His Val Glu His Glu Glu Pro Lys Thr
            290                 295                 300

Ser Leu Ile Asp Ala Ser Pro Gln Ala Leu Lys Glu Pro Lys Pro Glu
305                 310                 315                 320

Ala Ala Ala Thr Val Ala Ser Leu Ala Ala Ser Ser Asn Asp Asp Ala
                325                 330                 335

Asp Asn Ala Asp Ala Ser Ala Ile Asn Ala Gly Asn Pro Glu Lys Glu
            340                 345                 350

Leu Asp Ser Asp Val Leu Glu Gln Glu Leu Ser Ser Glu Glu Pro Glu
        355                 360                 365

Glu Thr Ala Lys Pro Asp His Ser Leu Arg Gly Phe Phe Arg Thr Asp
370                 375                 380

Tyr Tyr Pro Asn Arg Trp Gln Lys Ile Leu Ser Phe Gly Gly Arg Val
385                 390                 395                 400

Arg Met Ser Thr Ser Leu Leu Leu Gly Ala Leu Leu Leu Ser Leu
                405                 410                 415

Phe Lys Gly Leu Phe Leu Phe
            420

<210> SEQ ID NO 25
<211> LENGTH: 1386
<212> TYPE: DNA
<213> ORGANISM: Corynebacterium glutamicum ATCC13032
<220> FEATURE:
<221> NAME/KEY: CDS
<222> LOCATION: (1)..(1386)

<400> SEQUENCE: 25 atg gtc acc cca atc atg ggg aat tcg aac tct atc ctg ggc att tac      48
Met Val Thr Pro Ile Met Gly Asn Ser Asn Ser Ile Leu Gly Ile Tyr
1               5                   10                  15 cgt cag aaa atc caa aat cga cat ttg gtt tct acg ctt ttt agg gca      96
Arg Gln Lys Ile Gln Asn Arg His Leu Val Ser Thr Leu Phe Arg Ala
            20                  25                  30 tac ttc cca atc gtg acc gag ctg att att tta ttg att gtt atc gtg     144
Tyr Phe Pro Ile Val Thr Glu Leu Ile Ile Leu Leu Ile Val Ile Val
        35                  40                  45 acg gcg ctc gcc ttc gat ttc aca aac gga ttc cac gac acc ggc aat     192
Thr Ala Leu Ala Phe Asp Phe Thr Asn Gly Phe His Asp Thr Gly Asn
    50                  55                  60 gcg atg gcc aca tcc att gcc aca ggc gct cta aaa cct aaa gtc gcc     240
Ala Met Ala Thr Ser Ile Ala Thr Gly Ala Leu Lys Pro Lys Val Ala
65                  70                  75                  80 gtg gca cta tcc gcc tca ctg aac ctt gtt ggc gca ttc ctc tct gta     288
Val Ala Leu Ser Ala Ser Leu Asn Leu Val Gly Ala Phe Leu Ser Val
                85                  90                  95 gaa gtt gcg aca act gtt gcc aaa ggc gtt gtt gac ctc gac caa ttc     336
Glu Val Ala Thr Thr Val Ala Lys Gly Val Val Asp Leu Asp Gln Phe
            100                 105                 110 gac cta agc aat gcc tgg gat tcc cac cag ctc ctg ctt gtc gtc ttc     384
Asp Leu Ser Asn Ala Trp Asp Ser His Gln Leu Leu Leu Val Val Phe
        115                 120                 125 gcc ggc ctc att ggc gcc atc gtc tgg aac ctt ctg acc tgg ctg cta     432
Ala Gly Leu Ile Gly Ala Ile Val Trp Asn Leu Leu Thr Trp Leu Leu
    130                 135                 140 ggc att cct tcc agc tcc tct cac gca ctt ttc ggt ggc ctc att ggc     480
Gly Ile Pro Ser Ser Ser Ser His Ala Leu Phe Gly Gly Leu Ile Gly
145                 150                 155                 160
```

```
gcc gca att gct tca ctc ggt ttc ggc gga gtg gtg tgg gaa ggt gtc      528
Ala Ala Ile Ala Ser Leu Gly Phe Gly Gly Val Val Trp Glu Gly Val
            165                 170                 175 ttg tcc aag atg atc atc cca gca ttg gct gca cca gtt gtt gca ggt      576
Leu Ser Lys Met Ile Ile Pro Ala Leu Ala Ala Pro Val Val Ala Gly
            180                 185                 190 ctc gtg gcc gcc atc ggc act ttc gcc gtg tac agc atc aca aag gca      624
Leu Val Ala Ala Ile Gly Thr Phe Ala Val Tyr Ser Ile Thr Lys Ala
            195                 200                 205 gtt gga gac aac gag aag aac cgt tac ttc cgc tgg ggt cag atc ggc      672
Val Gly Asp Asn Glu Lys Asn Arg Tyr Phe Arg Trp Gly Gln Ile Gly
210                 215                 220 tcc gct tcc ttg gtt tcc ctg gca cac ggc acc aac gat gcc cag aag      720
Ser Ala Ser Leu Val Ser Leu Ala His Gly Thr Asn Asp Ala Gln Lys
225                 230                 235                 240 acc atg ggc gtt atc ttc ctt tcc ctg gtt gcc acc ggt cac ctg gga      768
Thr Met Gly Val Ile Phe Leu Ser Leu Val Ala Thr Gly His Leu Gly
            245                 250                 255 act gac gct gac atc cca ttc tgg gtc aag gct aca tgt gca ttg gca      816
Thr Asp Ala Asp Ile Pro Phe Trp Val Lys Ala Thr Cys Ala Leu Ala
            260                 265                 270 atc gca atc ggt acc tac ttg ggt ggt tgg cgc gtt atc cgc aca ctg      864
Ile Ala Ile Gly Thr Tyr Leu Gly Gly Trp Arg Val Ile Arg Thr Leu
            275                 280                 285 ggc aaa ggc ttg gtt gag att gat tcc cct cag ggc atg gca gca gaa      912
Gly Lys Gly Leu Val Glu Ile Asp Ser Pro Gln Gly Met Ala Ala Glu
290                 295                 300 act tct tct gca gca atc att ttg act tct tcc cac ttc ggt atg gca      960
Thr Ser Ser Ala Ala Ile Ile Leu Thr Ser Ser His Phe Gly Met Ala
305                 310                 315                 320 ctg tcc acc act cac gtt gct act ggc tcc atc atg ggt acc ggc att     1008
Leu Ser Thr Thr His Val Ala Thr Gly Ser Ile Met Gly Thr Gly Ile
            325                 330                 335 gga cgt aaa ggg gcg aag gtt cgt tgg tcc gtc gca gga cgc atg gca     1056
Gly Arg Lys Gly Ala Lys Val Arg Trp Ser Val Ala Gly Arg Met Ala
            340                 345                 350 atg gcc tgg gtt atc acc ctc cct gcc tcc gcg atc gtt ggc gtt ttc     1104
Met Ala Trp Val Ile Thr Leu Pro Ala Ser Ala Ile Val Gly Val Phe
            355                 360                 365 tgc tgg tgg gta gct cac gga att ggt ctt atc agc tca gac ctc ctc     1152
Cys Trp Trp Val Ala His Gly Ile Gly Leu Ile Ser Ser Asp Leu Leu
            370                 375                 380 gga gtc ctc gtt gca ttc gcc att ctg gtc att ctg tct ggc tac att     1200
Gly Val Leu Val Ala Phe Ala Ile Leu Val Ile Leu Ser Gly Tyr Ile
385                 390                 395                 400 tac gcc cgt tcc cgt cgc gtg cct gtt gat cca agc aac gtc aac gct     1248
Tyr Ala Arg Ser Arg Arg Val Pro Val Asp Pro Ser Asn Val Asn Ala
            405                 410                 415 gac tgg aat gaa gaa tca aac agc gtg gaa cct gca aca cct tcc gcc     1296
Asp Trp Asn Glu Glu Ser Asn Ser Val Glu Pro Ala Thr Pro Ser Ala
            420                 425                 430 ccg gct gct tct gag att aca gaa gct cct gcc gct cca gcc gct caa     1344
Pro Ala Ala Ser Glu Ile Thr Glu Ala Pro Ala Ala Pro Ala Ala Gln
            435                 440                 445 gcc gtt caa gat ctc aac aac gag aat gag gta acc aag taa             1386
Ala Val Gln Asp Leu Asn Asn Glu Asn Glu Val Thr Lys
            450                 455                 460

<210> SEQ ID NO 26
<211> LENGTH: 461
```

<212> TYPE: PRT
<213> ORGANISM: Corynebacterium glutamicum ATCC13032

<400> SEQUENCE: 26

```
Met Val Thr Pro Ile Met Gly Asn Ser Asn Ser Ile Leu Gly Ile Tyr
1               5                   10                  15

Arg Gln Lys Ile Gln Asn Arg His Leu Val Ser Thr Leu Phe Arg Ala
            20                  25                  30

Tyr Phe Pro Ile Val Thr Glu Leu Ile Ile Leu Leu Ile Val Ile Val
        35                  40                  45

Thr Ala Leu Ala Phe Asp Phe Thr Asn Gly Phe His Asp Thr Gly Asn
    50                  55                  60

Ala Met Ala Thr Ser Ile Ala Thr Gly Ala Leu Lys Pro Lys Val Ala
65                  70                  75                  80

Val Ala Leu Ser Ala Ser Leu Asn Leu Val Gly Ala Phe Leu Ser Val
                85                  90                  95

Glu Val Ala Thr Thr Val Ala Lys Gly Val Val Asp Leu Asp Gln Phe
            100                 105                 110

Asp Leu Ser Asn Ala Trp Asp Ser His Gln Leu Leu Leu Val Val Phe
        115                 120                 125

Ala Gly Leu Ile Gly Ala Ile Val Trp Asn Leu Leu Thr Trp Leu Leu
    130                 135                 140

Gly Ile Pro Ser Ser Ser His Ala Leu Phe Gly Gly Leu Ile Gly
145                 150                 155                 160

Ala Ala Ile Ala Ser Leu Gly Phe Gly Gly Val Val Trp Glu Gly Val
                165                 170                 175

Leu Ser Lys Met Ile Ile Pro Ala Leu Ala Ala Pro Val Val Ala Gly
            180                 185                 190

Leu Val Ala Ala Ile Gly Thr Phe Ala Val Tyr Ser Ile Thr Lys Ala
        195                 200                 205

Val Gly Asp Asn Glu Lys Asn Arg Tyr Phe Arg Trp Gly Gln Ile Gly
    210                 215                 220

Ser Ala Ser Leu Val Ser Leu Ala His Gly Thr Asn Asp Ala Gln Lys
225                 230                 235                 240

Thr Met Gly Val Ile Phe Leu Ser Leu Val Ala Thr Gly His Leu Gly
                245                 250                 255

Thr Asp Ala Asp Ile Pro Phe Trp Val Lys Ala Thr Cys Ala Leu Ala
            260                 265                 270

Ile Ala Ile Gly Thr Tyr Leu Gly Gly Trp Arg Val Ile Arg Thr Leu
        275                 280                 285

Gly Lys Gly Leu Val Glu Ile Asp Ser Pro Gln Gly Met Ala Ala Glu
    290                 295                 300

Thr Ser Ser Ala Ala Ile Leu Thr Ser His Phe Gly Met Ala
305                 310                 315                 320

Leu Ser Thr Thr His Val Ala Thr Gly Ser Ile Met Gly Thr Gly Ile
                325                 330                 335

Gly Arg Lys Gly Ala Lys Val Arg Trp Ser Val Ala Gly Arg Met Ala
            340                 345                 350

Met Ala Trp Val Ile Thr Leu Pro Ala Ser Ala Ile Val Gly Val Phe
        355                 360                 365

Cys Trp Trp Val Ala His Gly Ile Gly Leu Ile Ser Ser Asp Leu Leu
    370                 375                 380

Gly Val Leu Val Ala Phe Ala Ile Leu Val Ile Leu Ser Gly Tyr Ile
385                 390                 395                 400
```

```
Tyr Ala Arg Ser Arg Arg Val Pro Val Asp Pro Ser Asn Val Asn Ala
            405                 410                 415

Asp Trp Asn Glu Glu Ser Asn Ser Val Glu Pro Ala Thr Pro Ser Ala
        420                 425                 430

Pro Ala Ala Ser Glu Ile Thr Glu Ala Pro Ala Ala Pro Ala Ala Gln
        435                 440                 445

Ala Val Gln Asp Leu Asn Asn Glu Asn Glu Val Thr Lys
    450                 455                 460

<210> SEQ ID NO 27
<211> LENGTH: 41
<212> TYPE: DNA
<213> ORGANISM: Artificial Sequence
<220> FEATURE:
<223> OTHER INFORMATION: primer

<400> SEQUENCE: 27
gagctcggta cccggggatc catggtcacc caatcatgg g                      41

<210> SEQ ID NO 28
<211> LENGTH: 41
<212> TYPE: DNA
<213> ORGANISM: Artificial Sequence
<220> FEATURE:
<223> OTHER INFORMATION: primer

<400> SEQUENCE: 28
gccaagcttg catgcctgca gttacttggt tacctcattc t                     41
```

METHOD FOR PRODUCING L-AMINO ACID USING MICROORGANISM HAVING INCREASED PHOSPHATE TRANSPORTER ACTIVITY

This application is a continuation of, and claims priority under 35 U.S.C. §120 to, International Application No. PCT/JP2014/062752, filed May 13, 2014, and claims priority therethrough under 35 U.S.C. §119 to Japanese Patent Application No. 2013-101589, filed May 13, 2013, and Japanese Patent Application No. 2013-219274, filed Oct. 22, 2013, the entireties of which are incorporated by reference herein. Also, the Sequence Listing filed electronically herewith is hereby incorporated by reference (File name: 2015-07-10T_US-513_Seq_List; File size: 75 KB; Date recorded: Jul. 10, 2015).

BACKGROUND OF THE INVENTION

1. Field of the Invention

The present invention relates to methods for producing an L-amino acid using a coryneform bacterium. L-amino acids are industrially useful as additives for animal feeds, ingredients for seasonings, food, and drinks, as well as in amino acid infusions, and so forth.

2. Brief Description of the Related Art

L-amino acids are industrially produced by, for example, fermentation using various microorganisms having an L-amino acid-producing ability. Examples of bacterial strains useful in fermentation methods for producing L-amino acids include, for example, a wild-type microorganism (wild-type strain), an auxotrophic strain derived from a wild-type strain, a metabolic regulation mutant strain derived from a wild-type strain that is resistant to one or more various drugs, and a strain having characteristics as both an auxotrophic strain and metabolic regulation mutant strain.

Further, in recent years, microorganisms in which an L-amino acid-producing ability is improved by recombinant DNA techniques are used for the L-amino acid production. Examples of methods for improving an L-amino acid-producing ability of a microorganism include, for example, enhancing the expression of a gene coding for an L-amino acid biosynthetic enzyme (U.S. Pat. Nos. 5,168,056 and 5,776,736), and enhancing inflow of a carbon source into an L-amino acid biosynthesis system (U.S. Pat. No. 5,906,925).

*Escherichia coli* has at least two kinds of inorganic phosphate uptake systems (R. M. Harris et al., Journal of Bacteriology, September 2001, pp. 5008-5014). One is the low-affinity inorganic phosphate transporter (Pit) system, and the other is the high-affinity phosphate-specific transporter (Pst) system. Known genes encoding protein products in the Pit system include the pitA gene and the pitB gene. Known genes encoding protein products in the Pst system include the pstSCAB genes. The protein products of the pstSCAB genes form a complex to function as the Pst system. However, the relation between the activities of these phosphate transporters and L-amino acid production has not been previously reported.

SUMMARY OF THE INVENTION

Aspects of the Invention

Aspects of the present invention include the development of a novel technique for improving an L-amino acid-producing ability of a coryneform bacterium, and thereby providing a method for efficiently producing an L-amino acid.

A method is provided that results in improvement of the ability of a coryneform bacterium to produce an L-amino acid by modifying the coryneform bacterium so that the activity of a phosphate transporter is increased.

It is an aspect of the present invention to provide a method for producing an L-amino acid comprising A) culturing a coryneform bacterium having an L-amino acid-producing ability in a medium; and B) collecting the L-amino acid from the medium, wherein the bacterium has been modified so that the activity of a phosphate transporter is increased.

It is an aspect of the present invention to provide the method as described above, wherein the activity of the phosphate transporter is increased by increasing expression of a gene coding for the phosphate transporter.

It is an aspect of the present invention to provide the method as described above, wherein the gene is the pitA gene.

It is an aspect of the present invention to provide the method as described above, wherein the pitA gene is a DNA selected from the group consisting of:

(a) a DNA comprising the nucleotide sequence shown in SEQ ID NO: 5 or 25, (b) a DNA which is able to hybridize under stringent conditions with a sequence complementary to the nucleotide sequence shown in SEQ ID NO: 5 or 25, or a probe that can be prepared from said complementary sequence, and wherein said DNA encodes a protein having the phosphate transporter activity.

It is an aspect of the present invention to provide the method as described above, wherein the pitA gene encodes a protein selected from the group consisting of:

(A) a protein comprising the amino acid sequence shown in SEQ ID NO: 6 or 26, (B) a protein comprising the amino acid sequence shown in SEQ ID NO: 6 or 26, but includes one or more substitutions, deletions, insertions, or additions of one or several amino acid residues, and wherein said protein has the phosphate transporter activity.

It is an aspect of the present invention to provide the method as described above, wherein the expression of the gene is increased by a method selected from the group consisting of: i) increasing the copy number of the gene, ii) modifying an expression control sequence of the gene, and iii) combinations thereof.

It is an aspect of the present invention to provide the method as described above, wherein the activity of the phosphate transporter is increased by causing the bacterium to harbor a mutant pitA gene coding for a phosphate transporter wherein the amino acid residue at position 246 in SEQ ID NO: 6 is replaced with an amino acid residue other than a phenylalanine residue.

It is an aspect of the present invention to provide the method as described above, wherein said amino acid residue other than a phenylalanine residue is a serine residue.

It is an aspect of the present invention to provide the method as described above, wherein the bacterium is a *Corynebacterium* bacterium.

It is an aspect of the present invention to provide the method as described above, wherein the bacterium is *Corynebacterium glutamicum*.

It is an aspect of the present invention to provide the method as described above, wherein the L-amino acid is L-glutamic acid.

It is an aspect of the present invention to provide the method as described above, wherein the L-glutamic acid is monoammonium L-glutamate or monosodium L-glutamate.

It is an aspect of the present invention to provide a method for producing an L-amino acid comprising culturing a coryneform bacterium having an L-amino acid-producing ability in a medium; and collecting the L-amino acid from the medium, wherein the bacterium harbors a mutant pitA gene coding for a phosphate transporter having a mutation that the amino acid residue at position 246 in SEQ ID NO: 6 is replaced with an amino acid residue other than a phenylalanine residue.

It is an aspect of the present invention to provide the method as described above, wherein said amino acid residue other than a phenylalanine residue is a serine residue.

It is an aspect of the present invention to provide the method as described above, wherein the bacterium is a *Corynebacterium* bacterium.

It is an aspect of the present invention to provide the method as described above, wherein the bacterium is *Corynebacterium glutamicum*.

It is an aspect of the present invention to provide the method as described above, wherein the L-amino acid is L-glutamic acid.

It is an aspect of the present invention to provide the method as described above, wherein the L-glutamic acid is monoammonium L-glutamate or monosodium L-glutamate.

It is an aspect of the present invention to provide a DNA coding for a phosphate transporter wherein the amino acid residue at position 246 in SEQ ID NO: 6 is replaced with a serine residue.

It is an aspect of the present invention to provide a coryneform bacterium harboring a mutant pitA gene coding for a phosphate transporter wherein the amino acid residue at position 246 in SEQ ID NO: 6 is replaced with a serine residue.

DESCRIPTION OF THE PREFERRED EMBODIMENTS

Hereinafter, the present invention will be explained in detail.

The method of the present invention is a method for producing an L-amino acid by culturing a coryneform bacterium having an L-amino acid-producing ability in a medium, and collecting the L-amino acid from the medium, wherein the bacterium is modified so that the activity of a phosphate transporter is increased. The coryneform bacterium used for this method can also be referred to as "the bacterium of the present invention".

<1> Bacterium of the Present Invention

The bacterium is a coryneform bacterium having an L-amino acid-producing ability, which is modified so that the activity of a phosphate transporter is increased.

<1-1> Coryneform Bacterium Having L-Amino Acid-producing Ability

A "bacterium having an L-amino acid-producing ability" can refer to a bacterium having an ability to produce and cause accumulation of an objective L-amino acid in a medium or cells of the bacterium to such a degree that the L-amino acid can be collected, when the bacterium is cultured in the medium. The bacterium having an L-amino acid-producing ability may be a bacterium that can cause accumulation of an objective L-amino acid in a medium in an amount larger than that obtainable with a non-modified strain. Examples of non-modified strains can include wild-type strains and parent strains from which the bacterium is derived. The bacterium having an L-amino acid-producing ability may be a bacterium that can accumulate an objective L-amino acid in a medium in an amount of 0.5 g/L or more, or 1.0 g/L or more.

Examples of the L-amino acid can include basic amino acids such as L-lysine, L-ornithine, L-arginine, L-histidine, and L-citrulline; aliphatic amino acids such as L-isoleucine, L-alanine, L-valine, L-leucine, and glycine; amino acids which are hydroxy-monoaminocarboxylic acids such as L-threonine and L-serine; cyclic amino acids such as L-proline; aromatic amino acids such as L-phenylalanine, L-tyrosine, and L-tryptophan; sulfur-containing amino acids such as L-cysteine, L-cystine, and L-methionine; acidic amino acids such as L-glutamic acid and L-aspartic acid; and amino acids having an amide group in the side chain such as L-glutamine and L-asparagine. The bacterium can have an ability to produce two or more kinds of amino acids.

The amino acid can be an L-amino acid, unless otherwise stated. The L-amino acid may be a free compound, a salt thereof, or a mixture thereof. That is, in the present invention, the term "L-amino acid" may mean an L-amino acid in a free form, a salt thereof, or a mixture thereof. Examples of the salt include, for example, sulfate, hydrochloride, carbonate, ammonium salt, sodium salt, and potassium salt. L-lysine may be, for example, L-lysine in a free form, the hydrochloride salt of L-lysine, the carbonate salt of L-lysine, or a mixture thereof. Further, L-glutamic acid may be, for example, L-glutamic acid in a free form, monosodium glutamate (MSG), monoammonium glutamate, or a mixture thereof.

Examples of the coryneform bacterium can include bacteria belonging to the genus *Corynebacterium, Brevibacterium, Microbacterium* bacteria, or the like.

Specific examples of the coryneform bacteria can include the following species:

*Corynebacterium acetoacidophilum*
*Corynebacterium acetoglutamicum*
*Corynebacterium alkanolyticum*
*Corynebacterium callunae*
*Corynebacterium glutamicum*
*Corynebacterium lilium*
*Corynebacterium melassecola*
*Corynebacterium thermoaminogenes (Corynebacterium efficiens)*
*Corynebacterium herculis*
*Brevibacterium divaricatum (Corynebacterium glutamicum)*
*Brevibacterium flavum (Corynebacterium glutamicum)*
*Brevibacterium immariophilum*
*Brevibacterium lactofermentum (Corynebacterium glutamicum)*
*Brevibacterium roseum*
*Brevibacterium saccharolyticum*
*Brevibacterium thiogenitalis*
*Corynebacterium ammoniagenes (Corynebacterium stationis)*
*Brevibacterium album*
*Brevibacterium cerinum*
*Microbacterium ammoniaphilum*

Specific examples of the coryneform bacteria can include the following strains:

*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium glutamicum* ATCC 13020, ATCC 13032, ATCC 13060, ATCC 13869, FERM BP-734

*Corynebacterium lilium* ATCC 15990
*Corynebacterium melassecola* ATCC 17965
*Corynebacterium efficiens* (*Corynebacterium thermoaminogenes*) AJ12340 (FERM BP-1539)
*Corynebacterium herculis* ATCC 13868
*Corynebacterium glutamicum* (*Brevibacterium divaricatum*) ATCC 14020
*Corynebacterium glutamicum* (*Brevibacterium flavum*) ATCC 13826, ATCC 14067, AJ12418 (FERM BP-2205)
*Brevibacterium immariophilum* ATCC 14068
*Corynebacterium glutamicum* (*Brevibacterium lactofermentum*) ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes* (*Corynebacterium stationis*) ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria can include bacteria which were previously classified into the genus *Brevibacterium*, but are currently united into the genus *Corynebacterium* (Int. J. Syst. Bacteriol., 41, 255 (1991)). Moreover, *Corynebacterium stationis* can include bacteria that have previously been classified into *Corynebacterium ammoniagenes*, but are presently re-classified into *Corynebacterium stationis* on the basis of nucleotide sequence analysis of 16S rRNA etc. (Int. J. Syst. Evol. Microbiol., 60, 874-879 (2010)).

These strains are available from, for example, the American Type Culture Collection (Address: P.O. Box 1549, Manassas, Va. 20108, United States of America). That is, registration numbers are assigned to the respective strains, and the strains can be ordered by using these registration numbers (refer to atcc.org/). The registration numbers of the strains are listed in the catalogue of the American Type Culture Collection.

The bacterium can inherently be able to produce an L-amino acid, or may be a bacterium that has been modified so that it has an L-amino acid-producing ability. The bacterium having an L-amino acid-producing ability can be obtained by imparting an L-amino acid-producing ability to such a bacterium as mentioned above, or by enhancing an L-amino acid-producing ability of such a bacterium as mentioned above.

To impart or enhance an L-amino acid-producing ability, methods conventionally employed in the breeding of amino acid-producing strains of coryneform bacteria, *Escherichia* bacteria, and so forth (see "Amino Acid Fermentation", Gakkai Shuppan Center (Ltd.), 1st Edition, published May 30, 1986, pp. 77-100) can be used. Examples of such methods can include, for example, acquiring an auxotrophic mutant strain, acquiring an L-amino acid analogue-resistant strain, acquiring a metabolic regulation mutant strain, and constructing a recombinant strain in which the activity of an L-amino acid biosynthetic enzyme is enhanced. In the breeding of L-amino acid-producing bacteria, one of the above-described properties such as auxotrophy, analogue resistance, and metabolic regulation mutation may be imparted alone, or two or three or more of such properties may be imparted in combination. The activity of an L-amino acid biosynthetic enzyme may be enhanced alone, or the activities of two or three or more of such enzymes may be enhanced in combination. Furthermore, imparting property(s) such as auxotrophy, analogue resistance, and metabolic regulation mutation can be combined with enhancing the activity(s) of biosynthetic enzyme(s).

An auxotrophic mutant strain, L-amino acid analogue-resistant strain, or metabolic regulation mutant strain having an L-amino acid-producing ability can be obtained by subjecting a parent strain or wild-type strain to a common mutagenesis treatment, and then selecting a strain exhibiting autotrophy, analogue resistance, or a metabolic regulation mutation, and having an L-amino acid-producing ability from the obtained mutant strains. Examples of common mutagenesis treatments can include irradiation of X-ray or ultraviolet and a treatment with a mutation agent such as N-methyl-N'-nitro-N-nitrosoguanidine (MNNG), ethyl methanesulfonate (EMS), and methyl methanesulfonate (MMS).

An L-amino acid-producing ability can also be imparted or enhanced by enhancing the activity of an enzyme involved in biosynthesis of an objective L-amino acid. An enzyme activity can be enhanced by, for example, modifying a bacterium so that the expression of a gene coding for the enzyme is enhanced. Methods for enhancing gene expression are described in WO00/18935, EP 1010755 A, and so forth. Exemplary procedures for enhancing enzyme activity are described herein.

Further, an L-amino acid-producing ability can also be imparted or enhanced by reducing the activity of an enzyme that catalyzes a reaction branching away from the biosynthetic pathway of an objective L-amino acid to generate a compound other than the objective L-amino acid. The "enzyme that catalyzes a reaction branching away from the biosynthetic pathway of an objective L-amino acid to generate a compound other than the objective L-amino acid" can include an enzyme involved in decomposition of the objective amino acid. An exemplary method for reducing an enzyme activity is described herein.

Hereafter, L-amino acid-producing bacteria and methods for imparting or enhancing an L-amino acid-producing ability will be specifically exemplified. All of the properties of the L-amino acid-producing bacteria and modifications for imparting or enhancing an L-amino acid-producing ability may be used independently or in any appropriate combination.

<L-Glutamic Acid-producing Bacteria>

Examples of L-glutamic acid-producing bacteria and parent strains which can be used to derive such bacteria can include strains in which the activity or activities of one or more kinds of the L-glutamic acid biosynthetic enzymes are enhanced. Examples of such enzymes can include, but are not particularly limited to, glutamate dehydrogenase (gdhA), glutamine synthetase (glnA), glutamate synthetase (gltBD), isocitrate dehydrogenase (icdA), aconitate hydratase (acnA, acnB), citrate synthase (gltA), methylcitrate synthase (prpC), phosphoenolpyruvate carboxylase (ppc), pyruvate dehydrogenase (aceEF, lpdA), pyruvate kinase (pykA, pykF), phosphoenolpyruvate synthase (ppsA), enolase (eno), phosphoglyceromutase (pgmA, pgmI), phosphoglycerate kinase (pgk), glyceraldehyde-3-phophate dehydrogenase (gapA), triose phosphate isomerase (tpiA), fructose bisphosphate aldolase (fbp), phosphofructokinase (pfkA, pfkB), glucose phosphate isomerase (pgi), 6-phosphogluconate dehydratase (edd), 2-keto-3-deoxy-6-phosphogluconate aldolase (eda), and transhydrogenase. Shown in the parentheses after the names of the enzymes are the names of the genes encoding the enzymes (the same shall apply throughout this specification). It is exemplary to enhance the activity or activities of one or more kinds of enzymes such as, for example, glutamate dehydrogenase, citrate synthase, phosphoenol pyruvate carboxylase, and methylcitrate synthase.

Examples of coryneform bacteria modified so that expression of the glutamate synthetase gene (gltBD) is increased include those disclosed in WO99/07853.

Further, examples of L-glutamic acid-producing bacteria and parent strains which can be used to derive such bacteria can also include strains in which the activity or activities of one or more kinds of enzymes that catalyze a reaction branching away from the biosynthesis pathway of L-glutamic acid to generate a compound other than L-glutamic acid are reduced or eliminated. Examples of such enzymes can include, but are not particularly limited to, isocitrate lyase (aceA), α-ketoglutarate dehydrogenase (sucA, odhA), phosphotransacetylase (pta), acetate kinase (ack), acetohydroxy acid synthase (ilvG), acetolactate synthase (ilvI), formate acetyltransferase (pfl), lactate dehydrogenase (ldh), glutamate decarboxylase (gadAB), succinate dehydrogenase (sdhABCD), and 1-pyroline-5-carboxylate dehydrogenase (putA).

Coryneform bacteria in which the α-ketoglutarate dehydrogenase activity is reduced or eliminated, and methods for obtaining such bacteria are disclosed in WO2008/075483. Specific examples of coryneform bacteria in which the α-ketoglutarate dehydrogenase activity is reduced or eliminated can include, for example, the following strains:

*Corynebacterium glutamicum* (*Brevibacterium lactofermentum*) L30-2 strain (Japanese Patent Laid-open (Kokai) No. 2006-340603)

*Corynebacterium glutamicum* (*Brevibacterium lactofermentum*) Δ S strain (WO95/34672)

*Corynebacterium glutamicum* (*Brevibacterium lactofermentum*) AJ12821 (FERM BP-4172, French Patent No. 9401748)

*Corynebacterium glutamicum* (*Brevibacterium flavum*) AJ12822 (FERM BP-4173, French Patent No. 9401748)

*Corynebacterium glutamicum* AJ12823 (FERM BP-4174, French Patent No. 9401748)

*Corynebacterium glutamicum* L30-2 strain (Japanese Patent Laid-open (Kokai) No. 2006-340603)

Examples of L-glutamic acid-producing bacteria and parent strains which can be used to derive such bacteria can also include strains in which both the α-ketoglutarate dehydrogenase (sucA) activity and the succinate dehydrogenase (sdh) activity are reduced or eliminated (Japanese Patent Laid-open (Kokai) No. 2010-041920). Specific examples of such strains can include, for example,

*Corynebacterium glutamicum* 8L3G Δ SDH strain, which is the odhAsdhA double-deficient strain of *Corynebacterium glutamicum* ATCC 14067 (Japanese Patent Laid-open (Kokai) No. 2010-041920).

Examples of L-glutamic acid-producing bacteria and parent strains which can be used to derive such bacteria can also include strains which are modified so that the D-xylulose-5-phosphate phosphoketolase activity and/or the fructose-6-phosphate phosphoketolase activity are/is enhanced (Japanese Patent Laid-open (Kohyo) No. 2008-509661). Either the D-xylulose-5-phosphate phosphoketolase activity or the fructose-6-phosphate phosphoketolase activity may be enhanced, or both may be enhanced. In this specification, D-xylulose-5-phosphate phosphoketolase and fructose-6-phosphate phosphoketolase may be collectively referred to as phosphoketolase.

The D-xylulose-5-phosphate phosphoketolase activity can mean an activity for converting xylulose-5-phosphate into glycelaldehyde-3-phosphate and acetyl phosphate by consuming phosphoric acid to release one molecule of $H_2O$. This activity can be measured by the method described by Goldberg, M. et al. (Methods Enzymol., 9, 515-520, 1996) or the method described by L. Meile (J. Bacteriol., 183: 2929-2936, 2001).

The fructose-6-phosphate phosphoketolase activity can mean an activity for converting fructose-6-phosphate into erythrose-4-phosphate and acetyl phosphate by consuming phosphoric acid to release one molecule of $H_2O$. This activity can be measured by the method described by Racker, E. (Methods Enzymol., 5, 276-280, 1962) or the method described by L. Meile (J. Bacteriol., 183:2929-2936, 2001).

Furthermore, examples of methods for imparting or enhancing L-glutamic acid-producing ability to or in coryneform bacteria can also include methods of imparting resistance to an organic acid analogue, respiratory inhibitor, or the like, and methods of imparting sensitivity to a cell wall synthesis inhibitor. Examples of such methods include, for example, imparting monofluoroacetic acid resistance (Japanese Patent Laid-open (Kokai) No. 50-113209), adenine resistance or thymine resistance (Japanese Patent Laid-open (Kokai) No. 57-065198); attenuating the urease activity (Japanese Patent Laid-open (Kokai) No. 52-038088); imparting malonic acid resistance (Japanese Patent Laid-open (Kokai) No. 52-038088), resistance to benzopyrones or naphthoquinones (Japanese Patent Laid-open (Kokai) No. 56-1889), HOQNO resistance (Japanese Patent Laid-open (Kokai) No. 56-140895), α-ketomalonic acid resistance (Japanese Patent Laid-open (Kokai) No. 57-2689), guanidine resistance (Japanese Patent Laid-open (Kokai) No. 56-35981), and sensitivity to penicillin (Japanese Patent Laid-open (Kokai) No. 4-88994).

Specific examples of such resistant or sensitive bacteria can include the following strains:

*Corynebacterium glutamicum* (*Brevibacterium flavum*) AJ3949 (FERM BP-2632, refer to Japanese Patent Laid-open (Kokai) No. 50-113209)

*Corynebacterium glutamicum* AJ11628 (FERM P-5736, refer to Japanese Patent Laid-open (Kokai) No. 57-065198)

*Corynebacterium glutamicum* (*Brevibacterium flavum*) AJ11355 (FERM P-5007, refer to Japanese Patent Laid-open (Kokai) No. 56-1889)

*Corynebacterium glutamicum* AJ11368 (FERM P-5020, refer to Japanese Patent Laid-open (Kokai) No. 56-1889)

*Corynebacterium glutamicum* (*Brevibacterium flavum*) AJ11217 (FERM P-4318, refer to Japanese Patent Laid-open (Kokai) No. 57-2689)

*Corynebacterium glutamicum* AJ11218 (FERM P-4319, refer to Japanese Patent Laid-open (Kokai) No. 57-2689)

*Corynebacterium glutamicum* (*Brevibacterium flavum*) AJ11564 (FERM BP-5472, refer to Japanese Patent Laid-open (Kokai) No. 56-140895)

*Corynebacterium glutamicum* (*Brevibacterium flavum*) AJ11439 (FERM BP-5136, refer to Japanese Patent Laid-open (Kokai) No. 56-35981)

*Corynebacterium glutamicum* H7684 (FERM BP-3004, refer to Japanese Patent Laid-open (Kokai) No. 04-88994)

*Corynebacterium glutamicum* (*Brevibacterium lactofermentum*) AJ11426 (FERM P-5123, refer to Japanese Patent Laid-open (Kokai) No. 56-048890)

*Corynebacterium glutamicum* AJ11440 (FERM P-5137, refer to Japanese Patent Laid-open (Kokai) No. 56-048890)

*Corynebacterium glutamicum* (*Brevibacterium lactofermentum*) AJ11796 (FERM P-6402, refer to Japanese Patent Laid-open (Kokai) No. 58-158192)

Furthermore, examples of methods for imparting or enhancing L-glutamic acid-producing ability to or in coryneform bacteria can also include a method of enhancing expression of the yggB gene and a method of introducing a mutant yggB gene having a mutation in the coding region (WO2006/070944). The yggB gene is a gene coding for a mechanosensitive channel. The yggB gene of the *Corynebacterium glutamicum* ATCC 13032 strain corresponds to the sequence complementary to the sequence of the nucleotide numbers 1,336,091 to 1,337,692 in the genome sequence registered as Genbank Accession No. NC_003450 in the NCBI database, and is also called NCgl1221. The YggB protein is registered as GenBank accession No. NP_600492. The nucleotide sequence of the yggB gene of *Corynebacterium glutamicum* 2256 (ATCC 13869) and the amino acid sequence of the YggB protein encoded by the gene are shown in SEQ ID NOS: 21 and 22, respectively.

Examples of the mutant yggB gene that can be used in the methods described herein can include yggB genes having the following mutation(s). The YggB protein encoded by a mutant yggB gene can also be referred to as a mutant YggB protein. A yggB gene not having such mutation(s) and the YggB protein encoded by the gene can also be referred to as a wild-type yggB gene and wild-type YggB protein, respectively. Examples of the wild-type YggB protein can include, for example, a protein having the amino acid sequence shown in SEQ ID NO: 22.

Mutation on C-terminal Side

The mutation on the C-terminal side is a mutation introduced into the nucleotide sequence in the region coding for the sequence of amino acid numbers 419 to 533 in SEQ ID NO: 22. Although the mutation on the C-terminal side is not particularly limited so long as the mutation is introduced into at least a part of the nucleotide sequence of the aforementioned region, the mutation on the C-terminal side can be the insertion of an insertion sequence (henceforth also referred to as "IS") or a transposon. The mutation on the C-terminal side may be any mutation which enables introduction of an amino acid substitution (missense mutation), a mutation for introducing frame shift mutation induced by insertion of the aforementioned IS or the like, and a mutation for introducing nonsense mutation. Specific examples of the mutant yggB gene having a mutation on the C-terminal side can include, for example, a yggB gene wherein an IS is inserted at position 419 in SEQ ID NO: 22, usually a valine residue, and thereby coding for a mutant YggB protein of 423 amino residues in full length, which is shorter than the wild-type YggB protein (SEQ ID NO: 22) (Japanese Patent Laid-open (Kokai) No. 2007-222163). The nucleotide sequence of this mutant yggB gene (V419::IS) and the amino acid sequence of the mutant YggB protein encoded by this gene are shown in SEQ ID NOS: 23 and 24, respectively. Examples of the mutation on the C-terminal side also include a mutation wherein the proline residue present in the region of amino acid numbers 419 to 533 in SEQ ID NO: 22 is replaced with another amino acid residue.

(2) Mutation in Transmembrane Region

It is estimated that the YggB protein encoded by the yggB gene has five transmembrane regions. In the amino acid sequence of the wild-type YggB protein of SEQ ID NO: 22, the transmembrane regions correspond to amino acid numbers 1 to 23 (first transmembrane region), 25 to 47 (second transmembrane region), 62 to 84 (third transmembrane region), 86 to 108 (fourth transmembrane region), and 110 to 132 (fifth transmembrane region). The yggB gene may have a mutation in any of these transmembrane regions. The mutation in the transmembrane region can be a substitution, deletion, addition, insertion, or inversion of one or several amino acid residues, while not inducing a frame shift mutation or nonsense mutation. Examples of the mutation in the transmembrane region can include a mutation in which one or several amino acid residues is/are inserted between the leucine residue at position 14 and the tryptophan residue at position 15, a mutation in which the alanine residue at position 100 is replaced with another amino acid residue, and a mutation in which the alanine residue at position 111 is replaced with another amino acid residue, in the amino acid sequence shown in SEQ ID NO: 22, and so forth. The number of "one or several" can be, specifically, 1 to 20, 1 to 10, 1 to 5, or 1 to 3.

When the wild-type YggB protein has an amino acid sequence other than the amino acid sequence shown in SEQ ID NO: 22, the mutations as described above may exist in the same or similar positions relative to the amino acid sequence in SEQ ID NO: 22. These positions can be determined by aligning the amino acid sequence of the objective wild-type YggB protein and the amino acid sequence of SEQ ID NO: 22. To variants of such a mutant yggB gene and mutant YggB protein, the descriptions for variants of the mutant phosphate transporter and the gene coding for it mentioned later can be applied, mutatis mutandis. The "amino acid number X in SEQ ID NO: 22" may be read as the "position X in SEQ ID NO: 22".

<L-Glutamine-producing Bacteria>

Examples of the method for imparting or enhancing L-glutamine-producing ability can include, for example, a method of modifying a bacterium so that the activity or activities of one or more of the L-glutamine biosynthesis enzymes are enhanced. Examples of such enzymes can include, but are not particularly limited to, glutamate dehydrogenase (gdhA) and glutamine synthetase (glnA).

Examples of the method for imparting or enhancing L-glutamine-producing ability can also include, for example, a method of modifying a bacterium so that the activity or activities of one or more kinds of enzymes that catalyze a reaction branching away from the biosynthesis pathway of L-glutamine to generate a compound other than L-glutamine are reduced. Examples of such enzymes can include, but are not particularly limited to, glutaminase.

Examples of L-glutamine-producing bacteria and parent strains which can be used to derive such bacteria can include coryneform bacteria in which the activity or activities of glutamate dehydrogenase (gdhA) and/or glutamine synthetase (glnA) (EP 1229121, EP 1424398) are enhanced, and coryneform bacteria in which the glutaminase activity (Japanese Patent Laid-open (Kokai) No. 2004-187684) is reduced. The glutamine synthetase activity can also be enhanced by disruption of the glutamine adenylyltransferase gene (glnE) or disruption of the PII control protein gene (glnB) (EP 1229121).

Examples of the methods for imparting or enhancing L-glutamine-producing ability to or in coryneform bacteria can also include by imparting 6-diazo-5-oxo-norleucine resistance (Japanese Patent Laid-open (Kokai) No. 3-232497), imparting purine analogue resistance and methionine sulfoxide resistance (Japanese Patent Laid-open (Kokai) No. 61-202694), and imparting α-ketomalonic acid resistance (Japanese Patent Laid-open (Kokai) No. 56-151495). Specific examples of coryneform bacteria having L-glutamine-producing ability can include, for example, the following strains:

*Corynebacterium glutamicum* (*Brevibacterium flavum*) AJ11573 (FERM P-5492, Japanese Patent Laid-open (Kokai) No. 56-151495)

*Corynebacterium glutamicum* (*Brevibacterium flavum*) AJ11576 (FERM BP-10381, Japanese Patent Laid-open (Kokai) No. 56-151495)

*Corynebacterium glutamicum* (*Brevibacterium flavum*) AJ12212 (FERM P-8123, Japanese Patent Laid-open (Kokai) No. 61-202694)

<L-Proline-producing Bacteria>

Examples of L-proline-producing bacteria and parent strains which can be used to derive such bacteria can include strains in which the activity or activities of one or more of the L-proline biosynthetic enzymes are enhanced. Examples of the enzymes involved in L-proline biosynthesis can include glutamate-5-kinase, γ-glutamylphosphate reductase, and pyroline-5-carboxylate reductase. For enhancing such an enzymatic activity, for example, the proB gene coding for glutamate kinase desensitized to feedback inhibition by L-proline (German Patent No. 3127361) can be preferably used.

Examples of L-proline-producing bacteria and parent strains which can be used to derive such bacteria can also include strains in which the activity of an enzyme involved in decomposition of L-proline is reduced. Examples of such an enzyme include proline dehydrogenase and ornithine aminotransferase.

<L-Threonine-producing Bacteria>

Examples of L-threonine-producing bacteria and parent strains which can be used to derive such bacteria can include strains in which the activity or activities of one or more of the L-threonine biosynthetic enzymes are enhanced. Examples of such enzymes can include, but are not particularly limited to, aspartokinase III (lysC), aspartate semialdehyde dehydrogenase (asd), aspartokinase I (thrA), homoserine kinase (thrB), threonine synthase (thrC), and aspartate aminotransferase (aspartate transaminase) (aspC). It is exemplary to enhance activity or activities of one or more enzymes such as aspartokinase III, aspartate semialdehyde dehydrogenase, aspartokinase I, homoserine kinase, aspartate aminotransferase, and threonine synthase. Any of the genes coding for the L-threonine biosynthetic enzymes can be introduced into a strain in which threonine decomposition is reduced.

The activities of the L-threonine biosynthetic enzymes can be inhibited by the endproduct, L-threonine. Therefore, for construction of L-threonine-producing strains, it is exemplary to modify genes encoding the L-threonine biosynthetic enzymes so that the enzymes are desensitized to feedback inhibition by L-threonine. The aforementioned thrA, thrB, and thrC genes constitute the threonine operon, which forms an attenuator structure. The expression of the threonine operon is inhibited by isoleucine and threonine in the culture medium and also suppressed by attenuation. Therefore, the expression of the threonine operon can be enhanced by removing the leader sequence or attenuator in the attenuation region (refer to Lynn, S. P., Burton, W. S., Donohue, T. J., Gould, R. M., Gumport, R. L, and Gardner, J. F., J. Mol. Biol. 194:59-69 (1987); WO02/26993; WO2005/049808; WO2003/097839).

The native promoter of the threonine operon is present upstream of the threonine operon, but it may be replaced with a non-native promoter (refer to WO98/04715). The threonine operon may be constructed so that the threonine biosynthesis genes are expressed under control of the repressor and promoter of λ-phage (EP 0593792 B). Furthermore, a bacterium modified so that it is desensitized to feedback inhibition by L-threonine can also be obtained by selecting a strain resistant to α-amino-β-hydroxyisovaleric acid (AHV), which is an L-threonine analogue.

It is exemplary that the expression amount of the threonine operon that is modified so as to be desensitized to feedback inhibition by L-threonine as described above is increased in a host by increasing the copy number thereof or by ligating it to a potent promoter. The copy number can be increased by introducing a plasmid containing the threonine operon into a host. The copy number can also be increased by transferring the threonine operon to the genome of a host using a transposon, Mu-phage, or the like.

The thrA gene coding for aspartokinase homoserine dehydrogenase I of *E. coli* has been elucidated (nucleotide numbers 337 to 2799, GenBank accession NC_000913.2, gi: 49175990). The thrA gene is located between the thrL and thrB genes on the chromosome of *E. coli* K-12. The thrB gene coding for homoserine kinase of *Escherichia coli* has been elucidated (nucleotide numbers 2801 to 3733, GenBank accession NC 000913.2, gi: 49175990). The thrB gene is located between the thrA and thrC genes on the chromosome of *E. coli* K-12. The thrC gene coding for threonine synthase of *E. coli* has been elucidated (nucleotide numbers 3734 to 5020, GenBank accession NC 000913.2, gi: 49175990). The thrC gene is located between the thrB gene and the yaaX open reading frame on the chromosome of *E. coli* K-12. The thrA*BC operon containing a mutant thrA gene coding for aspartokinase homoserine dehydrogenase I resistant to feedback inhibition by threonine and wild-type thrBC genes can be obtained from the well-known pVIC40 plasmid, which is present in the threonine-producing *E. coli* strain VKPM B-3996 (U.S. Pat. No. 5,705,371).

The rhtA gene of *E. coli* is present at 18 min on the *E. coli* chromosome close to the glnHPQ operon, which encodes components of the glutamine transport system. The rhtA gene is identical to ORF1 (ybiF gene, nucleotide numbers 764 to 1651, GenBank accession number AAA218541, gi:440181), and is located between the pexB and ompX genes. The unit that expresses the protein encoded by the ORP1 is referred to as rhtA gene (rht: resistant to homoserine and threonine). It was also revealed that the rhtA23 mutation, which imparts resistance against a high concentration of threonine or homoserine, is an A-for-G substitution at position −1 with respect to the ATG start codon (ABSTRACTS of the 17th International Congress of Biochemistry and Molecular Biology in conjugation with Annual Meeting of the American Society for Biochemistry and Molecular Biology, San Francisco, Calif. Aug. 24-29, 1997, Abstract No. 457, EP 1013765 A).

The asd gene of *E. coli* has already been elucidated (nucleotide numbers 3572511 to 3571408, GenBank accession NC_000913.1, gi:16131307), and can be obtained by PCR (refer to White, T. J. et al., Trends Genet, 5, 185 (1989)) utilizing primers prepared on the basis of the nucleotide sequence of the gene. The asd genes of other microorganisms can also be obtained in a similar manner.

The aspC gene of *E. coli* has also already been elucidated (nucleotide numbers 983742 to 984932, GenBank accession NC 000913.1, gi:16128895), and can be obtained by PCR utilizing primers prepared on the basis of the nucleotide sequence of the gene. The aspC genes of other microorganisms can also be obtained in a similar manner.

Further, examples of coryneform bacteria having L-threonine-producing ability can include, for example, *Corynebacterium acetoacidophilum* AJ12318 (FERM BP-1172, refer to U.S. Pat. No. 5,188,949).

<L-Lysine-producing Bacteria>

Examples of L-lysine-producing bacteria and parent strains which can be used to derive such bacteria can include strains in which the activity or activities of one or more of the L-lysine biosynthetic enzymes are enhanced. Examples of such enzymes can include, but are not particularly limited to, dihydrodipicolinate synthase (dapA), aspartokinase III (lysC), dihydrodipicolinate reductase (dapB), diaminopimelate decarboxylase (lysA), diaminopimelate dehydrogenase (ddh) (U.S. Pat. No. 6,040,160), phosphoenolpyruvate carboxylase (ppc), aspartate semialdehyde dehydrogenase (asd), aspartate aminotransferase (aspartate transaminase) (aspC), diaminopimelate epimerase (dapF), tetrahydrodipicolinate succinylase (dapD), succinyl diaminopimelate deacylase (dapE), and aspartase (aspA) (EP 1253195 A). It is exemplary to enhance the activity or activities of one or more of these enzymes such as, for example, dihydrodipicolinate reductase, diaminopimelate decarboxylase, diaminopimelate dehydrogenase, phosphoenolpyruvate carboxylase, aspartate aminotransferase, diaminopimelate epimerase, aspartate semialdehyde dehydrogenase, tetrahydrodipicolinate succinylase, and succinyl diaminopimelate deacylase. In addition, L-lysine-producing bacteria and parent strains which can be used to derive such bacteria may express an increased level of the gene involved in energy efficiency (cyo) (EP 1170376 A), the gene encoding nicotinamide nucleotide transhydrogenase (pntAB) (U.S. Pat. No. 5,830,716), the ybjE gene (WO2005/073390), or a combination of these. Since aspartokinase III (lysC) is subject to feedback inhibition by L-lysine, a mutant lysC gene coding for an aspartokinase III desensitized to feedback inhibition by L-lysine (U.S. Pat. No. 5,932,453) may be used for enhancing the activity of this enzyme. Further, since dihydrodipicolinate synthase (dapA) is subject to feedback inhibition by L-lysine, a mutant dapA gene coding for a dihydrodipicolinate synthase desensitized to feedback inhibition by L-lysine may be used for enhancing the activity of this enzyme.

Examples of L-lysine-producing bacteria and parent strains which can be used to derive such bacteria can also include strains in which the activity or activities of one or more enzymes that catalyze a reaction branching away from the biosynthetic pathway of L-lysine to generate a compound other than L-lysine are reduced or eliminated. Examples of such enzymes can include, but are not particularly limited to, homoserine dehydrogenase, lysine decarboxylase (U.S. Pat. No. 5,827,698), and the malic enzyme (WO2005/010175).

Examples of L-lysine-producing bacteria and parent strains which can be used to derive such bacteria can also include mutant strains having resistance to an L-lysine analogue. L-lysine analogues inhibit the growth of bacteria such as bacteria of the family Enterobacteriaceae and coryneform bacteria, but this inhibition is fully or partially released when L-lysine is present in the medium. Examples of these L-lysine analogues can include, but are not particularly limited to, oxalysine, lysine hydroxamate, S-(2-aminoethyl)-L-cysteine (AEC), γ-methyllysine, and α-chlorocaprolactam. Mutant strains having resistance to these lysine analogues can be obtained by subjecting a bacterium to a conventional artificial mutagenesis treatment.

Specific examples of coryneform bacteria having L-lysine-producing ability can include, for example, the AEC-resistant mutant strains (*Corynebacterium glutamicum* (*Brevibacterium lactofermentum* AJ11082) (NRRL B-11470) strain etc., refer to Japanese Patent Publication (Kokoku) Nos. 56-1914, 56-1915, 57-14157, 57-14158, 57-30474, 58-10075, 59-4993, 61-35840, 62-24074, 62-36673, 5-11958, 7-112437 and 7-112438); mutant strains requiring an amino acid such as L-homoserine for their growth (refer to Japanese Patent Publication Nos. 48-28078 and 56-6499); mutant strains showing resistance to AEC and further requiring an amino acid such as L-leucine, L-homoserine, L-proline, L-serine, L-arginine, L-alanine, and L-valine (refer to U.S. Pat. Nos. 3,708,395 and 3,825,472); mutant strains showing resistance to DL-α-amino-ε-caprolactam, α-amino-lauryllactam, aspartic acid analogue, sulfa drug, quinoid, and N-lauroylleucine; mutant strains showing resistance to an oxaloacetate decarboxylase inhibitor or a respiratory chain enzyme inhibitor (Japanese Patent Laid-open (Kokai) Nos. 50-53588, 50-31093, 52-102498, 53-9394, 53-86089, 55-9783, 55-9759, 56-32995, 56-39778, Japanese Patent Publication Nos. 53-43591 and 53-1833); mutant strains requiring inositol or acetic acid (Japanese Patent Laid-open (Kokai) Nos. 55-9784 and 56-8692); mutant strains that are susceptible to fluoropyruvic acid or a temperature of 34° C. or higher (Japanese Patent Laid-open (Kokai) Nos. 55-9783 and 53-86090); and mutant strains showing resistance to ethylene glycol (U.S. Pat. No. 4,411,997).

<L-Arginine-producing Bacteria>

Examples of L-arginine-producing bacteria and parent strains which can be used to derive such bacteria can include strains in which the activity or activities of one or more kinds of the L-arginine biosynthetic enzymes are enhanced. Examples of such enzymes can include, but are not particularly limited to, N-acetylglutamate synthetase (argA), N-acetylglutamyl phosphate reductase (argC), ornithine acetyl transferase (argJ), N-acetylglutamate kinase (argB), acetylornithine transaminase (argD), ornithine carbamoyl transferase (argF), argininosuccinate synthetase (argG), argininosuccinate lyase (argH), and carbamoyl phosphate synthetase (carAB). As the N-acetylglutamate synthase gene (argA), for example, a gene coding for a mutant N-acetylglutamate synthase desensitized to feedback inhibition by L-arginine by substitution for the amino acid residues corresponding to positions 15 to 19 of the wild type enzyme (EP 1170361 A) can preferably be used.

Examples of L-arginine-producing bacteria and parent strains which can be used to derive such bacteria can also include strains having resistance to an amino acid analogue or the like. Examples of such strains can include, for example, the coryneform bacterium strains having resistance to 2-thiazolealanine and further exhibiting auxotrophy for L-histidine, L-proline, L-threonine, L-isoleucine, L-methionine, or L-tryptophan (Japanese Patent Laid-open (Kokai) No. 54-44096); coryneform bacterium strains resistant to ketomalonic acid, fluoromalonic acid, or monofluoroacetic acid (Japanese Patent Laid-open (Kokai) No. 57-18989); coryneform bacterium strains resistant to argininol (Japanese Patent Publication No. 62-24075); coryneform bacterium strains resistant to X-guanidine (X represents an aliphatic chain or a derivative thereof, Japanese Patent Laid-open (Kokai) No. 2-186995); and coryneform bacterium strains resistant to arginine hydroxamate and 6-azauracil (Japanese Patent Laid-open (Kokai) No. 57-150381). Specific examples of coryneform bacteria having L-arginine-producing ability can include the following strains:

*Corynebacterium glutamicum* (*Brevibacterium flavum*) AJ11169 (FERM BP-6892)

*Corynebacterium glutamicum* (*Brevibacterium lactofermentum*) AJ12092 (FERM BP-6906)

*Corynebacterium glutamicum* (*Brevibacterium flavum*) AJ11336 (FERM BP-6893)

*Corynebacterium glutamicum* (*Brevibacterium flavum*) AJ11345 (FERM BP-6894)

*Corynebacterium glutamicum* (*Brevibacterium lactofermentum*) AJ12430 (FERM BP-2228)

<L-Citrulline-producing Bacteria and L-Ornithine-producing Bacteria>

The biosynthetic pathways of L-citrulline and L-ornithine are common to that of L-arginine. Therefore, an ability to produce L-citrulline and/or L-ornithine can be imparted or enhanced by increasing the activity or activities of N-acetylglutamate synthase (argA), N-acetylglutamyl phosphate reductase (argC), ornithine acetyltransferase (argJ), N-acetylglutamate kinase (argB), acetylornithine transaminase (argD), and/or acetylornithine deacetylase (argE) (WO2006/35831).

<L-Histidine-producing Bacteria>

Examples of L-histidine-producing bacteria and parent strains which can be used to derive such bacteria can include strains in which the activity or activities of one or more of the L-histidine biosynthetic enzymes are enhanced. Examples of such enzymes can include, but are not particularly limited to, ATP phosphoribosyltransferase (hisG), phosphoribosyl AMP cyclohydrolase (hisI), phosphoribosyl-ATP pyrophosphohydrolase (hisI), phosphoribosylformimino-5-aminoimidazole carboxamide ribotide isomerase (hisA), amidotransferase (hisH), histidinol phosphate aminotransferase (his C), histidinol phosphatase (hisB), and histidinol dehydrogenase (hisD).

Among these enzymes, the L-histidine biosynthetic enzymes encoded by hisG and hisBHAFI are known to be inhibited by L-histidine. Therefore, an ability to produce L-histidine can be imparted or enhanced by, for example, introducing a mutation for conferring resistance to feedback inhibition into the gene coding for ATP phosphoribosyltransferase (hisG) (Russian Patent Nos. 2003677 and 2119536).

<L-Cysteine-producing Bacteria>

Examples of L-cysteine-producing bacteria and parent strains which can be used to derive such bacteria can include strains in which the activity or activities of one of more of the L-cysteine biosynthetic enzymes are enhanced. Examples of such enzymes can include, but are not particularly limited to, serine acetyltransferase and 3-phosphoglycerate dehydrogenase. The serine acetyltransferase activity can be enhanced by, for example, introducing a mutant cysE gene coding for a mutant serine acetyltransferase resistant to feedback inhibition by cysteine into a bacterium. Such a mutant serine acetyltransferase is disclosed in, for example, Japanese Patent Laid-open (Kokai) No. 11-155571 and U.S. Patent Published Application No. 20050112731. Further, the 3-phosphoglycerate dehydrogenase activity can be enhanced by, for example, introducing a mutant serA gene coding for a mutant 3-phosphoglycerate dehydrogenase resistant to feedback inhibition by serine into a bacterium. Such a mutant 3-phosphoglycerate dehydrogenase is disclosed in, for example, U.S. Pat. No. 6,180,373.

Further, examples of L-cysteine-producing bacteria and parent strains which can be used to derive such bacteria can also include strains in which the activity or activities of one of more enzymes that catalyze a reaction branching away from the biosynthesis pathway of L-cysteine to generate a compound other than L-cysteine are reduced or eliminated. Examples of such enzymes can include, for example, enzymes involved in decomposition of L-cysteine. Examples of the enzymes involved in decomposition of L-cysteine can include, but are not particularly limited to, cysteine desulfhydrase (aecD) (Japanese Patent Laid-open (Kokai) No. 2002-233384).

Further, examples of L-cysteine-producing bacteria and parent strains which can be used to derive such bacteria can also include strains in which the L-cysteine excretory system is enhanced, and strains in which the sulfate/thiosulfate transport system is enhanced. Examples of proteins of the L-cysteine excretory system can include the protein encoded by the ydeD gene (Japanese Patent Laid-open (Kokai) No. 2002-233384), the protein encoded by the yfiK gene (Japanese Patent Laid-open (Kokai) No. 2004-49237), proteins encoded by the emrAB, emrKY, yojIH, acrEF, bcr, and cusA genes (Japanese Patent Laid-open (Kokai) No. 2005-287333), and the protein encoded by the yeaS gene (Japanese Patent Laid-open (Kokai) No. 2010-187552). Examples of the proteins of the sulfate/thiosulfate transport system can include the proteins encoded by the cysPTWAM gene cluster.

Further, examples of coryneform bacteria having L-cysteine-producing ability can include coryneform bacteria having serine acetyltransferase desensitized to feedback inhibition by L-cysteine thereby to show enhanced intracellular serine acetyltransferase activity (Japanese Patent Laid-open (Kokai) No. 2002-233384).

<L-Methionine-producing Bacteria>

Examples of L-methionine-producing bacteria and parent strains which can be used to derive such bacteria can include L-threonine auxotrophic strains and mutant strains resistant to norleucine (Japanese Patent Laid-open (Kokai) No. 2000-139471). Examples of L-methionine-producing bacteria and parent strains which can be used to derive such bacteria can also include a strain containing a mutant homoserine transsuccinylase resistant to feedback inhibition by L-methionine (Japanese Patent Laid-open (Kokai) No. 2000-139471, U.S. Patent Published Application No. 20090029424). Since L-methionine is biosynthesized via L-cysteine as an intermediate, L-methionine-producing ability can also be improved by improving L-cysteine-producing ability (Japanese Patent Laid-open (Kokai) No. 2000-139471, U.S. Patent Published Application No. 20080311632).

<L-Leucine-producing Bacteria>

Examples of L-leucine-producing bacteria and parent strains which can be used to derive such bacteria can include strains in which the activity or activities of one or more L-leucine biosynthetic enzymes are enhanced. Examples of such enzymes can include, but are not particularly limited to, the enzymes encoded by the genes of the leuABCD operon. Further, for enhancement of the activity of such an enzyme, for example, the mutant leuA gene coding for isopropyl maleate synthase desensitized to feedback inhibition by L-leucine (U.S. Pat. No. 6,403,342) can be preferably used. Examples of coryneform bacteria having L-leucine-producing ability can include, for example, *Corynebacterium glutamicum* (*Brevibacterium lactofermentum*) AJ3718 (FERM P-2516), which is resistant to 2-thiazole alanine and β-hydroxyleucine and auxotrophic for isoleucine and methionine.

<L-Isoleucine-producing Bacteria>

Examples of the method for imparting or enhancing L-isoleucine-producing ability can include, for example, a method of modifying a bacterium so that activity or activities of one or more L-isoleucine biosynthetic enzymes are increased. Examples of such enzymes can include, but are not particularly limited to, threonine deaminase and acetohydroxy acid synthase (Japanese Patent Laid-open (Kokai) No. 2-458, FR 0356739, U.S. Pat. No. 5,998,178).

Examples of coryneform bacteria having L-isoleucine-producing ability can include the coryneform bacterium in which brnE gene coding for a branched chain amino acid excretion protein is amplified (Japanese Patent Laid-open (Kokai) No. 2001-169788), the coryneform bacterium to which L-isoleucine-producing ability is imparted by protoplast fusion with an L-lysine-producing bacterium (Japanese Patent Laid-open (Kokai) No. 62-74293), the coryneform bacterium in which homoserine dehydrogenase is enhanced (Japanese Patent Laid-open (Kokai) No. 62-91193), the threonine hydroxamate resistant strain (Japanese Patent Laid-open (Kokai) No 62-195293), the α-ketomalonic acid resistant strain (Japanese Patent Laid-open (Kokai) No. 61-15695), the methyllysine resistant strain (Japanese Patent Laid-open (Kokai) No. 61-15696), and *Corynebacterium glutamicum* (*Brevibacterium flavum*) AJ12149 (PERM BP-759, U.S. Pat. No. 4,656,135).

<L-Valine-producing Bacteria>

Examples of L-valine-producing bacteria and parent strains which can be used to derive such bacteria can include strains in which the activity or activities of one or more L-valine biosynthetic enzymes are enhanced. Examples of such enzymes can include, but are not particularly limited to, the enzymes encoded by the genes of the ilvGMEDA operon and the enzymes encoded by the genes of the ilvBNC operon. The ilvBN genes code for acetohydroxy acid synthase, and the ilvC gene codes for isomeroreductase (WO00/50624). Expressions of the ilvGMEDA operon and the ilvBNC operon are suppressed, or attenuated, by L-valine, L-isoleucine, and/or L-leucine. Therefore, to enhance enzymatic activities, the suppression of expression by the produced L-valine can be reversed by removing or modifying a region required for the attenuation. Further, the threonine deaminase encoded by the ilvA gene is an enzyme that catalyzes the deamination reaction of L-threonine resulting 2-ketobutyric acid, which is the rate-limiting step of the L-isoleucine biosynthesis system. Therefore, for L-valine production, it is preferred that the threonine deaminase activity is reduced by disrupting the ilvA gene or the like.

Examples of L-valine-producing bacteria and parent strains which can be used to derive such bacteria can also include strains in which the activity or activities of one or more kinds of enzymes that catalyze a reaction branching away from the biosynthetic pathway of L-valine to generate a compound other than L-valine are reduced. Examples of such enzymes can include, but are not particularly limited to, threonine dehydratase involved in the L-leucine synthesis, and the enzymes involved in the D-pantothenic acid synthesis (WO00/50624).

Examples of L-valine-producing bacteria and parent strains which can be used to derive such bacteria can also include strains resistant to an amino acid analogue or the like. Examples of such strains can include, for example, the coryneform bacterium strains which are auxotrophic for L-isoleucine and L-methionine, and resistant to D-ribose, purine ribonucleoside, or pyrimidine ribonucleoside, and have an ability to produce L-valine (FERM P-1841, FERM P-29) (Japanese Patent Publication No. 53-025034), coryneform bacterium strains resistant to polyketides (FERM P-1763, FERM P-1764) (Japanese Patent Publication No. 06-065314), and coryneform bacterium strains resistant to L-valine in a medium containing acetic acid as the sole carbon source and sensitive to pyruvic acid analogues (fluoropyruvic acid etc.) in a medium containing glucose as the sole carbon source (FERM BP-3006, BP-3007) (Japanese Patent No. 3006929).

<L-Alanine-producing Bacteria>

Examples of L-alanine-producing bacteria and parent strains which can be used to derive such bacteria can include the coryneform bacteria deficient in the $H^+$-ATPase (Appl. Microbiol. Biotechnol., 2001 November, 57(4):534-40) and coryneform bacteria in which the aspartate β-decarboxylase activity is enhanced (Japanese Patent Laid-open (Kokai) No. 07-163383).

<L-Tryptophan-producing Bacteria, L-Phenylalanine-producing Bacteria, and L-Tyrosine-producing Bacteria>

Examples of the method for imparting or enhancing L-tryptophan-producing ability, L-phenylalanine-producing ability, and/or L-tyrosine-producing ability can include, for example, a method of modifying a bacterium so that the activity or activities of one or more of the L-tryptophan, L-phenylalanine, and/or L-tyrosine biosynthetic enzymes are enhanced.

Examples of enzymes common to the biosynthesis systems of these aromatic amino acids can include, but are not particularly limited to, 3-deoxy-D-arabinoheptulosonate-7-phosphate synthase (aroG), 3-dehydroquinate synthase (aroB), shikimate dehydrogenase (aroE), shikimate kinase (aroL), 5-enolpyruvylshikimate-3-phosphate synthase (aroA), and chorismate synthase (aroC) (EP 763127 B). The expressions of the genes coding for these enzymes are controlled by the tyrosine repressor (tyrR), and the activities of these enzymes may be enhanced by deleting the tyrR gene (EP 763127 B).

Examples of the L-tryptophan biosynthetic enzymes can include, but are not particularly limited to, anthranilate synthase (trpE), tryptophan synthase (trpAB), and phosphoglycerate dehydrogenase (serA). For example, by introducing a DNA containing the tryptophan operon, L-tryptophan-producing ability can be imparted or enhanced. Tryptophan synthase has α and β subunits encoded by the trpA and trpB genes, respectively. Since anthranilate synthase is subject to feedback inhibition by L-tryptophan, a gene coding for this enzyme can include a mutation for desensitization to feedback inhibition and may be used for enhancing the activity of that enzyme. Since the phosphoglycerate dehydrogenase is subject to feedback inhibition by L-serine, a gene coding for this enzyme can include a mutation for desensitization to feedback inhibition and may be used for enhancing the activity of that enzyme. Further, by enhancing expression of the operon (ace operon) that includes the maleate synthase gene (aceB), isocitrate lyase gene (aceA), and isocitrate dehydrogenase kinase/phosphatase gene (aceK), L-tryptophan-producing ability may be imparted or enhanced (WO2005/103275).

Examples of the L-phenylalanine biosynthetic enzymes can include, but are not particularly limited to, chorismate mutase and prephenate dehydratase. The chorismate mutase and prephenate dehydratase are encoded by the pheA gene as a bifunctional enzyme. Since the chorismate mutase and prephenate dehydratase are subject to feedback inhibition by L-phenylalanine, a gene coding for these enzymes can include a mutation for desensitization to feedback inhibition and may be used for enhancing the activities of these enzymes.

Examples of the L-tyrosine biosynthetic enzymes can include, but are not particularly limited to, chorismate mutase and prephenate dehydrogenase. The chorismate mutase and prephenate dehydrogenase are encoded by the tyrA gene as a bifunctional enzyme. Since the chorismate mutase and prephenate dehydrogenase are subject to feedback inhibition by L-tyrosine, a gene coding for these enzymes can include a mutation for desensitization to feedback inhibition and may be used for enhancing the activities of these enzymes.

The L-tryptophan, L-phenylalanine, and/or L-tyrosine-producing bacteria may be modified so that biosynthesis of an aromatic amino acid other than the objective aromatic amino acid is reduced. Further, the L-tryptophan, L-phenylalanine, and/or L-tyrosine-producing bacteria may be modified so that a by-product uptake system is enhanced. Examples of the by-product can include aromatic amino acids other than the objective aromatic amino acid.

Examples of the gene coding for such a by-product uptake system can include tnaB and mtr, which are genes coding for the L-tryptophan uptake system, pheP, which is a gene coding for the L-phenylalanine uptake system, and tyrP, which is a gene coding for the L-tyrosine uptake system (EP 1484410).

Examples of coryneform bacteria having L-tryptophan-producing ability can include *Corynebacterium glutamicum* AJ12118 (FERM BP-478) (Japanese Patent No. 01681002), which is resistant to sulfaguanidine, the strain introduced with the tryptophan operon (Japanese Patent Laid-open (Kokai) No. 63-240794), and the strain introduced with a gene coding for shikimate kinase derived from a coryneform bacterium (Japanese Patent Laid-open (Kokai) No. 01-994749).

Examples of coryneform bacteria having L-phenylalanine-producing ability can include, for example, the *Corynebacterium glutamicum* strains BPS-13 (FERM BP-1777), K77 (FERM BP-2062), and K78 (FERM BP-2063) (EP 331145 A, Japanese Patent Laid-open (Kokai) No. 02-303495), of which phosphoenolpyruvate carboxylase or pyruvate kinase activity is reduced, and the tyrosine-auxotrophic strain (Japanese Patent Laid-open (Kokai) No. 05-049489).

Examples of coryneform bacteria having L-tyrosine-producing ability can include, for example, *Corynebacterium glutamicum* AJ11655 (FERM P-5836, Japanese Patent Publication No. 2-6517), and *Corynebacterium glutamicum* (*Brevibacterium lactofermentum*) AJ12081 (FERM P-7249, Japanese Patent Laid-open (Kokai) No. 60-70093).

Further, examples of methods for imparting or enhancing an L-amino acid-producing ability can include, for example, a method of modifying a bacterium so that the activity for secreting an L-amino acid from the bacterial cell is increased. The activity for secreting an L-amino acid can be increased by, for example, increasing the expression of a gene coding for a protein responsible for secretion of the L-amino acid. Examples of genes coding for proteins responsible for secretion of various amino acids can include, for example, b2682 gene (ygaZ), b2683 gene (ygaH), b1242 gene (ychE), and b3434 gene (yhgN) (Japanese Patent Laid-open (Kokai) No. 2002-300874).

Further, examples of methods for imparting or enhancing an L-amino acid-producing ability can also include, for example, a method of modifying a bacterium so that the activity or activities of one or more of proteins involved in the glycometabolism and proteins involved in the energy metabolism are increased.

Examples of the proteins involved in the glycometabolism can include proteins involved in uptake of saccharides and the glycolysis system enzymes. Examples of genes coding for the proteins involved in the glycometabolism include the glucose-6-phosphate isomerase gene (pgi, WO01/02542), phosphoenolpyruvate synthase gene (pps, EP 877090 A), phosphoenolpyruvate carboxylase gene (ppc, WO95/06114), pyruvate carboxylase gene (pyc, WO99/18228, EP 1092776 A), phosphoglucomutase gene (pgm, WO03/04598), fructose bisphosphate aldolase gene (pfkB, fbp, WO03/04664), pyruvate kinase gene (pykF, WO03/008609), transaldolase gene (talB, WO03/008611), fumarase gene (fum, WO01/02545), non-PTS sucrose uptake gene (csc, EP 149911 A), and sucrose utilization gene (scrAB operon, WO90/04636).

Examples of genes coding for the proteins involved in the energy metabolism can include the transhydrogenase gene (pntAB, U.S. Pat. No. 5,830,716) and cytochrome bo-type oxidase gene (cyoB, EP 1070376 A).

The genes used for the breeding of the aforementioned L-amino acid-producing bacteria are not limited to the genes exemplified above and genes having a known nucleotide sequence, and may also be variants thereof, so long as the functions of the encoded proteins are not degraded. For example, the genes used for the breeding of the L-amino acid-producing bacteria can be a gene coding for a protein having a known amino acid sequence, but which includes substitution, deletion, insertion, or addition of one or several amino acid residues at one or several positions. For the variants of genes and proteins, the descriptions for variants of the phosphate transporter gene and phosphate transporter described herein can be applied, mutatis mutandis.

<1-2> Enhancement of Phosphate Transporter Activity

The bacterium of the present invention can be modified so that the phosphate transporter activity is increased. The bacterium can be obtained by modifying a coryneform bacterium having an L-amino acid-producing ability so that the phosphate transporter activity thereof is increased. The bacterium can also be obtained by modifying a coryneform bacterium so that the phosphate transporter activity thereof is increased, and then imparting or enhancing an L-amino acid-producing ability. The bacterium can have acquired an L-amino acid-producing ability by being modified so that the phosphate transporter activity thereof is increased. The modifications for constructing the bacterium can be performed in an arbitrary order.

Hereafter, phosphate transporters and genes coding for them will be explained.

The "phosphate transporter" can refer to a protein having the phosphate transporter activity. The "phosphate transporter activity" can refer to an activity for taking up inorganic phosphoric acid (Pi) into the inside of a cell from the outside of the cell.

Examples of the phosphate transporter include the low-affinity inorganic phosphate transporter (Pit) system and high-affinity phosphate-specific transporter (Pst) system. Examples of genes coding for a phosphate transporter (also referred to as "phosphate transporter gene") include, the pitA gene and pitB gene coding for the Pit system, and the pstSCAB gene coding for the Pst system (R. M. Harris et al., Journal of Bacteriology, September 2001, pp. 5008-5014). The Pst system functions as a complex of four proteins (i.e. the pstSCAB gene products).

The activity of either the Pit system or the Pst system may be increased. It is exemplary to increase the activity of the Pit system, and to increase the activity of the PitA protein, which is the pitA gene product.

The pitA gene of the *Escherichia coli* K12 MG1655 strain corresponds to the sequence at positions 3635665 to 3637164 in the genome sequence registered at the NCBI database as GenBank accession NC_000913 (VERSION NC_000913.2 GI: 49175990). The pitA gene of the *Escherichia coli* K12 MG1655 strain is synonymous with ECK3478 and JW3460. Further, the PitA protein of the *Escherichia coli* K12 MG1655 strain is registered as GenBank accession NP_417950 (version NP_417950.1 GI: 16131365, locus_tag="b3493"). The nucleotide sequence of the pitA gene of the MG1655 strain and the amino acid sequence of the PitA protein encoded by this gene are shown in SEQ ID NOS: 1 and 2, respectively.

The pitA gene of the *Pantoea ananatis* LMG20103 strain corresponds to the sequence complementary to the sequence at positions 1397898 to 1399514 in the genome sequence registered at the NCBI database as GenBank accession NC_013956 (VERSION NC_013956.2 GI: 332139403). Further, the PitA protein of the *Pantoea ananatis*

LMG20103 strain is registered as GenBank accession YP_003519531 (version YP_003519531.1 GI: 291616789, locus_tag="PANA_1236"). The nucleotide sequence of the pitA gene of the *Pantoea ananatis* LMG20103 strain and the amino acid sequence of the PitA protein encoded by this gene are shown in SEQ ID NOS: 3 and 4, respectively.

The pitA gene of the *Corynebacterium glutamicum* ATCC 13032 strain corresponds to the sequence complementary to the sequence at positions 481391 to 482776 in the genome sequence registered at the NCBI database as GenBank accession NC_003450 (VERSION NC_003450.3 GI: 58036263). The pitA gene of the *Corynebacterium glutamicum* ATCC 13032 strain is synonymous with Cgl0460. Further, the PitA protein of the *Corynebacterium glutamicum* ATCC 13032 strain is registered as GenBank accession NP_599707 (version NP_599707.1 GI: 19551705, locus_tag="NCgl0445"). The nucleotide sequence of the pitA gene of the *Corynebacterium glutamicum* ATCC 13032 strain and the amino acid sequence of the PitA protein encoded by this gene are shown in SEQ ID NOS: 25 and 26, respectively. Further, the nucleotide sequence of the pitA gene of the *Corynebacterium glutamicum* 2256 strain (ATCC 13869) and the amino acid sequence of the PitA protein encoded by this gene are shown in SEQ ID NOS: 5 and 6, respectively.

The phosphate transporter may be a variant of any of the aforementioned phosphate transporters such as the various PitA proteins, so long as it has the phosphate transporter activity. Such a variant may also be referred to as "conservative variant". Examples of the conservative variant include, for example, homologues and artificially modified variants of the aforementioned phosphate transporters such as the various PitA proteins.

A gene coding for a homologue of the aforementioned PitA protein can easily be obtained from a public database by, for example, a BLAST search or FASTA search using the nucleotide sequence of the aforementioned pitA gene (SEQ ID NO: 1, 3, 5, or 25) as a query sequence. Further, a gene coding for a homologue of the aforementioned PitA protein can be obtained by, for example, PCR using the chromosome of a bacterium or yeast as the template, and oligonucleotides prepared on the basis of a known gene sequence thereof as primers.

The gene coding for a conservative variant of the phosphate transporter may be, for example, such a gene as mentioned below. That is, the phosphate transporter gene may be a gene coding for a protein having the aforementioned amino acid sequence but that includes substitution, deletion, insertion, or addition of one or several amino acid residues at one or several positions, so long as it codes for a protein having the phosphate transporter activity. In such a case, usually 70% or more, 80% or more, or 90% or more, of the phosphate transporter activity is maintained in the variant protein, relative to the protein before the substitution, addition, deletion, insertion, or addition of one or several amino acid residues. Although the number of "one or several" may differ depending on the positions in the three-dimensional structure of the protein or the types of amino acid residues, specifically, it can be 1 to 20, 1 to 10, 1 to 5, or 1 to 3.

The aforementioned substitution, deletion, insertion, or addition of one or several amino acid residues can be a conservative mutation that allows for the maintenance of the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as described above can include a naturally occurring mutation due to an individual difference, or a difference of species of the organism from which the gene is derived (mutant or variant).

Furthermore, the gene having such a conservative mutation as mentioned above may be a gene coding for a protein showing a homology of 80% or more, 90% or more, 95% or more, 97% or more, 99% or more, to the total amino acid sequence mentioned above, and having the phosphate transporter activity. In addition, in this specification, "homology" may mean "identity".

Moreover, the phosphate transporter gene may be a DNA that is able to hybridize under stringent conditions with a probe that can be prepared from a known gene sequence, such as a sequence complementary to a part or the entire described nucleotide sequence, and which DNA codes for a protein having the phosphate transporter activity. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 80% homologous, not less than 90% homologous, not less than 95% homologous, not less than 97% homologous, or even not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing the nucleotide sequence as a template. As the probe, for example, a DNA fragment having a length of about 300 bp can be used. When a DNA fragment having a length of about 300 bp is used as the probe, the washing conditions of the hybridization may be, for example, 50° C., 2×SSC and 0.1% SDS.

Further, the phosphate transporter gene may be a gene in which an arbitrary codon is replaced with an equivalent codon, so long as the gene codes for a protein having the phosphate transporter activity. For example, the phosphate transporter gene may be modified so that it has optimal codons according to codon frequencies in the chosen host.

The percentage of the sequence identity between two sequences can be determined by, for example, using a mathematical algorithm. Non-limiting examples of such a mathematical algorithm include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and an modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program include, but are not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences can be calculated as the ratio of residues matching in the two sequences when aligning the two sequences so as to fit maximally with each other.

The above descriptions concerning variants of genes and proteins can also be applied mutatis mutandis to arbitrary proteins such as L-amino acid biosynthetic enzymes and genes coding for them.

<1-3> Methods for Increasing Activity of Protein

Hereinafter, methods for increasing the activity of a protein will be explained.

The expression "the activity of a protein is increased" can mean that the activity of the protein per cell is increased as compared with that of a non-modified strain such as a wild-type strain and a parent strain. The phrase that "the activity of a protein is increased" is also expressed as "the activity of a protein is enhanced". Specifically, the expression "the activity of a protein is increased" can mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may mean the transcription amount of a gene (the amount of mRNA) coding for the protein, or the translation amount of the protein (the amount of the protein). Although the degree of the increase in the activity of a protein is not particularly limited so long as the activity of the protein is increased as compared with a non-modified strain, the activity of the protein may be increased 1.5 times or more, 2 times or more, or 3 times or more, as compared with that of a non-modified strain. Further, the phrase "the activity of a protein is increased" can include not only when the activity of an objective protein is increased in a strain inherently having the activity of the objective protein, but also when the activity of an objective protein is imparted to a strain not inherently having the activity of the objective protein. Further, so long as the activity of the protein is eventually increased, the activity of the objective protein inherently present in the host may be attenuated and/or eliminated, and then an appropriate type of the protein may be introduced thereto.

The modification that increases the activity of a protein can be attained by, for example, increasing the expression of a gene coding for the protein. The phrase that "the expression of a gene is increased" can also mean that "the expression of a gene is enhanced". The expression of a gene may be increased 1.5 times or more, 2 times or more, or 3 times or more, as compared with that observed in a non-modified strain. Further, the phrase "the expression of a gene is increased" can include not only when the expression amount of a target gene is increased in a strain that inherently expresses the target gene, but also when the gene is introduced into a strain that does not inherently express the target gene, and expressed therein. That is, the phrase "the expression of a gene is increased" can also mean, for example, that the target gene is introduced into a strain that does not have the gene, and is then expressed therein.

The expression of a gene can be increased by, for example, increasing the copy number of the gene.

The copy number of a gene can be increased by introducing the gene into the chromosome of the chosen host. A gene can be introduced into a chromosome by, for example, using homologous recombination (Miller, J. H., Experiments in Molecular Genetics, 1972, Cold Spring Harbor Laboratory). Only one copy, or two or more copies of a gene may be introduced. For example, by performing homologous recombination using a sequence which is present in multiple copies on the chromosome as a target, multiple copies of a gene can be introduced into the chromosome. Examples of such a sequence which is present in multiple copies on a chromosome include repetitive DNAs, and inverted repeats located at the both ends of a transposon. Alternatively, homologous recombination may be performed by using an appropriate sequence on a chromosome such as a gene unnecessary for the L-amino acid production as a target. Homologous recombination can be performed by, for example, a method of using a linear DNA such as Red-driven integration (Datsenko, K. A., and Wanner, B. L., Proc. Natl. Acad. Sci. USA, 97:6640-6645 (2000)), a method of using a plasmid including a temperature sensitive replication origin, a method of using a plasmid capable of conjugative transfer, a method of using a suicide vector not including a replication origin that functions in a host, or a transduction method using a phage. Further, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole or a part of the gene, PCR using primers prepared on the basis of the sequence of the gene, or the like.

Further, the copy number of a target gene can also be increased by introducing a vector including the gene into a host. For example, the copy number of a target gene can be increased by ligating a DNA fragment including the target gene with a vector that functions in the chosen host to construct an expression vector of the gene, and by transforming the host with the expression vector. The DNA fragment including the target gene can be obtained by, for example, PCR using the genomic DNA of a microorganism having the target gene as the template. As the vector, a vector autonomously replicable in the cell of the host can be used. The vector can be a multi-copy vector. Further, the vector can include a marker such as an antibiotic resistance gene for selection of transformant. The vector may be, for example, a vector derived from a bacterial plasmid, a vector derived from a yeast plasmid, a vector derived from a bacteriophage, cosmid, phagemid, or the like. Specific examples of a vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving the foregoing vectors and including a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; and pCG4 and pCG11 described in Japanese Patent Laid-open (Kokai) No. 57-183799.

When a gene is introduced, it is sufficient that the gene is expressibly harbored by the bacterium of the present invention. Specifically, it is sufficient that the gene is introduced so that it is expressed under the control of a promoter sequence that functions in the bacterium. The promoter may be a promoter derived from the host, or a heterogenous promoter. The promoter may be the native promoter of the gene to be introduced, or a promoter of another gene. As the promoter, for example, potent promoters, as described herein, may also be used.

Further, when two or more kinds of genes are introduced, it is sufficient that the genes each are expressibly harbored by the bacterium of the present invention. For example, all the genes may be present on a single expression vector or a chromosome. Further, the genes may be present on two or more expression vectors, or on a single or two or more expression vectors and a chromosome. An operon made up of two or more genes may also be introduced.

The gene to be introduced is not particularly limited so long as it codes for a protein that functions in the host. The gene to be introduced may be a gene derived from the host, or may be a heterogenous gene.

Further, the expression of a gene can be increased by improving the transcription efficiency of the gene. The transcription efficiency of a gene can be improved by, for example, replacing the promoter of the gene on a chromosome with a stronger or more potent promoter. The "stronger or more potent promoter" means a promoter providing an improved transcription of a gene as compared with the inherent wild-type promoter of the gene. Examples of stronger or potent promoters usable in coryneform bacteria include the artificially designed P54-6 promoter (Appl. Microbiol. Biotechnolo., 53, 674-679 (2000)), pta, aceA, aceB, adh, and amyE promoters inducible in coryneform bacteria with acetic acid, ethanol, pyruvic acid, or the like, cspB, SOD, and tuf promoters, which are potent promoters providing a large expression amount in coryneform bacteria (Journal of Biotechnology, 104 (2003) 311-323; Appl. Environ. Microbiol., 2005 December; 71 (12):8587-96.), lac promoter, tac promoter, and trc promoter. Further, as the stronger promoter, a highly-active native promoter may also be obtained by using various reporter genes. For example, by making the −35 and −10 regions in a promoter region closer to the consensus sequence, the activity of the promoter can be enhanced (WO00/18935). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

Further, the expression of a gene can also be enhanced by improving the translation efficiency of the gene. The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides improved translation of mRNA as compared with the inherent wild-type SD sequence of the gene. Examples of stronger SD sequences can include, for example, RBS of the gene 10 derived from phage T7 (Olins P. O. et al, Gene, 1988, 73, 227-235). Further, it is known that substitution, insertion, or deletion of several nucleotides in the spacer region between RBS and the start codon, especially in a sequence immediately upstream of the start codon (5'-UTR), significantly affects the stability and translation efficiency of mRNA, and hence, the translation efficiency of a gene can also be improved by this modification.

Sites that affect the gene expression, such as a promoter, SD sequence, and spacer region between RBS and the start codon, can also be collectively called "expression control regions". An expression control region can be identified by using a promoter search vector or gene analysis software such as GENETYX. Such an expression control region can be modified by, for example, a method of using a temperature sensitive vector or the Red driven integration method (WO2005/010175).

The translation efficiency of a gene can also be improved by, for example, modifying codons. For example, in the case of heterogenous expression of a gene or the like, the translation efficiency of the gene can be improved by replacing a rare codon present in the gene with a more frequently used synonymous codon. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y. et al, Nucl. Acids Res., 28, 292 (2000)).

Further, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Further, the modification that increases the activity of an enzyme can also be attained by, for example, enhancing the specific activity of the enzyme. An enzyme showing an enhanced specific activity can be obtained by, for example, searching various organisms. Further, a highly-active type of an existing enzyme may also be obtained by introducing a mutation into the existing enzyme. Enhancement of the specific activity may be independently used, or may be used in an arbitrary combination with such methods for enhancing the gene expression as mentioned above.

The activity of the phosphate transporter can also be increased by, for example, making a host harbor a phosphate transporter gene coding for a phosphate transporter having a "specific mutation". A phosphate transporter having the "specific mutation" can also be referred to as a mutant phosphate transporter, and a gene coding for it can also be referred to as a mutant phosphate transporter gene. Further, a phosphate transporter not having the "specific mutation" can also be referred to as a wild-type phosphate transporter, and a gene coding for it can also be referred to as a wild-type phosphate transporter gene. The mutant phosphate transporter having the "specific mutation" may have a specific activity higher than that of a wild-type phosphate transporter.

Examples of the wild-type phosphate transporter include PitA proteins not having the "specific mutation" (wild-type PitA protein). Examples of the mutant phosphate transporter include PitA proteins having the "specific mutation" (mutant PitA protein). A gene coding for a wild-type PitA protein can also be referred to as a wild-type pitA gene, and a gene coding for a mutant PitA protein can also be referred to as a mutant pitA gene. Examples of wild-type PitA proteins can include the various PitA proteins exemplified above, and conservative variants thereof not having the "specific mutation". That is, the mutant phosphate transporter may be the same as the various PitA proteins exemplified above and conservative variants thereof, provided that it has the "specific mutation".

Specifically, the mutant phosphate transporter may be, for example, a protein having the amino acid sequence shown in SEQ ID NO: 2, 4, 6, or 26 provided that it has the "specific mutation". Further, specifically, the mutant phosphate transporter may also be, for example, a protein having the amino acid sequence shown in SEQ ID NO: 2, 4, 6, or 26, but can include substitution, deletion, insertion, or addition of one or several amino acid residues, provided that it has the "specific mutation". Further, specifically, the mutant phosphate transporter may also be, for example, a protein having a homology of 80% or more, 90% or more, 95% or more, 97% or more, or even 99% or more, to the amino acid sequence shown in SEQ ID NO: 2, 4, 6, or 26, provided that it has the "specific mutation". In addition, in this specification, "homology" may mean "identity".

In other words, the mutant phosphate transporter may be a variant of any of the various PitA proteins exemplified above, which has the "specific mutation" and further can include a conservative mutation at a site other than that of the "specific mutation".

Specifically, the mutant phosphate transporter may be, for example, a protein having the amino acid sequence shown in SEQ ID NO: 2, 4, 6, or 26, but having the "specific mutation", and further including substitution, deletion, insertion, or addition of one or several amino acid residues at a site other than that of the "specific mutation".

The number of "one or several" can be, specifically, 1 to 20, 1 to 10, 1 to 5, or 1 to 3. The aforementioned substitution, deletion, insertion, or addition of one or several amino acid residues can be a conservative mutation that allows for the maintanence of the normal function of the protein. Typical examples of the conservative mutation are conservative substitutions. A conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, inversion, or the like of amino acid residues as described above can include a naturally occurring mutation due to an individual difference, or a difference of species of the organism from which the gene is derived (mutant or variant).

Examples of the "specific mutation" can include, for example, a mutation wherein the amino acid residue at position 246 in SEQ ID NO: 6, which is typically a phenylalanine residue but can be any amino acid residue, is replaced with an amino acid residue other than a phenylalanine residue. The amino acid residue that replaces the amino acid residue at position 246 in SEQ ID NO: 6 may be any natural amino acid other than phenylalanine, such as lysine, glutamic acid, tyrosine, valine, isoleucine, serine, aspartic acid, asparagine, glutamine, arginine, cysteine, methionine, tryptophan, glycine, alanine, and histidine. Serine is a particular example.

The "position X" in an amino acid sequence is the X-th position counted from the N-terminus of the amino acid sequence, and the amino acid residue of the N-terminus is the amino acid residue at position 1. The position of an amino acid residue represents a relative position, and the absolute position thereof may shift due to deletion, insertion, addition, or the like of an amino acid residue or residues. That is, when one amino acid residue is deleted on the N-terminal side of position 246 in the sequence of SEQ ID NO: 6, the "amino acid residue at position 246 in SEQ ID NO: 6" actually becomes the 245th amino acid residue counted from the N-terminus. Further, when one amino acid residue is inserted into the N-terminal side of position 246 in the sequence of SEQ ID NO: 6, the "amino acid residue at position 246 in SEQ ID NO: 6" actually becomes the 247th amino acid residue counted from the N-terminus. The amino acid residue at position 246 in SEQ ID NO: 6 can correspond to the amino acid residue at position 246 in SEQ ID NO: 26.

Which amino acid residue is at position 246 in SEQ ID NO: 6 in an amino acid sequence can be determined based on an alignment between the amino acid sequence and the amino acid sequence of SEQ ID NO: 6. The alignment can be performed by, for example, using known gene analysis software. Specific examples of such software include DNA-SIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

When a wild-type phosphate transporter has an amino acid sequence other than the amino acid sequence shown in SEQ ID NO: 6, the "amino acid residue at position 246 in SEQ ID NO: 6", typically a phenylalanine residue, may not be a phenylalanine residue. That is, for example, the "mutation wherein the amino acid residue at position 246 in SEQ ID NO: 6 is replaced with serine residue" is not limited to mutations wherein the phenylalanine residue at position 246 in SEQ ID NO: 6 is replaced with a serine residue, but can also include mutations wherein whatever amino acid residue occupies position 246 in SEQ ID NO: 6 is replaced with a serine residue.

The mutant phosphate transporter gene can be obtained by modifying a wild-type phosphate transporter gene so that the encoded phosphate transporter has the "specific mutation". The wild-type phosphate transporter gene may be a gene derived from a host into which the mutant phosphate transporter gene is to be introduced, or may be a gene of heterogenous origin. The modification of DNA can be performed by a known method. Specific examples of the site-specific mutagenesis method for introducing an objective mutation into an objective site of DNA can include, for example, a method of using PCR (Higuchi, R., 61, in PCR Technology, Erlich, H. A. Eds., Stockton Press, 1989; Carter P., Meth. In Enzymol., 154, 382, 1987), and a method of using a phage (Kramer, W. and Frits, H. J., Meth. in Enzymol., 154, 350, 1987; Kunkel, T. A. et al., Meth. in Enzymol., 154, 367, 1987). Further, the mutant phosphate transporter gene can also be obtained by chemical synthesis.

By introducing a mutant phosphate transporter gene into a coryneform bacterium, the coryneform bacterium can be made to harbor the mutant phosphate transporter gene. The method for introducing the mutant phosphate transporter gene into the coryneform bacterium is not particularly limited, and a conventionally known method may be used. For example, a mutant phosphate transporter gene can be introduced into a coryneform bacterium in the same manner as that of the method of increasing the copy number of a gene mentioned above. Further, a wild-type phosphate transporter gene of a coryneform bacterium may be modified so that the encoded phosphate transporter should have the "specific mutation" by natural mutation or a treatment with a mutagen. When the bacterium harbors a mutant phosphate transporter gene, the bacterium may or may not have a wild-type phosphate transporter gene. The bacterium may have one or more copies of a mutant phosphate transporter gene.

The method for the transformation is not particularly limited, and conventionally known methods can be used. Suitable methods include, for example, treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, other suitable methods include making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Further, the electric pulse method reported for coryneform bacteria (Japanese Patent Laid-open (Kokai) No. 2-207791) can also be used.

An increase in the activity of a protein can be confirmed by measuring the activity of the protein. The phosphate transporter activity can be measured by, for example, measuring uptake of inorganic phosphoric acid using a known method (R. M. Harris et al., Journal of Bacteriology, September 2001, pp. 5008-5014).

An increase in the activity of a protein can also be confirmed by confirming an increase in the expression of a gene coding for the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that observed in a non-modified strain such as a wild-type strain or parent strain. Examples of the method for evaluating the amount of mRNA include Northern hybridization, RT-PCR, and so forth (Sambrook, J., et al., Molecular Cloning A Laboratory Manual/Third Edition, Cold spring Harbor Laboratory Press, Cold Spring Harbor (USA), 2001). The amount of mRNA may increase, for example, 1.5 times or more, 2 times or more, or 3 times or more, as compared with that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase, for example, 1.5 times or more, 2 times or more, or 3 times or more, as compared with that of a non-modified strain.

The aforementioned methods for increasing the activity of a protein can be applied to enhancement of the activity of any objective protein, such as the L-amino acid biosynthetic enzymes, and enhancement of the expression of a gene such as genes coding for any objective protein, in addition to the enhancement of the activity of the phosphate transporter.

<1-4> Method for Reducing Activity of Protein

Hereafter, methods for reducing the activity of a protein will be explained below.

The expression "the activity of a protein is reduced" can mean that the activity of the protein per cell is decreased as compared with that of a non-modified strain such as a wild-type strain or parent strain, and includes when the activity has completely disappeared. Specifically, the expression "the activity of a protein is reduced" can mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may mean the transcription amount of a gene (the amount of mRNA) coding for the protein or the translation amount of the protein (the amount of the protein).

The phrase "the number of molecules of the protein per cell is reduced" can include the situation when the protein is completely absent. The phrase "the function of each molecule of the protein is reduced" can include when the function of each protein molecule completely disappears. Although the degree of the reduction in the activity of a protein is not particularly limited so long as the activity is reduced as compared with that of a non-modified strain, it may be reduced to, for example, 50% or less, 20% or less, 10% or less, 5% or less, or 0% of that of a non-modified strain.

The modification for reducing the activity of a protein can be attained by, for example, reducing the expression of a gene coding for the protein. The phrase "the expression of a gene is reduced" can include when that the gene is not expressed at all. The phrase "the expression of a gene is reduced" can also mean that "the expression of a gene is attenuated". The expression of a gene may be reduced to 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter and Shine-Dalgarno (SD) sequence. When an expression control sequence is modified, one or more nucleotides, two or more nucleotides, three or more nucleotides, of the expression control sequence can be modified. Further, a part of or the entire expression control sequence may be deleted. The expression of a gene can also be reduced by, for example, manipulating a factor responsible for expression control. Examples of the factor responsible for expression control include molecules responsible for transcription or translation control (inducers, inhibitors, etc.), proteins responsible for transcription or translation control (transcription factors etc.), nucleic acids responsible for transcription or translation control (siRNA etc.), and so forth.

The modification for reducing the activity of a protein can also be attained by, for example, disrupting a gene coding for the protein. Disruption of a gene can be attained by, for example, deleting a part or the entire coding region of the gene on the chromosome. Furthermore, the entire gene including sequences upstream and downstream from the gene on the chromosome may be deleted. The region to be deleted may be any region such as an N-terminus region, an internal region, or a C-terminus region, so long as the activity of the protein can be reduced. Deletion of a longer region can usually more surely inactivate the gene. Further, it is preferred that reading frames of the sequences upstream and downstream from the deleted region are not the same.

Genes can also be disrupted by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Genes can also be disrupted by, for example, inserting another sequence into a coding region of the gene on a chromosome. The insertion site may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an L-amino acid.

Such modification of a gene on a chromosome as described above can be attained by, for example, preparing a deficient type gene in which a partial sequence of the gene is deleted so that it cannot produce a protein that can normally function, and transforming a host with a recombinant DNA including the deficient type gene to cause homologous recombination between the deficient type gene and the wild-type gene on a chromosome and thereby substituting the deficient type gene for the wild-type gene on the chromosome. In this procedure, if a marker gene selected according to the characteristics of the host such as auxotrophy is included in the recombinant DNA, the operation becomes easy. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid including a temperature sensitive replication origin, a method of using a plasmid capable of conjugative transfer, a method of utilizing a suicide vector not including a replication origin that functions in a host (U.S. Pat. No. 6,303,383, Japanese Patent Laid-open (Kokai) No. 05-007491), and so forth.

The modification for reducing the activity of a protein can also be attained by, for example, a mutagenesis treatment. Exemplary mutagenesis treatments include typical mutation treatments such as irradiation of X-ray or ultraviolet and treatment with a mutation agent such as N-methyl-N-nitro-N-nitrosoguanidine (MNNG), ethyl methanesulfonate (EMS), and methyl methanesulfonate (MMS).

A reduction in the activity of a protein can be confirmed by measuring the activity of the protein.

A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA include Northern hybridization, RT-PCR, and so forth (Molecular Cloning, Cold spring Harbor Laboratory Press, Cold Spring Harbor (USA), 2001). The amount of mRNA can be decreased to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be decreased to, for example, 50% or less, 20% or less, 10% or less, 5% or less, or 0%, of that observed in a non-modified strain.

Disruption of a gene can be confirmed by determining the nucleotide sequence of a part or the entire gene, restriction enzyme map, full length, or the like of the gene depending on the means used for the disruption.

The aforementioned methods for reducing the activity of a protein can be applied to reduction in the activity of an objective protein such as enzymes that catalyze a reaction branching away from the biosynthetic pathway of an objective L-amino acid to generate a compound other than the objective L-amino acid, and reduction in the expression of an objective gene such as genes coding for those objective proteins.

<2> Method for Producing L-amino Acid of the Present Invention

The method of the present invention is a method for producing an L-amino acid including the steps of culturing the bacterium of the present invention in a medium, and collecting the L-amino acid from the medium.

The medium for the culture is not particularly limited, so long as the bacterium of the present invention can proliferate in it, and an objective L-amino acid can be produced. As the medium, for example, a usual medium used for culture of bacteria such as coryneform bacteria can be used. As the medium, for example, a medium containing carbon source, nitrogen source, phosphorus source, and sulfur source, as well as components selected from other various organic components and inorganic components as required can be used. Types and concentrations of the medium components can be appropriately determined according to various conditions such as the type of the chosen bacterium and the type of the amino acid to be produced.

Specific examples of the carbon source can include, for example, saccharides such as glucose, fructose, sucrose, lactose, galactose, xylose, arabinose, blackstrap molasses, starch hydrolysates, and hydrolysates of biomass, organic acids such as acetic acid, fumaric acid, citric acid, and succinic acid, alcohols such as glycerol, crude glycerol, and ethanol, and aliphatic acids. As the carbon source, a single kind of carbon source may be used, or two or more kinds of carbon sources may be used in combination.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas or aqueous ammonia used for adjusting pH may also be used as the nitrogen source. As the nitrogen source, a single kind of nitrogen source may be used, or two or more kinds of nitrogen sources may be used in combination.

Specific examples of the phosphate source can include, for example, phosphoric acid salts such as potassium dihydrogenphosphate and dipotassium hydrogenphosphate, and phosphoric acid polymers such as pyrophosphoric acid. As the phosphate source, a single kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, a single kind of sulfur source may be used, or two or more kinds of sulfur sources may be used in combination.

Specific examples of other various organic components and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing those such as peptone, casamino acid, yeast extract, and soybean protein decomposition product. As other various organic components and inorganic components, a single kind of component may be used, or two or more kinds of components may be used in combination.

Further, when an auxotrophic mutant that requires an amino acid or the like for growth thereof is used, the medium can be supplemented with the required nutrient. For example, in many of L-lysine-producing bacteria, the L-lysine biosynthetic pathway is enhanced and the L-lysine degrading ability is attenuated. Therefore, when such an L-lysine-producing bacterium is cultured, for example, one or more amino acids such as L-threonine, L-homoserine, L-isoleucine, and L-methionine can be added to the medium.

Further, when L-glutamic acid is produced by using a coryneform bacterium, the amount of biotin in the medium can be limited, or a surfactant or penicillin can be added to the medium.

The culture conditions are not particularly limited so long as the bacterium of the present invention can proliferate, and the objective L-amino acid can be produced. The culture can be performed, for example, under typical conditions for culturing bacteria such as coryneform bacteria. The culture conditions can be appropriately set according to various criteria such as the type of chosen bacterium and the type of amino acid to be produced.

The culture can be aerobically performed by using a liquid medium. Specifically, the culture can be performed with aeration or shaking. The culture temperature may be, for example, 20 to 40° C., or 25 to 37° C. pH of the medium may be adjusted to, for example, 5 to 8. For adjusting pH, inorganic or organic acidic or alkaline substances, such as ammonia gas and so forth, can be used. The culture period may be, for example, 15 to 90 hours. The culture can be performed as batch culture, fed-batch culture, continuous culture, or a combination of these. Further, the culture may be performed as two steps of a seed culture and a main culture. In such a case, the culture conditions of the seed culture and the main culture may or may not be the same. For example, both the seed culture and the main culture may be performed as batch culture. Alternatively, for example, the seed culture may be performed as batch culture, and the main culture may be performed as fed-batch culture or continuous culture. By culturing the bacterium of the present invention under such conditions, an L-amino acid is accumulated in the medium.

Moreover, when L-glutamic acid is produced, the culture can be performed by using a liquid medium adjusted so that L-glutamic acid precipitates into the medium. Examples of the condition under which L-glutamic acid is precipitated can include, for example, pH of 5.0 to 4.0, pH 4.5 to 4.0, pH 4.3 to 4.0, or pH 4.0 (EP 1078989 A).

When a basic amino acid such as L-lysine is produced, there may be employed a method in which the basic amino acid is produced by fermentation using bicarbonate ions and/or carbonate ions as major counter ions for the basic amino acid (Japanese Patent Laid-open (Kokai) No. 2002-65287, U.S. Patent Published Application No. 20020025564, EP 1813677 A). By such a method, a basic amino acid can be produced while reducing the amount(s) of sulfate ions and/or chloride ions, which have been conventionally used as counter ions for a basic amino acid.

The L-amino acid can usually be collected from the fermentation broth by a combination of conventionally known methods such as ion-exchange resin method (Nagai, H. et al., Separation Science and Technology, 39(16), 3691-

3710), precipitation, membrane separation (Japanese Patent Laid-open (Kokai) Nos. 9-164323 and 9-173792), crystallization (WO2008/078448, WO2008/078646), and other methods. When the L-amino acid accumulates in cells, the cells can be disrupted with, for example, ultrasonic waves or the like, and then the L-amino acid can be collected by the ion exchange resin method or the like from the supernatant obtained by removing the cells from the cell-disrupted suspension by centrifugation. The L-amino acid to be collected may be a free compound, a salt thereof, or a mixture thereof. Examples of the salt can include, for example, sulfate, hydrochloride, carbonate, ammonium salt, sodium salt, and potassium salt. For example, in the case of L-glutamic acid, monosodium L-glutamate (MSG) can be obtained by crystalizing monoammonium L-glutamate in the fermentation broth by addition of an acid, and then by adding an equimolar of sodium hydroxide to the crystal. In addition, decolorization can be performed by using activated carbon before and/or after the crystallization (see, Tetsuya KAWAKITA, "Industrial Crystallization for Monosodium L-Glutamate.", Bulletin of the Society of Sea Water Science, Japan, Vol. 56:5).

Further, when the L-amino acid accumulates in the medium, it can be collected by centrifugation, filtration, or the like. The L-amino acid that has precipitated into the medium may also be isolated together with the L-amino acid that has dissolved in the medium after crystallization of the dissolved L-amino acid dissolved.

The L-amino acid collected may contain bacterial cells, medium components, moisture, and by-product metabolites of the bacterium, in addition to the L-amino acid. The purity of the L-amino acid collected may be, for example, 50% or higher, 85% or higher, 95% or higher (Japanese Patent No. 1214636, U.S. Pat. Nos. 5,431,933, 4,956,471, 4,777,051, 4,946,654, 5,840,358, 6,238,714, U.S. Patent Published Application No. 20050025878).

When the L-amino acid is L-glutamic acid, for example, the monosodium L-glutamate crystal can be used as an umami seasoning. The monosodium L-glutamate crystal can be used as a seasoning in combination with a nucleic acid such as 5'-GMP disodium salt and 5'-IMP disodium salt, which also have umami taste.

Also, an embodiment of the method of the present invention is a method for producing an L-amino acid including the steps of culturing a coryneform bacterium having an L-amino acid-producing ability in a medium, and collecting the L-amino acid from the medium, wherein the bacterium harbors a mutant pitA gene coding for a phosphate transporter having a mutation wherein the amino acid residue at position 246 in SEQ ID NO: 6, typically a phenylalanine residue, is replaced with an amino acid residue other than a phenylalanine residue.

To this embodiment of the method of the present invention, the aforementioned descriptions concerning the bacterium of the present invention and the method of the present invention can be applied, mutatis mutandis. For example, in this embodiment, the amino acid residue at position 246 in SEQ ID NO: 6, typically a phenylalanine residue, is replaced with a serine residue. Further, in this embodiment, the coryneform bacterium can be a Corynebacterium glutamicum. Furthermore, in this embodiment, the amino acid to be produced may be any L-amino acid, and L-glutamic acid is a particular example.

EXAMPLES

The present invention will be more specifically explained with reference to the following non-limiting examples.

Example 1

Glutamic Acid (Glu) Production Culture Using pitA-enhanced Strain

In this example, Glu production was performed by using a Glu-producing strain of C. glutamicum in which the expression of the pitA gene was enhanced, and the influence of the enhancement of pitA gene expression on the Glu production was evaluated.

The strains used were as follows.

C. glutamicum 2256 Δ ldhA Δ sucA yggB*/pVK9

C. glutamicum 2256 Δ ldhA Δ sucA yggB*/pVK9-Plac-pitA

Method for Constructing Bacterial Strains

As a model Glu-producing strain, 2256 Δ ldhA Δ sucA yggB* strain was constructed by the following method using the C. glutamicum 2256 strain (ATCC 13869) as the parent strain. The primers used are shown in Table 1.

TABLE 1

| Primer | Nucleotide Sequence (5' → 3') | SEQ ID NO: |
|---|---|---|
| 1 | cactgcacggccctgcgaac | 7 |
| 2 | cgccaactaggcgccaaaaattcc tgatttccctaaccggac | 8 |
| 3 | tgtgggccttcggcgaggac | 9 |
| 4 | gtccggttagggaaatcaggaatt tttggcgcctagttggcg | 10 |
| 5 | gagtcgaccgcaccccattttca ta | 11 |
| 6 | tggtcgacgtgaatgctcggcggg atcc | 12 |
| 7 | ccaggcactcgtcctcggtt | 13 |
| 8 | aggctagtgcaggactataaagac cagttctcctaaaaataacgtgtc | 14 |
| 9 | tccatcgtggccaccgatcc | 15 |
| 10 | gacacgttattttaggagaactg gtctttatagtcctgcactagcct | 16 |
| 11 | cgggatccccaccggcgtactcgt g | 17 |
| 12 | ccacggatccttccaatgctattg gttg | 18 |
| 13 | agcttgcatgcctgcagaggagga ttataatggtcaccccaatca | 19 |
| 14 | cggtacccggggatcctgcccacg agggtgacctca | 20 |

First, DNA fragments for deleting the ldhA gene were amplified by using the chromosomal DNA of the 2256 strain as the template, and the pair of the primers 1 and 2 and the pair of the primers 3 and 4, individually. Then, PCR was performed by using a mixture of equivalent amounts of both the amplified fragments as the template as well as the primers 5 and 6 to obtain a DNA fragment consisting of both the fragments fused together. The obtained DNA fragment was treated with SalI, and introduced into the plasmid pBS4S (WO2005/113745) at the SalI site to construct a plasmid that was then used to delete ldhA. This plasmid was inserted into the chromosome of the 2256 strain, and then cured therefrom, so as to delete the ldhA gene.

Then, DNA fragments for deleting the sucA gene were amplified by using the chromosomal DNA of the 2256 strain as the template, and the pair of the primers 7 and 8 and the pair of the primers 9 and 10, individually. Then, PCR was performed by using a mixture of equivalent amounts of both the amplified fragments as the template as well as the primers 11 and 12 to obtain a DNA fragment consisting of both the fragments fused together. The obtained DNA fragment was treated with BamHI, and introduced into the plasmid pBS3 (WO2006/070944) at the BamHI site to construct a plasmid that was then used to delete sucA. This plasmid was inserted into the chromosome of the 2256 Δ ldhA strain, and then cured therefrom, so as to delete the sucA gene. Several variants of the obtained sucA deficient strain were cultured under a biotin-sufficient condition, and a strain having Glu-producing ability was selected. As a result, a Glu-producing strain having an IS mutation (V419::IS) in the yggB gene was obtained. The nucleotide sequence of the yggB gene having the IS mutation (V419::IS) and the amino acid sequence of the YggB protein encoded by this gene are shown in SEQ ID NOS: 23 and 24, respectively. The obtained Glu-producing strain was designated 2256 Δ ldhA Δ sucA yggB* strain.

A pitA expression plasmid (pVK9-Plac-pitA) was constructed by the following method. First, a pitA gene fragment was amplified by using the chromosomal DNA of the 2256 strain as the template as well as the primers 13 and 14. Then, the amplified fragment was ligated to the pVK9 plasmid (U.S. Patent Published Application No. 20060141588) treated with BamHI and PstI using In-Fusion (TaKaRa INC.) to construct a pitA expression plasmid. The constructed pitA expression plasmid was designated pVK9-Plac-pitA.

The constructed pVK9-Plac-pitA and pVK9 as a vector control each were introduced into the Glu-producing bacterium, 2256 Δ ldhA Δ sucA yggB* strain, to construct the 2256 Δ ldhA Δ sucA yggB*/pVK9-Plac-pitA strain and the 2256 Δ ldhA Δ sucA yggB*/pVK9 strain, respectively.

(2) Glu Production Culture

Glu production culture was performed by using the 2256 Δ ldhA Δ sucA yggB*/pVK9-Plac-pitA strain and the 2256 Δ ldhA Δ sucA yggB*/pVK9 strain. The composition of the medium used is shown in Table 2.

TABLE 2

|  | Medium 1 | Medium 2 |
|---|---|---|
| Glucose | 80 g/L | 80 g/L |
| (NH$_4$)$_2$SO$_4$ | 30 g/L | 30 g/L |
| KH$_2$PO$_4$ | 1 g/L | 1 g/L |
| MgSO$_4$·7H$_2$O | 0.4 g/L | 0.4 g/L |
| FeSO$_4$·7H$_2$O | 0.01 g/L | 0.01 g/L |
| MnSO$_4$·5H$_2$O | 0.01 g/L | 0.01 g/L |
| VB$_1$ | 200 μg/L | 200 μg/L |
| Biotin | 60 μg/L | 0 μg/L |
| Mameno | 0.48 g/L | 0.48 g/L |

A medium having the aforementioned composition and adjusted to pH 8.0 with KOH was prepared, sterilized by autoclaving (115° C., 15 minutes), and used for the culture.
<Culture Method>

Culture (preculture and main culture) was performed by putting 20 mL of the medium into a Sakaguchi flask, adding 50 g/L of CaCO$_3$ thereto, and shaking the medium at 31.5° C. with a box shaker. First, as the preculture, each of the aforementioned strains was cultured for 24 hours by using Medium 1. Then, 2 mL of the obtained preculture broth was inoculated to Medium 2, and Tween 40 (final concentration, 4 g/L) was added thereto 2 hours after the inoculation, to perform the main culture. The medium was sampled 17 hours after the inoculation. The residual saccharide and glutamic acid were quantified by using AS-310 (Asahi Chemical Industry).
<Results and Discussion>

The results are shown in Table 3. In Table 3, "RS" represents the amount of the residual saccharide, and "Glu" represents the amount of glutamic acid. It was revealed by this example that growth and Glu productivity of C. glutamicum are improved by increasing the expression of the pitA gene in C. glutamicum. Therefore, it was concluded that increasing the activity of the phosphate transporter encoded by the pitA gene is effective for production of an amino acid such as glutamic acid.

TABLE 3

| Strain | OD620 nm (×51) | RS (g/L) | Glu (g/L) |
|---|---|---|---|
| 2256 Δ IdhAΔ sucA yggB*/pVK9 | 0.498 | 26.2 | 35.8 |
| 2256 Δ IdhAΔ sucA yggB*/pVK9-Plac-pitA | 0.645 | 15.0 | 41.8 |

Example 2

Glu Production Culture Using pitA Mutant Strain

In this example, Glu production was performed by using a Glu-producing strain of C. glutamicum in which a mutation was introduced into the pitA gene, and influence of the mutation of the pitA gene on the Glu production was evaluated.

The strains used were as follows.

C. glutamicum 2256 Δ ldhA Δ sucA yggB*
C. glutamicum 2256 Δ ldhA Δ sucA yggB* pitAmut
Method for Constructing Bacterial Strains The 2256 Δ ldhA Δ sucA yggB* pitAmut strain in which a mutation was introduced into the pitA gene was constructed by using the 2256 Δ ldhA Δ sucA yggB* strain, which was a model Glu-producing strain constructed in Example 1, as the parent strain. The primers used are shown in Table 4.

TABLE 4

| Primer | Nucleotide Sequence (5' → 3') | SEQ ID NO: |
|---|---|---|
| 15 | gagctcggtacccggggatcc atggtcaccccaatcatggg | 27 |
| 16 | gccaagcttgcatgcctgcag ttacttggttacctcattct | 28 |

A plasmid pBS4S-pitAmut for introducing a mutation into pitA was constructed by the following method. PCR was performed by using the chromosomal DNA of the Glu-producing bacterium B3 strain in which a mutation replacing the phenylalanine residue at position 246 of the PitA protein with a serine residue (Phe246Ser ttc->tcc) was introduced into the coding region of the pitA gene as the template as well as the primers 15 and 16 to amplify a pitA gene fragment having the aforementioned mutation. Then, the amplified fragment was ligated to the pBS4S plasmid treated with PstI and BamHI by using In-Fusion (TaKaRa INC.) to construct a plasmid for introducing a mutation into pitA. The constructed plasmid for introducing a mutation into pitA was designated pBS4S-pitAmut.

The constructed pBS4S-pitAmut was inserted into the chromosome of the Glu-producing bacterium 2256 Δ ldhA Δ sucA yggB* strain, and then cured therefrom, so as to construct the 2256 Δ ldhA Δ sucA yggB* pitAmut strain in which the mutation was introduced into the pitA gene.

Although the aforementioned pitA mutated strain, 2256 Δ ldhA Δ sucA yggB* pitAmut strain, was constructed by using the plasmid for introducing a mutation constructed by using the chromosomal DNA of the Glu-producing bacterium B3 strain as the template, it can also be constructed by using a plasmid for introducing a mutation prepared with PrimeSTAR® Mutagenesis Basal Kit produced by Takara Bio. For example, PCR is performed by using the chromosomal DNA of a wild-type strain such as the *C. glutamicum* 2256 strain (ATCC 13869) as the template as well as the primers 15 and 16 to amplify a pitA gene fragment not having a mutation. Then, the amplified fragment is ligated to the plasmid pBS4S treated with BamHI and PstI by using In-Fusion (TaKaRa INC.) to construct a plasmid including the sequence of the wild-type pitA gene. Further, PCR can be performed by using this plasmid as the template as well as appropriate primers for modifying T at position 737 of the pitA gene into C according to the instruction of Prime-STAR® Mutagenesis Basal Kit to construct the plasmid pBS4S-pitAmut for introducing a mutation into pitA. The same pitA mutant strain can be constructed by using this plasmid.

Glu Production Culture

Glu production culture was performed by using the 2256 Δ ldhA Δ sucA yggB* strain and the 2256 Δ ldhA Δ sucA yggB* pitAmut strain. The composition of the medium used is shown in Table 5.

TABLE 5

| | Medium 3 |
|---|---|
| Glucose | 80 g/L |
| (NH$_4$)$_2$SO$_4$ | 30 g/L |
| KH$_2$PO$_4$ | 1 g/L |
| MgSO$_4$•7H$_2$O | 0.4 g/L |
| FeSO$_4$•7H$_2$O | 0.01 g/L |
| MnSO$_4$•5H$_2$O | 0.01 g/L |
| VB$_1$ | 200 µg/L |
| Biotin | 300 µg/L |
| Mameno | 0.48 g/L |

A medium having the aforementioned composition and adjusted to pH 8.0 with KOH was prepared, sterilized by autoclaving (115° C., 15 minutes), and used for the culture.

<Culture Method>

Culture (preculture and main culture) was performed by putting 20 mL of the medium into a Sakaguchi flask, adding 50 g/L of CaCO$_3$ thereto, and shaking the medium at 31.5° C. with a box shaker. First, as the preculture, each of the aforementioned strains was cultured for 24 hours by using Medium 3. Then, 2 mL of the obtained preculture broth was inoculated to Medium 3, and Tween 40 (final concentration, 4 g/L) was added thereto 2 hours after the inoculation, to perform the main culture. The medium was sampled 21.5 hours after the inoculation. The residual saccharide and glutamic acid were quantified by using AS-310 (Asahi Chemical Industry).

<Results and Discussion>

The results are shown in Table 6. In Table 6, "RS" represents the amount of the residual saccharide, and "Glu" represents the amount of glutamic acid. It was revealed by this example that growth and Glu productivity of *C. glutamicum* are improved by introducing the mutation (Phe246Ser) into the pitA gene in *C. glutamicum*. Therefore, it was concluded that this pitA mutation (Phe246Ser) is effective for production of an amino acid such as glutamic acid.

TABLE 6

| Strain | OD620 nm (×51) | RS (g/L) | Glu (g/L) |
|---|---|---|---|
| 2256 Δ IdhAΔ sucA yggB* | 0.867 | 0.0 | 45.8 |
| 2256 Δ IdhAΔ sucA yggB* pitAmut | 0.888 | 0.0 | 47.3 |

INDUSTRIAL APPLICABILITY

According to the present invention, an L-amino acid-producing ability of a coryneform bacterium can be improved, and an L-amino acid can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

EXPLANATION OF SEQUENCE LISTING

SEQ ID NO: 1, Nucleotide sequence of pitA gene of *E. coli* MG1655

SEQ ID NO: 2, Amino acid sequence of PitA protein of *E. coli* MG1655

SEQ ID NO: 3, Nucleotide sequence of the pitA gene of *Pantoea ananatis* LMG20103

SEQ ID NO: 4, Amino acid sequence of PitA protein of *Pantoea ananatis* LMG20103

SEQ ID NO: 5, Nucleotide sequence of pitA gene of *Corynebacterium glutamicum* 2256 (ATCC 13869)

SEQ ID NO: 6, Amino acid sequence of PitA protein of *Corynebacterium glutamicum* 2256 (ATCC 13869)

SEQ ID NOS: 7 to 20, Primers

SEQ ID NO: 21, Nucleotide sequence of yggB gene of *Corynebacterium glutamicum* 2256 (ATCC 13869)

SEQ ID NO: 22, Amino acid sequence of YggB protein of *Corynebacterium glutamicum* 2256 (ATCC 13869)

SEQ ID NO: 23, Nucleotide sequence of yggB gene (V419::IS) of *Corynebacterium glutamicum* 2256 (ATCC 13869)

SEQ ID NO: 24, Amino acid sequence of YggB protein (V419::IS) of *Corynebacterium glutamicum* 2256 (ATCC 13869)

SEQ ID NO: 25, Nucleotide sequence of pitA gene of *Corynebacterium glutamicum* ATCC 13032

SEQ ID NO: 26, Amino acid sequence of PitA protein of *Corynebacterium glutamicum* ATCC 13032

SEQ ID NOS: 27 and 28, Primers

The invention claimed is:

1. A method for producing an L-amino acid comprising:
   (A) culturing a coryneform bacterium having an L-amino acid producing ability in a medium; and
   (B) collecting the L-amino acid from the medium,
   wherein the bacterium has been modified to increase the expression of a gene encoding a phosphate transporter, wherein the increased expression of the gene is obtained by increasing the copy number of the gene and/or modifying an expression control sequence of the gene, wherein said phosphate transporter is selected from the group consisting of:
   (a) a protein which comprises the amino acid sequence of SEQ ID NO: 6 or SEQ ID NO: 26,
   (b) a protein which comprises all of SEQ ID NO: 6 or 26 except for the substitution, deletion, insertion or addition of 1 to 10 amino acid residues, wherein said protein has phosphate transporter activity,
   (c) a protein which comprises all of SEQ ID NO: 6 or 26 except for the replacement of the amino acid residue at a position corresponding to position 246 of SEQ ID NO: 6 with a serine residue, and
   (d) a protein which comprises all of SEQ ID NO: 6 or 26 except for (i) the replacement of the amino acid residue at a position corresponding to position 246 of SEQ ID NO: 6 with a serine residue, and (ii) the substitution, deletion, insertion or addition of 1 to 10 amino acid residues, wherein said protein has phosphate transporter activity.

2. The method according to claim 1, wherein the gene encoding the phosphate transporter is a DNA selected from the group consisting of:
   (a) a DNA comprising the nucleotide sequence of SEQ ID NO: 5 or 25, and
   (b) a DNA which is able to hybridize under stringent conditions with the full-length complement of the polynucleotide of SEQ ID NO: 5 or 25, wherein said stringent conditions comprise washing with 1×SSC, 0.1% SDS at 60° C., and wherein said DNA encodes a protein having phosphate transporter activity.

3. The method according to claim 1, wherein the bacterium is a *Corynebacterium* bacterium.

4. The method according to claim 3, wherein the bacterium is *Corynebacterium glutamicum*.

5. The method according to claim 1, wherein the L-amino acid is L-glutamic acid.

6. The method according to claim 5, wherein the L-glutamic acid is monoammonium L-glutamate or monosodium L-glutamate.

7. A method for producing an L-amino acid comprising:
   (A) culturing a coryneform bacterium having an L-amino acid producing ability in a medium; and
   (B) collecting the L-amino acid from the medium,
   wherein the bacterium has been modified to express a gene encoding a phosphate transporter, wherein said phosphate transporter is selected from the group consisting of:
   (a) a protein which comprises all of SEQ ID NO: 6 or 26 except for the replacement of the amino acid residue at a position corresponding to position 246 of SEQ ID NO: 6 with a serine residue, and
   (b) a protein which comprises all of SEQ ID NO: 6 or 26 except for (i) the replacement of the amino acid residue at a position corresponding to position 246 of SEQ ID NO: 6 with a serine residue, and (ii) the substitution, deletion, insertion or addition of 1 to 10 amino acid residues, wherein said protein has phosphate transporter activity.

8. The method according to claim 7, wherein the bacterium is a *Corynebacterium* bacterium.

9. The method according to claim 8, wherein the coryneform bacterium is *Corynebacterium glutamicum*.

10. The method according to claim 7, wherein the L-amino acid is L-glutamic acid.

11. The method according to claim 10, wherein the L-glutamic acid is monoammonium L-glutamate or monosodium L-glutamate.

* * * * *